US011859187B2

(12) United States Patent
Velasquez et al.

(10) Patent No.: US 11,859,187 B2
(45) Date of Patent: Jan. 2, 2024

(54) APTAMERS FOR PERSONAL HEALTH CARE APPLICATIONS

(71) Applicant: The Procter & Gamble Company, Cincinnati, OH (US)

(72) Inventors: Juan Esteban Velasquez, Cincinnati, OH (US); Spencer Christopher Rupard, Morrow, OH (US); Amy Violet Trejo, Mason, OH (US); Adam Michael Pitz, Morrow, OH (US); Kelly Lee Schmeichel, Cincinnati, OH (US); Erin Nicole Swigart, Morrow, OH (US); Gregory Allen Penner, London (CA)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/356,828

(22) Filed: Jun. 24, 2021

(65) Prior Publication Data
US 2021/0403919 A1 Dec. 30, 2021

Related U.S. Application Data

(60) Provisional application No. 63/043,952, filed on Jun. 25, 2020.

(51) Int. Cl.
| | |
|---|---|
| *C12N 15/113* | (2010.01) |
| *A61K 47/54* | (2017.01) |
| *A61K 47/60* | (2017.01) |
| *A61K 31/7088* | (2006.01) |
| *C12Q 1/68* | (2018.01) |

(52) U.S. Cl.
CPC ...... *C12N 15/1138* (2013.01); *A61K 31/7088* (2013.01); *A61K 47/549* (2017.08); *A61K 47/60* (2017.08); *C12N 2310/16* (2013.01); *C12N 2310/351* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,756,291 | A | 5/1998 | Griffin et al. |
| 8,778,307 | B2 | 7/2014 | Galindo et al. |
| 8,926,946 | B2 | 1/2015 | Muro Galindo et al. |
| 2005/0020651 | A1 | 1/2005 | Roche et al. |
| 2019/0077848 | A1 | 3/2019 | Schindler et al. |

FOREIGN PATENT DOCUMENTS

| | | |
|---|---|---|
| WO | 9119813 A1 | 12/1991 |
| WO | 2005110489 A2 | 11/2005 |
| WO | 2010144295 A1 | 12/2010 |
| WO | 2014068408 A2 | 5/2014 |
| WO | 2015031694 A2 | 3/2015 |
| WO | 2017035666 A1 | 3/2017 |
| WO | 2020020947 A1 | 1/2020 |

OTHER PUBLICATIONS

PCT Search Report for PCT/US2021/0138785 dated Oct. 5, 2021.
Charles et al. "Prevention of human rhinovirus infection by multivalent Fab molecules directed against ICAM-1", Antimicrobial AGents and Chemotherapy, vol. 47, No. 5, May 20, 2003, pp. 1503-1508.
Ellington, A.D. et al. "Selection in vitro of single-stranded DNA molecules that fold into specific ligand-binding structures" Nature 355: 850-852, 1992.
Ellington, A.D. et al."In vitro selection of RNA molecules that bind specific ligands", Nature 346: 818-822, 1990.
Hermanson GT, "Bioconjugate Techniques", pp. 969-1002, 2nd Edition, 2008.
Kim, YS et al. "Advances in Aptamer Screening andn Small Molecule Aptasensors", Adv. Biochem. Eng. Biotechnol, 2014 140:29-67 (Biosensors based on Aptamers and Enzymes).
Lineberger et al. "Domains 1 and 2 of ICAM-1 are sufficient to bind human rhinoviruses", Virus Research, vol. 14, No. 2 , Jul. 1, 1992, pp. 173-186.
Marlin et al. "A Soluble Form of Intercellular Adhesion Molecule-1 Inhibits Rhinovirus Infection", Nature, vol. 344, No. 6251, Mar. 1, 1990, pp. 70-72.
Newton et al. "Development of a Homogeneous High-Throughput Screening Assay for Biological Inhibitors of Human Rhinovirus Infection", Journal of Biomolecular Screening Society for Laboratory Automation and Screening, vol. 18, Jan. 1, 2012, pp. 237-246. URL:https://journals.sagepub.com/doi/pdf/10.1177/1087057112469047.
Stoltenburg, R. et al., "Selex—A (r)evolutionary method to generate high-affinity nucleic acid", Biomol. Eng. 2007 24 (4): 381-403.
The Vienna RNA Websuite. (http://rna.tbi.univie.ac.at//cgi-bin/RNAWebSuite/RNAfold.cgi. Gruber AR, et al., Nucleic Acids Research, vol. 36, Issue suppl_2, Jul. 1, 2008, pp. W70-W74.

*Primary Examiner* — Sean McGarry
(74) *Attorney, Agent, or Firm* — Gregory S. Darley-Emerson; Jason J. Camp

(57) ABSTRACT

An aptamer composition is disclosed which has one or more oligonucleotides that include at least one of deoxyribonucleotides, ribonucleotides, derivatives of deoxyribonucleotides, derivatives of ribonucleotides, or mixtures thereof. The aptamer composition has a binding affinity for one or more cellular membrane glycoproteins selected from the group consisting of: intercellular adhesion molecule 1 (ICAM-1), low-density lipoprotein receptor (LDLR) family members, and cadherin-related family member 3 (CDHR3), preferably intercellular adhesion molecule 1 (ICAM-1), and is configured to reduce the binding of one or more human rhinoviruses to the intercellular adhesion molecule 1 (ICAM-1).

24 Claims, 11 Drawing Sheets
Specification includes a Sequence Listing.

FIG. 10

| | | |
|---|---|---|
| ICAM-1 | ---QTSVSPSKVILPRGGSVLVTCSTSCDQPKLLGIETPLPKKELLLPGNNRKVYE LSNV | 57 |
| ICAM-3 | QEFLLRVEPQNPVLSAGGSLFVNCSTDCPSSEKIALETSLSKE-LVASGMGWAAFNLSNV | 59 |
| ICAM-5 | EPFWADLQPRVAFVERGGSLWLNCSTNCPRPERGGLETSLRRN-GTQRGLRWLARQLVDI | 59 |
| | :.*   .:  *;,*,*    :   ;:** * ::       *    . :* :: | |
| ICAM-1 | QE-DSQPMCYSNCPDGQSTAKTFLTVYWTPERVELAPLPSWQPVGKNLTLRCQVEGGAPR | 116 |
| ICAM-3 | TG-NSRILCSVYCRESQITGSSNITVYRLPERVELAPLPPWQPVGQNFTLRCQVEDGSPR | 118 |
| ICAM-5 | REPETQPVCFTRCARRTLQARGLIRTFQRPDRVELAPLPPWQPVGENFTLSCRVPGAGPR | 119 |
| | : : :*    *      .   : .;  *;**** ***  *****;*;** *;* .,,** | |
| ICAM-1 | ANLTVVLLRGEKELKREPAVGEP--------AEVTTTVLVRRDHHGANFSCRTELDLRPQGLE | 171 |
| ICAM-3 | TSLTVVLLRWEKELSRQPAVEEP-----ASVTATVLASRDDHGAPFSCRTELDMQPQGLG | 173 |
| ICAM-5 | ASLTLTLLRGAQELIRRSPAGEPPRARGAVLTATVLARREDHGANFSCRAELDLRPRGLG | 179 |
| | ;.;.*  ;** *..  **        * ;*;***. *;.*  ;**;*;*** | |
| ICAM-1 | LFENTSAPYQLQTFVLPATPPQLVSPRVLEVDTQGTVVCSLDGLFPVSEAQVHLALGDQR | 231 |
| ICAM-3 | LFVNTSAPRQLRTFVLPVTPPRLVAPRFLEVETSWPVDCTLDGLFPASEAQVYLALGDQM | 233 |
| ICAM-5 | LFENSSAPRELRTFSLSPDAPRLAAPRLLEVGSERPVSCTLDGLFPASEARVYLALGDQR | 239 |
| | **  *;***  ;*;** *   .*;  .*  ;.  *.*;*****,* ;******* | |
| ICAM-1 | LNPTVTYGNDSFSAKASVSVTAEDEGTQRLTCAVILGNQSETLQTVTIYSFPAPNVILT | 291 |
| ICAM-3 | LNATVMNHGDTLTATATATARADJEGARKIVCNVTLGGERRARENLTVFSFLGPIVNLS | 293 |
| ICAM-5 | LSPDVTLEGDAFVATATATASAREQEARQLVCNVTLGGENRETRENVTIYSFPAPLLTLS | 299 |
| | *; .  *   .*;; *,*;;,. *;;***;;,.* * **.; ;*;  ;.;;;** .*  * *; | |
| ICAM-1 | RPEVSEGTEVTVKCEARPRAKVTLNGVPAQPLGPRAQLLLKATPEDNGRSFSCSATLEVA | 351 |
| ICAM-3 | EPTAREGSTVTVSCMAGAPVQVTLDGVPAAAPGQPAQLQLNATESDDGRSFFCSATLEVD | 353 |
| ICAM-5 | EPSVSEGQMVTVTCAAGAQALVTLEGVPAAVPGQPAQLQLNATENDDRSFFCDATLDVD | 359 |
| | ;*  .   *.* *  ;.  *;**    *   *** *;** .*;  *** *;****;* | |
| ICAM-1 | GQLIHKNQTRELPVLYGPRLDERDCPGNWTWPENSQQTPMCQAWGNFLPELKCLKDG-TF | 410 |
| ICAM-3 | GEFLIRNSSVQLRVLYGPKIDRATCPQHLKWKDKTRHVLQCQARGNPYPELRCLKEGSSR | 413 |
| ICAM-5 | GETLIKNRSAELRVLYAPRLDRSDCPRSWTWPEGPEQTLRCEARGNPEPSVRCARSIKGA | 419 |
| | * ; :  ;* ; ;****** ;*;;    **    ;* .  ;;. *;* *** *;;;*  ;.. | |
| ICAM-1 | PLPIGESVTVTRDLEGTYLCRARSTQGEVTRKVTVNVLSPRYE---------------- | 453 |
| ICAM-3 | KVPVGIPFFVNVTHNGTYQCQASSSRGKYTLVVVMDIEAGSSH------------- | 456 |
| ICAM-5 | VLALGLLGPVTRALSGTYRCKAANDQREAVKDVTLTVEYAPALDSVGCPERITWLEGTEA | 479 |
| | ; ;*     *; .  .***  *;*   ,  ;*;   .   *;; : | |

FIG: 13

```
         (1)  1         10        20        30        40
Nas-3   (1)  ATTTTCGTTTTATTTCAGTTTAATTGCGTTTAGTATCTGG
Nas-88  (1)  ATTTTCGTTTTATTTTAGTTTAATTGCGTTTAGTATCTGG
```

FIG. 14

```
         (1)  1         10        20        30         43
Nas-45  (1)  GTAAAAATTAGAGAT-TAAAATAGTTCCTTT--CAGTTTTGTC
Nas-8   (1)  GTAAAAATTAAAGAGATTAA--GGT-CCTTAAGCAGTTTTGTC
```

```
         (1)  1         10        20        30        42
Nas-47  (1)  GTAAATAACCAGTTA-TA-CAGAAAGATCTCAGCAATTTATC
Nas-78  (1)  GTAATTAATCAAACAATAGCAGCAA-ATCTCAGCAATTT-TC
```

FIG. 15

```
         (1)  1         10        20        30         44
Nas-13  (1)  GTAAAAATTTTCAT--CTCAGCAAT--TAAATCCAAAGAATCCA
Nas-97  (1)  GTAAAAATTTAAATAACTCAGCAATCATAGATCCGACTGA----
```

```
         (1)  1         10        20        30         43
Nas-31  (1)  GTAAAAAGATAAAACTTAG---TTGCAGAATTTGCCTTCATT
Nas-93  (1)  GTAAATAACAAAAATCTCAGCTTTTGCAGAATTTATCCAC---
```

```
         (1)  1         10        20        30         43
Nas-39  (1)  GTAAAATAAAAGTTTTCCTATCAGCAAA-CTCACAAATTC---
Nas-82  (1)  GTAAA-TAAAAGCAGATCT--CAGCAAAACTCGTAAATTCAA
```

```
         (1)  1         10        20        30         44
Nas-61  (1)  GTAAAATAAAGAGGATAACTACAATCA-TCAGCA-ATCAT-AT-
Nas-91  (1)  GTAAAAATAA----ATAACTACGAGATCTCAGCAGATCATTATC
```

```
         (1)  1         10        20        30          45
Nas-87  (1)  GTAATTAAAAAACCTTCACA-CAGAAAACATTCCT-CAATTT---
Nas-94  (1)  ----GTAAATAAACT-CACAGCAGAAAAAATTCCTTCAACTTGTA
```

APTAMERS FOR PERSONAL HEALTH CARE APPLICATIONS

FIELD OF THE INVENTION

Described herein are nucleic acid aptamers that have a high binding affinity and specificity for cellular membrane glycoproteins and preferably for intercellular adhesion molecule-1 ("ICAM-1"), and more particularly the use of such aptamers to inhibit human rhinovirus binding to such glycoproteins and entering into cells within the nasal cavity and throat.

INCORPORATION BY REFERENCE OF THE SEQUENCE LISTING

This application contains, as a separate part of disclosure, a Sequence Listing in computer-readable form (Filename: 15819M_ST25.txt; Size: 98,100 bytes; Created: Jun. 18, 2021) which is incorporated by reference herein in its entirety.

BACKGROUND OF THE INVENTION

Aptamers are short single-stranded oligonucleotides, with a specific and complex three-dimensional shape, that bind to target molecules. The molecular recognition of aptamers is based on structure compatibility and intermolecular interactions, including electrostatic forces, van der Waals interactions, hydrogen bonding, and π-π stacking interactions of aromatic rings with the target material. The targets of aptamers include, but are not limited to, peptides, proteins, nucleotides, amino acids, antibiotics, low molecular weight organic or inorganic compounds, and even whole cells. The dissociation constant of aptamers typically varies between micromolar and picomolar levels, which is comparable to the affinity of antibodies to their antigens. Aptamers can also be designed to have high specificity, enabling the discrimination of target molecules from closely related derivatives.

Aptamers are usually designed in vitro from large libraries of random nucleic acids by Systematic Evolution of Ligands by Exponential Enrichment (SELEX). The SELEX method is first introduced in 1990 when single stranded RNAs are selected against low molecular weight dyes (Ellington, A. D., Szostak, J. W., 1990. Nature 346: 818-822). A few years later, single stranded DNA aptamers and aptamers containing chemically modified nucleotides are also described (Ellington, A. D., Szostak, J. W., 1992. Nature 355: 850-852; Green, L. S., et al., 1995. Chem. Biol. 2: 683-695). Since then, aptamers for hundreds of microscopic targets, such as cations, small molecules, proteins, cells, or tissues, have been selected. A compilation of examples from the literature is included in the database at the website: http://www.aptagen.com/aptamer-index/aptamer-list.aspx.

The common cold is the most frequent illness in the U.S., with 62 million people being infected each year. Adults can be infected with a common cold 2-4 times per year, while children can be infected 8-12 times per year. This leads to morbidity, frequent absences from school and work, reduced productivity, and inappropriate use of antibiotics. This translates into costing the U.S. $60 billion annually.

Human rhinoviruses cause 50-80% of common colds. Rhinoviruses are small (30 nm), nonenveloped single-stranded RNA viruses. Although rhinovirus infections are mild and self-limiting in immunocompetent hosts, it is associated with pneumonia in immunosuppressed patients, bronchiolitis in infants, and can exacerbate pre-existing pulmonary diseases such as asthma and chronic obstructive pulmonary disease.

Rhinovirus infection predominately occurs in the nasopharynx when the virus attaches to surface receptors on the nasal epithelium and infects the host cells. Ninety percent of rhinoviruses attach to ICAM-1 receptors that line the airways. Once the virus enters into the cell, it hijacks the cell's replication machinery to make copies of itself. This results in cell lysis and death, allowing the virus progeny to spread to other nearby cells to repeat the infectious cycle. Ultimately, this triggers a host immune response leading to respiratory symptoms (e.g. cough, rhinorrhea, congestion, sore throat, etc.). Despite the enormous public health burden, there are no licensed vaccines or antiviral drugs for human rhinovirus.

Aptamers against target proteins such as intercellular adhesion molecule 1 (ICAM-1) have previously been described. However, no data for the binding of such aptamers to the membrane bound protein or the capacity of these aptamers to prevent the binding of natural ligands or human rhinoviruses to ICAM-1 have been reported. Thus, a need still exists for aptamers that selectively bind to cellular membrane glycoproteins, including ICAM-1, and that prevent the binding of human rhinoviruses to such glycoproteins, mitigating symptoms for common cold or preventing (re)infection.

SUMMARY OF THE INVENTION

Described herein is the use of SELEX for the selection of aptamers against the intercellular adhesion molecule 1 (ICAM-1) and the use of such aptamers for the prevention of binding of human rhinoviruses to such glycoprotein.

Described herein is also an aptamer composition. The aptamer composition comprises at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for intercellular adhesion molecule 1 (ICAM-1), wherein the aptamer composition can reduce the binding of one or more human rhinoviruses to said intercellular adhesion molecule 1 (ICAM-1) and wherein the aptamer composition comprises
  (a) at least one oligonucleotide selected from the group consisting of oligonucleotides with at least 80% nucleotide sequence identity to sequences selected from the group consisting of SEQ ID NO: 1 to SEQ ID NO: 200; and/or;
  (b) at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

The aptamer composition may further show a binding affinity for one or more of low-density lipoprotein receptor (LDLR) family members, cadherin-related family member 3 (CDHR3), and combinations thereof.

The aptamer composition may comprise at least one oligonucleotide selected from the group consisting of SEQ ID NO: 2, SEQ ID NO: 4, SEQ ID NO: 5, SEQ ID NO: 7, and SEQ ID NO: 8. Also described herein is a personal health care composition. The personal health care composition comprises the aptamer composition as described herein. The personal health care composition may comprise at least one nucleic acid aptamer; wherein the nucleic acid aptamer has a binding affinity for intercellular adhesion molecule 1 (ICAM-1), wherein the nucleic acid aptamer reduces the binding of one or more human rhinoviruses to the intercellular adhesion molecule 1 (ICAM-1) and wherein the aptamer composition comprises
- (a) at least one oligonucleotide selected from the group consisting of oligonucleotides with at least 80% nucleotide sequence identity to sequences selected from the group consisting of SEQ ID NO: 1 to SEQ ID NO: 200; and/or;
- (b) at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

The aptamer composition may further show a binding affinity for one or more of low-density lipoprotein receptor (LDLR) family members, cadherin-related family member 3 (CDHR3), and combinations thereof.

A method for delivering a personal health care composition to the upper respiratory tract is also provided. The method comprises administering a personal health care composition as described herein; the personal health care composition comprises at least one nucleic acid aptamer; wherein the at least one nucleic acid aptamer has a binding affinity for intercellular adhesion molecule 1 (ICAM-1), wherein the nucleic acid aptamer reduces the binding of one or more human rhinoviruses to the intercellular adhesion molecule 1 (ICAM-1) and wherein the aptamer composition comprises
- (a) at least one oligonucleotide selected from the group consisting of oligonucleotides with at least 80% nucleotide sequence identity to sequences selected from the group consisting of SEQ ID NO: 1 to SEQ ID NO: 200; and/or;
- (b) at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

In one aspect, the personal health care composition can also comprise one or more active ingredients; wherein the at least one nucleic acid aptamer and the one or more active ingredients are covalently or non-covalently attached.

Described herein is further the use of the aptamer composition as disclosed herein and/or the use of the personal health care composition as disclosed herein for inhibiting human rhinovirus infection by inhibiting binding to the intercellular adhesion molecule 1 (ICAM-1) and thereby inhibiting entering into cells within the nasal cavity and throat. The use may include delivering the aptamer composition and/or the personal health care composition as disclosed herein to the upper respiratory tract.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 6 shows the fluorescently labelled aptamer Nas.R-4 bound to HNepC and to HEK293 cells.

FIG. 7 shows the viral inhibition test on HeLa cells using aptamer Nas.R-2, aptamer Nas.R-8 and a negative control aptamer.

FIG. 10 shows the amino acid sequence alignment of ICAM-1 (see SEQ ID NO: 214), ICAM-3 (see SEQ ID NO: 232), and ICAM-5 (see SEQ ID NO: 234).

FIG. 13 shows alignment of exemplary sequences with at least 90% nucleotide sequence identity that are identified during the selection process (Nas-3 (see, e.g., SEQ ID NO: 103) and Nas-88 (see, e.g., SEQ ID NO: 188)).

FIG. 14 shows alignment of exemplary sequences with at least 70% nucleotide sequence identity that are identified during the selection process (Nas-45 (see, e.g., SEQ ID NO: 145), Nas-8 (see, e.g., SEQ ID NO: 108), Nas-47 (see, e.g., SEQ ID NO: 147), and Nas-78 (see, e.g., SEQ ID NO: 178).

FIG. 15 shows alignment of exemplary sequences with at least 50% nucleotide sequence identity that are identified during the selection process (Nas-13 (see, e.g., SEQ ID NO: 113), Nas-97 (see, e.g., SEQ ID NO: 197), Nas-31 (see, e.g., SEQ ID NO: 131), Nas-93 (see, e.g., SEQ ID NO: 193), Nas-39 (see, e.g., SEQ ID NO: 139), Nas-82 (see, e.g., SEQ ID NO: 182), Nas-61 (see, e.g., SEQ ID NO: 161), Nas-91 (see, e.g., SEQ ID NO: 191), Nas-87 (see, e.g., SEQ ID NO: 187), and Nas-94 (see, e.g., SEQ ID NO: 194).

DETAILED DESCRIPTION OF THE INVENTION

I. Definitions

Figure 1:
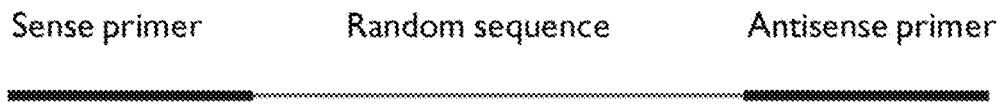
FIG. 1 illustrates a schematic of the DNA library.

As used herein, the term "aptamer" refers to a single stranded oligonucleotide or a peptide that has a binding affinity for a specific target.

As used herein, the term "nucleic acid" refers to a polymer or oligomer of nucleotides. Nucleic acids are also referred as "ribonucleic acids" when the sugar moiety of the nucleotides is D-ribose and as "deoxyribonucleic acids" when the sugar moiety is 2-deoxy-D-ribose.

As used herein, the term "nucleotide" refers to a compound consisting of a nucleoside esterified to a monophosphate, polyphosphate, or phosphate-derivative group via the hydroxyl group of the 5-carbon of the sugar moiety. Nucleotides are also referred as "ribonucleotides" when the sugar moiety is D-ribose and as "deoxyribonucleotides" when the sugar moiety is 2-deoxy-D-ribose.

As used herein, the term "nucleoside" refers to a glycosylamine consisting of a nucleobase, such as a purine or pyrimidine, usually linked to a 5-carbon sugar (e.g. D-ribose or 2-deoxy-D-ribose) via a β-glycosidic linkage. Nucleosides are also referred as "ribonucleosides" when the sugar moiety is D-ribose and as "deoxyribonucleosides" when the sugar moiety is 2-deoxy-D-ribose.

As used herein, the term "nucleobase" refers to a compound containing a nitrogen atom that has the chemical properties of a base. Non-limiting examples of nucleobases are compounds comprising pyridine, purine, or pyrimidine moieties, including but not limited to, adenine, guanine, hypoxanthine, thymine, cytosine, and uracil.

As used herein, the term "oligonucleotide" refers to an oligomer composed of nucleotides.

As used herein, the term "identical" or "sequence identity", in the context of two or more oligonucleotides, nucleic acids, or aptamers, refers to two or more sequences that are the same or have a specified percentage of nucleotides that are the same, when compared and aligned for maximum correspondence, as measured using sequence comparison algorithms or by visual inspection.

As used herein, the term "substantially homologous" or "substantially identical", in the context of two or more oligonucleotides, nucleic acids, or aptamers, generally refers to two or more sequences or subsequences that have at least 40%, 60%, 80%, 90%, 95%, 96%, 97%, 98% or 99% nucleotide identity, when compared and aligned for maximum correspondence, as measured using sequence comparison algorithms or by visual inspection.

As used herein, the term "epitope" refers to the region of a target that interacts with the aptamer. An epitope can be a contiguous stretch within the target or can be represented by multiple points that are physically proximal in a folded form of the target.

As used herein, the term "motif" refers to the sequence of contiguous, or series of contiguous, nucleotides occurring in a library of aptamers with binding affinity towards a specific target and that exhibits a statistically significant higher probability of occurrence than would be expected compared to a library of random oligonucleotides. The motif sequence is frequently the result or driver of the aptamer selection process.

As used herein, the term "personal health care compositions" refers to compositions in a form that is directly deliverable to the upper respiratory tract.

As used herein, "a pharmaceutically effective amount" refers to an amount sufficient to confer a therapeutic effect on the subject. In some aspects the therapeutic effect is reduced rhinovirus binding to cellular membrane glycoproteins such as ICAM-1, reduced severity and/or duration of a cold, or reduced incidence of respiratory illness due to rhinovirus.

II. Aptamer Composition

The human rhinoviruses (RV) are the predominant cause of the common cold. They are classified in three groups (RV-A, RV-B, and RV-C), including around 160 types that express different surface proteins. Despite this diversity, rhinoviruses utilize mostly three glycoproteins of epithelial cells to cross the cellular membrane and access the host cell replication machinery: intercellular adhesion molecule 1 or ICAM-1 protein, utilized by the majority of RV-A and all RV-B types; low-density lipoprotein receptor or LDLR family members, utilized by at least twelve RV-A types; and cadherin-related family member 3 or CADHR3 proteins, utilized mostly by RV-C types.

An aptamer composition may comprise at least one oligonucleotide selected from the group consisting of deoxyribonucleotides, ribonucleotides, derivatives of deoxyribonucleotides, derivatives of ribonucleotides, and mixtures thereof, wherein the aptamer composition has a binding affinity for intercellular adhesion molecule 1 (ICAM-1). In one aspect, the aptamer composition may have a binding affinity for one or more cellular membrane glycoproteins selected from the group consisting of intercellular adhesion molecule 1 (ICAM-1), low-density lipoprotein receptor (LDLR) family members, and cadherin-related family member 3 (CDHR3) and combinations thereof. Preferably the one or more cellular membrane glycoprotein is intercellular adhesion molecule 1 (ICAM-1). The aptamer composition can reduce the binding of one or more human rhinoviruses to the intercellular adhesion molecule 1 (ICAM-1).

The aptamer composition may comprise at least one oligonucleotide selected from the group consisting of oligonucleotides with at least 80% nucleotide sequence identity to sequences selected from the group consisting of SEQ ID NO: 1 to SEQ ID NO: 200. The aptamer composition may comprise at least one oligonucleotide selected from the group consisting of oligonucleotides with at least 90% nucleotide sequence identity to sequences selected from the group consisting of SEQ ID NO: 1 to SEQ ID NO: 200. The aptamer composition may comprise at least one oligonucleotide selected from the group consisting of oligonucleotides with at least 95% nucleotide sequence identity to sequences selected from the group consisting of SEQ ID NO: 1 to SEQ ID NO: 200. The aptamer composition may comprise at least one oligonucleotide selected from the group consisting of SEQ ID NO: 1 to SEQ ID NO: 200. A non-limiting example of oligonucleotide with at least 90% nucleotide sequence identity to SEQ ID NO: 3 is SEQ ID NO: 88.

The aptamer composition may comprise at least one oligonucleotide selected from the group consisting of oligonucleotides containing at least 10 contiguous nucleotides from sequences selected from the group consisting of SEQ ID NO: 201 to SEQ ID NO: 212.

The aptamer composition may comprise at least one oligonucleotide selected from the group consisting of SEQ ID NO: 2, SEQ ID NO: 4, SEQ ID NO: 5, SEQ ID NO: 7, and SEQ ID NO: 8. The aptamer composition may comprise at least one oligonucleotide selected from the group consisting of oligonucleotides with at least 50% nucleotide sequence identity to sequences selected from the group consisting of SEQ ID NO: 2, SEQ ID NO: 4, SEQ ID NO: 5, SEQ ID NO: 7, and SEQ ID NO: 8. The aptamer composition may comprise at least one oligonucleotide selected from the group consisting of oligonucleotides with at least 70% nucleotide sequence identity to sequences selected from the group consisting of SEQ ID NO: 2, SEQ ID NO: 4, SEQ ID NO: 5, SEQ ID NO: 7, and SEQ ID NO: 8. The aptamer composition may comprise at least one oligonucleotide selected from the group consisting of oligonucleotides with at least 90% nucleotide sequence identity to sequences selected from the group consisting of SEQ ID NO: 2, SEQ ID NO: 4, SEQ ID NO: 5, SEQ ID NO: 7, and SEQ ID NO: 8. A non-limiting example of oligonucleotide with at least 50% nucleotide sequence identity to SEQ ID NO: 4 is SEQ ID NO: 35. Non-limiting examples of oligonucleotides with at least 50% nucleotide sequence identity to SEQ ID NO: 7 are SEQ ID NO: 36, SEQ ID NO: 50, SEQ ID NO: 77, and SEQ ID NO: 97. Non-limiting examples of oligonucleotides with at least 50% nucleotide sequence identity to SEQ ID NO: 8 are SEQ ID NO: 12, SEQ ID NO: 22, SEQ ID NO: 29, SEQ ID NO: 44, SEQ ID NO: 45, SEQ ID NO: 53, SEQ ID NO: 63, SEQ ID NO: 74, and SEQ ID NO: 89.

The at least one oligonucleotide can comprise one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212. The aptamer composition may comprise at least one oligonucleotide comprising a sequence of nucleotides with at least 80% nucleotide sequence identity to sequences selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212. The aptamer composition may comprise at least one oligonucleotide comprising a sequence of nucleotides with at least 90% nucleotide sequence identity to sequences selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212. The aptamer composition may comprise at least one oligonucleotide comprising a sequence of nucleotides with at least 95% nucleotide sequence identity to sequences selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

In one aspect, the aptamer composition has a binding affinity for the human intercellular adhesion molecule 1 (ICAM-1) (SEQ ID NO: 213), its natural variants, polymorphic variants, or any post-translationally modified versions of said protein. Non-limiting examples of posttranslational modifications of ICAM-1 are disulfide bonds (e.g. between Cys48 and Cys92, Cys52 and Cys96, Cys135 and Cys186, Cys237 and Cys290, Cys332 and Cys371, Cys403 and Cys419, Cys431 and Cys457), glycosylations (e.g. at Asn130, Asn145, Asn183, Asn202, Asn267, Asn296, Asn385, and Asn406), phosphorylations (e.g. at Thr521 or Thr530), and ubiquitination.

In one aspect, the aptamer composition has a binding affinity for the extracellular domain of human intercellular adhesion molecule 1 (ICAM-1) (SEQ ID NO: 214) or any post-translationally modified versions of said domain. In one aspect, the aptamer composition has a binding affinity for one or more domains of the intercellular adhesion molecule 1 (ICAM-1) selected from the group consisting of: Ig-like C2-type 1 domain (SEQ ID NO: 215), Ig-like C2-type 2 domain (SEQ ID NO: 216), Ig-like C2-type 3 domain (SEQ ID NO: 217), Ig-like C2-type 4 domain (SEQ ID NO: 218), Ig-like C2-type 5 domain (SEQ ID NO: 219), any post-translationally modified versions of said domains, and mixtures thereof. In one aspect, the aptamer composition has a binding affinity for the Ig-like C2-type 1 domain (SEQ ID NO: 215) of the intercellular adhesion molecule 1 (ICAM-1), any post-translationally modified versions of said domain, and mixtures thereof.

In one aspect, the aptamer composition has a binding affinity for one or more regions of the human intercellular adhesion molecule 1, wherein said regions comprise an amino acid sequence selected from the group consisting of SEQ ID NO: 220, SEQ ID NO: 221, SEQ ID NO: 222, SEQ ID NO: 223, and fragments of said sequences.

Chemical modifications can introduce new features into the aptamers such as different molecular interactions with the target, improved binding capabilities, enhanced stability of oligonucleotide conformations, or increased resistance to nucleases. In one aspect, the at least one oligonucleotide of the aptamer composition may comprise natural or non-natural nucleobases. Natural nucleobases are adenine, cytosine, guanine, thymine, and uracil. Non-limiting examples of non-natural nucleobases can include hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, bromouracil, 5-iodouracil, and mixtures thereof.

Modifications of the phosphate backbone of the oligonucleotides can also increase the resistance against nuclease digestion. In one aspect, the nucleosides of the oligonucleotides may be linked by a chemical motif selected from the group consisting of natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In one aspect, the nucleosides of the oligonucleotides may be linked by natural phosphate diesters.

In one aspect, the sugar moiety of the nucleosides of the oligonucleotides may be selected from the group consisting of ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N, N-dimethylacetamidyl ribose, N-morpholinophosphordiamidate, α-deoxyribofuranosyl, other pentoses, hexoses, and mixtures thereof.

In one aspect, the derivatives of ribonucleotides or said derivatives of deoxyribonucleotides may be selected from the group consisting of locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

In one aspect, the nucleotides at the 5'- and 3'-ends of the at least one oligonucleotide may be inverted. In one aspect, at least one nucleotide of the at least one oligonucleotide may be fluorinated at the 2' position of the pentose group. In one aspect, the pyrimidine nucleotides of said at least one oligonucleotide may be fluorinated at the 2' position of the pentose group. In one aspect, said aptamer composition may comprise at least one polymeric material, wherein said at least one polymeric material is covalently linked to said at least one oligonucleotide. In one aspect, said at least one polymeric material may be polyethylene glycol.

In one aspect, said at least one oligonucleotide may be between about 10 and about 200 nucleotides in length. In one aspect, said at least one oligonucleotide may be less than about 100 nucleotides in length, alternatively said at least one oligonucleotide may be less than about 50 nucleotides in length.

In one aspect, said at least one oligonucleotide may be covalently or non-covalently attached to one or more active ingredients. In one aspect, said one or more active ingredients may be selected from the group comprising respiratory illness treatment agents, cold-treatment agents, flu-treatment agents, antiviral agents, antimicrobial agents, cooling sensates, warming sensates, malodor absorbing agents, natural extracts, peptides, enzymes, pharmaceutical active ingredients, metal compounds, and mixtures thereof. In one aspect, said one or more active ingredients can include, but are not limited to, pharmaceutical active ingredients, menthol, levomenthol, zinc and salts thereof, *eucalyptus*, camphor, and combinations thereof. Suitable active ingredients include any material that is generally considered as safe and that provides health care benefits.

In one aspect, said at least one oligonucleotide may be non-covalently attached to said one or more active ingredients via molecular interactions. Examples of molecular interactions are electrostatic forces, van der Waals interactions, hydrogen bonding, and π-π stacking interactions of aromatic rings.

In one aspect, said at least one oligonucleotide may be covalently attached to said one or more active ingredients using one or more linkers or spacers. Non-limiting examples of linkers are chemically labile linkers, enzyme-labile linkers, and non-cleavable linkers. Examples of chemically labile linkers are acid-cleavable linkers and disulfide linkers. Acid-cleavable linkers take advantage of low pH to trigger hydrolysis of an acid-cleavable bond, such as a hydrazone bond, to release the active ingredient or payload. Disulfide linkers can release the active ingredients under reducing environments. Examples of enzyme-labile linkers are peptide linkers that can be cleaved in the presence of proteases and β-glucuronide linkers that are cleaved by glucuronidases releasing the payload. Non-cleavable linkers can also release the active ingredient if the aptamer is degraded by nucleases.

In one aspect, said at least one oligonucleotide may be covalently or non-covalently attached to one or more nanomaterials. In the present invention, said at least one oligonucleotide and said one or more active ingredients may be covalently or non-covalently attached to one or more nanomaterials. In one aspect, said one or more active ingredients may be carried by said one or more nanomaterials. Non-limiting examples of nanomaterials can include gold nanoparticles, nano-scale iron oxides, carbon nanomaterials (such as single-walled carbon nanotubes and graphene oxide), mesoporous silica nanoparticles, quantum dots, liposomes, poly (lactide-co-glycolic acids) nanoparticles, polymeric micelles, dendrimers, serum albumin nanoparticles, DNA-based nanomaterials, and combinations thereof. These nanomaterials can serve as carriers for large volumes of active ingredients, while the aptamers can facilitate the delivery of the nanomaterials with the actives to the expected target.

Nanomaterials can have a variety of shapes or morphologies. Non-limiting examples of shapes or morphologies can include spheres, rectangles, polygons, disks, toroids, cones, pyramids, rods/cylinders, and fibers. In the context of the present invention, nanomaterials usually have at least one spatial dimension that is less than about 100 µm and more preferably less than about 10 µm. Nanomaterials comprise materials in solid phase, semi-solid phase, or liquid phase.

1. Aptamers can also be peptides that bind to targets with high affinity and specificity. These peptide aptamers can be part of a scaffold protein. Peptide aptamers can be isolated from combinatorial libraries and improved by directed mutation or rounds of variable region mutagenesis and selection. In one aspect, said aptamer composition may comprise at least one peptide or protein; wherein said aptamer composition has a binding affinity for one or more cellular membrane glycoproteins, wherein said one or more cellular membrane glycoproteins can be selected from the group consisting of: intercellular adhesion molecule 1 (ICAM-1), low-density lipoprotein receptor (LDLR) family members, and cadherin-related family member 3 (CDHR3); preferably intercellular adhesion molecule 1 (ICAM-1) and wherein said aptamer is configured to reduce the binding of one or more human rhinoviruses to said cellular membrane glycoproteins, preferably the intercellular adhesion molecule 1 (ICAM-1). In particular said aptamer composition may comprise at least one peptide or protein translated from
   (a) at least one oligonucleotide selected from the group consisting of oligonucleotides with at least 80% nucleotide sequence identity to sequences selected from the group consisting of SEQ ID NO: 1 to SEQ ID NO: 200; and/or;
   (b) at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

III. Methods of Designing Aptamer Compositions

The method of designing nucleic acid aptamers known as Systematic Evolution of Ligands by Exponential Enrichment (SELEX) has been broadly studied and improved for the selection of aptamers against small molecules and proteins (WO 91/19813). In brief, in the conventional version of SELEX, the process starts with the synthesis of a large library of oligonucleotides consisting of randomly generated sequences of fixed length flanked by constant 5'- and 3'-ends that serve as primers. The oligonucleotides in the library are then exposed to the target ligand and those that do not bind the target are removed. The bound sequences are eluted and amplified by PCR (polymerase chain reaction) to prepare for subsequent rounds of selection in which the stringency of the elution conditions is usually increased to identify the tightest-binding oligonucleotides. In addition to conventional SELEX, there are improved versions such as capillary electrophoresis-SELEX, magnetic bead-based SELEX, cell- SELEX, automated SELEX, complex-target SELEX, among others. A review of aptamer screening methods is found in (1) Kim, Y. S. and M. B. Gu, "Advances in Aptamer Screening and Small Molecule Aptasensors", Adv. Biochem. Eng. Biotechnol., 2014 140:29-67 (Biosensors based on Aptamers and Enzymes) and (2) Stoltenburg, R., et al. (2007) "SELEX-A (r)evolutionary method to generate high-affinity nucleic acid ligands" Biomol. Eng. 2007 24(4): 381-403, the contents of which are incorporated herein by reference. Although the SELEX method has been broadly applied, it is neither predictive nor standardized for every target. Instead, a method must be developed for each particular target in order for the method to lead to viable aptamers.

Despite the large number of selected aptamers, SELEX has not been routinely applied for the selection of aptamers with binding affinities towards cellular membrane glycoproteins such as intercellular adhesion molecule 1 (ICAM-1), low-density lipoprotein receptor (LDLR) family members, and cadherin-related family member 3 (CDHR3) and that prevent the binding of human rhinoviruses to such proteins. Unexpectedly, the inventors have found that SELEX can be used for the design of aptamers that prevent the binding of human rhinoviruses to the ICAM-1 receptor.

Selection Library

In SELEX, the initial candidate library is generally a mixture of chemically synthesized DNA oligonucleotides, each comprising a long variable region of n nucleotides flanked at the 3' and 5' ends by conserved regions or primer recognition regions for all the candidates of the library. These primer recognition regions allow the central variable region to be manipulated during SELEX in particular by means of PCR.

The length of the variable region determines the diversity of the library, which is equal to $4^n$ since each position can be occupied by one of four nucleotides A, T, G or C. For long variable regions, huge library complexities arise. For instance, when n=50, the theoretical diversity is $4^{50}$ or $10^{30}$, which is an inaccessible value in practice as it corresponds to more than 105 tons of material for a library wherein each sequence is represented once. The experimental limit is around $10^{15}$ different sequences, which is that of a library wherein all candidates having a variable region of 25 nucleotides are represented. If one chooses to manipulate a library comprising a 30-nucleotide variable region whose theoretical diversity is about $10^{18}$, only 1/1000 of the possibilities will thus be explored. In practice, that is generally sufficient to obtain aptamers having the desired properties. Additionally, since the polymerases used are unreliable and introduce errors at a rate on the order of $10^{-4}$, they contribute to significantly enrich the diversity of the sequence pool throughout the SELEX process. One candidate in 100 will be modified in each amplification cycle for a library with a random region of 100 nucleotides in length, thus leading to the appearance of $10^{13}$ new candidates for the overall library.

In one aspect, the starting mixture of oligonucleotides may comprise more than about $10^6$ different oligonucleotides and more preferably between about $10^{13}$ to about $10^{15}$ different oligonucleotides. In one aspect, the length of the variable region may be between about 10 and about 100 nucleotides. In one aspect, the length of the variable region may be between about 20 and about 60 nucleotides. In one aspect, the length of the variable region may be about 40 nucleotides. Random regions shorter than 10 nucleotides may be used but may be constrained in their ability to form secondary or tertiary structures and in their ability to bind to target molecules. Random regions longer than 100 nucleotides may also be used but may present difficulties in terms of cost of synthesis. The randomness of the variable region is not a constraint of the present invention. For instance, if previous knowledge exists regarding oligonucleotides that bind to a given target, libraries spiked with such sequences may work as well or better than completely random ones.

In the design of primer recognition sequences, care should be taken to minimize potential annealing among sequences, fold back regions within sequences, or annealing of the same sequence itself. In one aspect, the length of primer recognition sequences may be between about 10 and about 40 nucleotides. In one aspect, the length of primer recognition sequences may be between about 12 and about 30 nucleotides. In one aspect, the length of primer recognition sequences may be between about 18 and about 26 nucleotides, i.e., about 18, 19, 20, 21, 22, 23, 24, 25 or 26 nucleotides. The length and sequence of the primer recognition sequences determine their annealing temperature. In one aspect, the primer recognition sequences of said oligonucleotides may have an annealing temperature between about 60° C. and about 72° C.

Aptamers can be ribonucleotides (RNA), deoxynucleotides (DNA), or their derivatives. When aptamers are ribonucleotides, the first SELEX step may consist of transcribing the initial mixture of chemically synthesized DNA oligonucleotides via the primer recognition sequence at the 5' end. After selection, the candidates are converted back into DNA by reverse transcription before being amplified. RNA and DNA aptamers having comparable characteristics have been selected against the same target and reported in the art. Additionally, both types of aptamers can be competitive inhibitors of one another, suggesting potential overlapping of interaction sites.

New functionalities, such as hydrophobicity or photoreactivity, can be incorporated into the oligonucleotides by modifications of the nucleobases before or after selection. Modifications at the C-5 position of pyrimidines or at the C-8 or N-7 positions of purines are especially common and compatible with certain enzymes used during the amplification step in SELEX. In one aspect, said oligonucleotides may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, 5-bromouracil, 5-iodouracil, and mixtures thereof. Some non-natural nucleobases, such as 5-bromouracil or 5-iodouracil, can be used to generate photo-crosslinkable aptamers, which can be activated by UV light to form a covalent link with the target.

In one aspect, the nucleosides of said oligonucleotides may be linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In one aspect, the nucleosides of said oligonucleotides may be linked by natural phosphate diesters.

In one aspect, the sugar moiety of the nucleosides of said oligonucleotides may be selected from the group comprising ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N, N-dimethylacetamidyl ribose, N-morpholinophosphordiamidate, α-deoxyribofuranosyl, other pentoses, hexoses, and mixtures thereof.

In one aspect, said derivatives of ribonucleotides or said derivatives of deoxyribonucleotides may be selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

When using modified nucleotides during the SELEX process, they should be compatible with the enzymes used during the amplification step. Non-limiting examples of modifications that are compatible with commercial enzymes include modifications at the 2' position of the sugar in RNA libraries. The ribose 2'-OH group of pyrimidine nucleotides can be replaced with 2'-amino, 2'-fluoro, 2'-methyl, or 2'-O-methyl, which protect the RNA from degradation by nucleases. Additional modifications in the phosphate linker, such as phosphorothionate and boranophosphate, are also compatible with the polymerases and confer resistance to nucleases.

In one aspect, at least one nucleotide of said oligonucleotides may be fluorinated at the 2' position of the pentose group. In one aspect, the pyrimidine nucleotides of said oligonucleotides may be at least partially fluorinated at the 2' position of the pentose group. In one aspect, all the pyrimidine nucleotides of said oligonucleotides may be fluorinated at the 2' position of the pentose group. In one aspect, at least one nucleotide of said oligonucleotides may be aminated at the 2' position of the pentose group.

Another approach, recently described as two-dimensional SELEX, simultaneously applies in vitro oligonucleotide selection and dynamic combinatorial chemistry (DCC), e.g., a reversible reaction between certain groups of the oligonucleotide (amine groups) and a library of aldehyde compounds. The reaction produces imine oligonucleotides, which are selected on the same principles as for conventional SELEX. It is thus possible to identify for a target hairpin RNA modified aptamers that differ from natural aptamers.

A very different approach relates to the use of optical isomers. Natural oligonucleotides are D-isomers. L-analogs are resistant to nucleases but cannot be synthesized by polymerases. According to the laws of optical isomerism, an L-series aptamer can form with its target (T) a complex having the same characteristics as the complex formed by the D-series isomer and the enantiomer (T') of the target (T). Consequently, if compound T' can be chemically synthesized, it can be used to perform the selection of a natural aptamer (D). Once identified, this aptamer can be chemically synthesized in an L-series. This L-aptamer is a ligand of the natural target (T).

Selection Step

Single stranded oligonucleotides can fold to generate secondary and tertiary structures, resembling the formation of base pairs. The initial sequence library is thus a library of three-dimensional shapes, each corresponding to a distribution of units that can trigger electrostatic interactions, create hydrogen bonds, etc. Selection becomes a question of identifying in the library the shape suited to the target, i.e., the shape allowing the greatest number of interactions and the formation of the most stable aptamer-target complex. For small targets (dyes, antibiotics, etc.) the aptamers identified are characterized by equilibrium dissociation constants in the micromolar range, whereas for protein targets Kd values below $10^{-9}$ M are not rare.

Selection in each round occurs by means of physical separation of oligonucleotides associated with the target from free oligonucleotides. Multiple techniques may be applied (chromatography, filter retention, electrophoresis, etc.). The selection conditions are adjusted (relative concentration of target/candidates, ion concentration, temperature, washing, etc.) so that a target-binding competition occurs between the oligonucleotides. Generally, stringency is increased as the rounds proceed in order to promote the capture of oligonucleotides with the highest affinity. In addition, counter-selections or negative selections are carried out to eliminate oligonucleotides that recognize the support or unwanted targets (e.g., filter, beads, etc.).

The SELEX process for the selection of target-specific aptamers is characterized by repetition of five main steps: (1) binding of oligonucleotides to the target, (2) partition or removal of oligonucleotides with low binding affinity, (3) elution of oligonucleotides with high binding affinity, (4) amplification or replication of oligonucleotides with high binding affinity, and (5) conditioning or preparation of the oligonucleotides for the next cycle. This selection process is designed to identify the oligonucleotides with the greatest affinity and specificity for the target material.

In one aspect, a method of designing an aptamer composition may comprise the step of contacting: a) a mixture of oligonucleotides, b) a selection buffer, and c) a target material comprising one or more cellular membrane glycoproteins selected from the group consisting of: intercellular adhesion molecule 1 (ICAM-1), low-density lipoprotein receptor (LDLR) family members, cadherin-related family member 3 (CDHR3), truncations thereof, and mixtures thereof; preferably intercellular adhesion molecule 1 (ICAM-1) and truncations thereof. In another aspect, the method of designing an aptamer composition may comprise the step of contacting: a) a mixture of oligonucleotides, b) a selection buffer, and c) cells expressing one or more cellular membrane glycoproteins selected from the group consisting of: intercellular adhesion molecule 1 (ICAM-1), low-density lipoprotein receptor (LDLR) family members, cadherin-related family member 3 (CDHR3), truncations thereof, and mixtures thereof; preferably intercellular adhesion molecule 1 (ICAM-1) and truncations thereof. In yet another aspect, the method of designing an aptamer composition may comprise the step of contacting: a) a mixture of oligonucleotides, b) a selection buffer, and c) human nasal epithelial cells expressing one or more cellular membrane glycoproteins selected from the group consisting of: intercellular adhesion molecule 1 (ICAM-1), low-density lipoprotein receptor (LDLR) family members, cadherin-related family member 3 (CDHR3), truncations thereof, and mixtures thereof; preferably intercellular adhesion molecule 1 (ICAM-1) and truncations thereof.

In one aspect, said mixture of oligonucleotides may comprise oligonucleotides selected from the group consisting of deoxyribonucleotides, ribonucleotides, derivatives of deoxyribonucleotides, derivatives of ribonucleotides, and mixtures thereof. Furthermore, said one or more cellular membrane glycoproteins or truncations thereof can be isolated, in mixture with other materials such as proteins or peptides, or part of a cell expressing said glycoproteins.

SELEX cycles are usually repeated several times until oligonucleotides with high binding affinity are identified. The number of cycles depends on multiple variables, including target features and concentration, design of the starting random oligonucleotide library, selection conditions, ratio of target binding sites to oligonucleotides, and the efficiency of the partitioning step. In one aspect, said contacting step may be performed at least 5 times. In one aspect, said contacting step may be performed between 6 and 30 times. In one aspect, said method further may comprise the step of removing the oligonucleotides that do not bind said target material during said contacting step.

Oligonucleotides are oligo-anions, each unit having a charge and hydrogen-bond donor/acceptor sites at a particular pH. Thus, the pH and ionic strength of the selection buffer are important and should represent the conditions of the intended aptamer application. In one aspect, the pH of said selection buffer may be between about 2 and about 9, alternatively between about 5 and about 8.

Cations do not only facilitate the proper folding of the oligonucleotides, but also can provide benefits. In one aspect, said selection buffer may comprise cations. Non-limiting examples of cations are $Na^+$, $K^+$, $Mg^{2+}$, $Ca^{2+}$.

In order for the aptamers to maintain their structures and function during their application, the in vitro selection process can be carried out under conditions similar to those for which they are being developed. In one aspect, said selection buffer may comprise a solution or suspension of a personal health care composition selected from the group comprising tablets, lyophilized tablets, lollipops, lozenges, liquid center-filled confectioneries, candies, powders, granular substances, films, liquids, solutions, suspensions, mouth rinses or gargles, saline washes, dispersible fluids, sprays, quick dissolving fibers, vapors, creams, ointments, powders, granular substances, films, and combinations thereof.

In one aspect, said selection buffer may comprise at least one surfactant. In one aspect, the at least one surfactant may be selected from the group consisting of anionic surfactants, amphoteric or zwitterionic surfactants, and mixtures thereof. Non-limiting examples of anionic surfactants are alkyl and alkyl ether sulfates or sulfonates, including ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and combinations thereof. Non-limiting amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate, including cocoamphoacetate, cocoamphodiacetate, lauroamphoacetate, lauroamphodiacetate, and mixtures thereof. Non-limiting examples of zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate, and betaine.

The selection buffer may comprise at least one material selected from the group comprising: aqueous carriers, gel matrixes, silicone conditioning agents, organic conditioning materials, non-ionic polymers, deposition aids, rheology modifier/suspending agents, benefit agents, and mixtures thereof. Non-limiting examples of aqueous carriers are water and water solutions of lower alkyl alcohols and polyhydric alcohols, including ethanol, isopropanol, propylene glycol, hexylene glycol, glycerin, and propane diol. Non-limiting examples of gel matrixes include water solutions of fatty alcohols, including cetyl alcohol, stearyl alcohol, behenyl alcohol, and mixtures thereof. Non-limiting examples of silicone conditioning agents include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Non-limiting examples of organic conditioning materials include hydrocarbon oils, polyolefins, fatty esters, fluorinated conditioning compounds, fatty alcohols, alkyl glucosides and alkyl glucoside derivatives, quaternary ammonium compounds, polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M, and mixtures thereof. Non-limiting examples of non-ionic polymers include polyalkylene glycols, such as polyethylene glycols. Non-limiting examples of deposition aids include copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone; vinyl esters, vinyl alcohol (made by hydrolysis of polyvinyl acetate), maleic anhydride, propylene glycol, and ethylene glycol, cationic celluloses, cationic starches, and cationic guar gums. Non-limiting examples of rheology modifier/suspending agents include homopolymers based on acrylic acid, methacrylic acid or other related derivatives, alginic acid-based materials, and cellulose derivatives. Non-limiting examples of benefit agents include brightening agents, strengthening agents, anti-fungal agents, anti-bacterial agents, anti-microbial agents, anti-dandruff agents, anti-malodor agents, perfumes, olfactory enhancement agents, anti-itch agents, cooling agents, anti-adherence agents, moisturization agents, smoothness agents, surface modification agents, antioxidants, natural extracts and essential oils, dyes, pigments, bleaches, nutrients, peptides, vitamins, enzymes, chelants, and mixtures thereof.

Negative selection or counter-selection steps can minimize the enrichment of oligonucleotides that bind to undesired targets or undesired epitopes within a target. In one aspect, said method of designing an aptamer composition may further comprise the step of contacting: a) a mixture of oligonucleotides, b) a selection buffer, and c) one or more undesired targets. Methods for negative selection or counterselection of aptamers against unbound targets have been published in WO201735666, the content of which is incorporated herein by reference.

The method of designing an aptamer composition may comprise the steps of: a) synthesizing a mixture of oligonucleotides; b) contacting: i. said mixture of oligonucleotides, ii. a selection buffer, and iii. a target material comprising one or more cellular membrane glycoproteins; wherein said glycoproteins are selected from the group consisting of: intercellular adhesion molecule 1 (ICAM-1), its fragments, and combinations thereof, to produce a target suspension; c) removing the liquid phase from said target suspension to produce a target-oligonucleotide mixture; d) contacting said target-oligonucleotide mixture with a washing buffer and removing the liquid phase to produce a target-aptamer mixture; and e) contacting said target-aptamer mixture with an elution buffer and recovering the liquid phase to produce an aptamer mixture. In one aspect, said steps may be performed repetitively at least 5 times. In one aspect, said steps may be performed between 6 and 30 times, preferably less than 20 times.

In another aspect, a method of designing an aptamer composition comprising the steps of: a) synthesizing a random mixture of deoxyribonucleotides comprising oligonucleotides consisting of: i. a T7 promoter sequence at the 5'-end, ii. a variable 40-nucleotide sequence in the middle, and iii. a conserved reverse primer recognition sequence at the 3'end; b) transcribing said random mixture of deoxyribonucleotides using pyrimidine nucleotides fluorinated at the 2' position of the pentose group and natural purine nucleotides and a mutant T7 polymerase to produce a mixture of fluorinated ribonucleotides; c) contacting: i. said mixture of fluorinated ribonucleotides, ii. a selection buffer, and iii. a target material comprising one or more cellular membrane glycoproteins; wherein said glycoproteins are selected from the group consisting of: intercellular adhesion molecule 1 (ICAM-1), its fragments, and combinations thereof, to produce a target suspension; d) removing the liquid phase from said target suspension to produce a target-oligonucleotide mixture; e) contacting said target-oligonucleotide mixture with a washing buffer and removing the liquid phase to produce a target-aptamer mixture; f) contacting said target-aptamer mixture with an elution buffer and recovering the liquid phase to produce an RNA aptamer mixture; g) reserve transcribing and amplifying said RNA aptamer mixture to produce a DNA copy of said RNA aptamer mixture; and h) sequencing said DNA copy of said RNA aptamer mixture.

Post-Selection Modification

To enhance stability of the aptamers, chemical modifications can be introduced in the aptamer after the selection process. For instance, the 2'-OH groups of the ribose moieties can be replaced by 2'-fluoro, 2'-amino, or 2'-O-methyl groups. Furthermore, the 3'- and 5'-ends of the aptamers can be capped with different groups, such as streptavidin-biotin, inverted thymidine, amine, phosphate, polyethylene-glycol, cholesterol, fatty acids, proteins, enzymes, fluorophores, among others, making the oligonucleotides resistant to exonucleases or providing some additional benefits. Other modifications are described in previous sections of the present disclosure.

Unlike backbone modifications which can cause aptamer-target interaction properties to be lost, it is possible to conjugate various groups at one of the 3'- or 5'-ends of the oligonucleotide in order to convert it into a delivery vehicle, tool, probe, or sensor without disrupting its characteristics. This versatility constitutes a significant advantage of aptamers, in particular for their application in the current invention. In one aspect, one or more personal care active ingredients may be covalently attached to the 3'-end of said at least one oligonucleotide. In one aspect, one or more personal care active ingredients may be covalently attached to the 5'-end of said at least one oligonucleotide. In one aspect, one or more personal care active ingredients may be covalently attached to random positions of said at least one oligonucleotide.

Incorporation of modifications to aptamers can be performed using enzymatic or chemical methods. Non-limiting examples of enzymes used for modification of aptamers are terminal deoxynucleotidyl transferases (TdT), T4 RNA ligases, T4 polynucleotide kinases (PNK), DNA polymerases, RNA polymerases, and other enzymes known by those skilled in the art. TdTs are template-independent polymerases that can add modified deoxynucleotides to the 3' terminus of deoxyribonucleotides. T4 RNA ligases can be used to label ribonucleotides at the 3'-end by using appropriately modified nucleoside 3',5'-bisphosphates. PNK can be used to phosphorylate the 5'-end of synthetic oligonucleotides, enabling other chemical transformations (see below). DNA and RNA polymerases are commonly used for the random incorporation of modified nucleotides throughout the sequence, provided such nucleotides are compatible with the enzymes.

Non-limiting examples of chemical methods used for modification of aptamers are periodate oxidation of ribonucleotides, EDC activation of 5'-phosphate, random chemical labeling methods, and other chemical methods known by those skilled in the art, incorporated herein.

During periodate oxidation, meta- and ortho-periodates cleave the C—C bonds between vicinal diols of 3'-ribonucleotides, creating two aldehyde moieties that enable the conjugation of labels or active ingredients at the 3'-end of RNA aptamers. The resulting aldehydes can be easily reacted with hydrazine- or primary amine-containing molecules. When amines are used, the produced Schiff bases can be reduced to more stable secondary amines with sodium cyanoborohydride (NaCNBH3).

When EDC activation of 5'-phosphate is used, the 5'-phosphate of oligonucleotides is frequently activated with EDC (1-Ethyl-3-[3-dimethylaminopropyl]carbodiimide hydrochloride) and imidazole to produce a reactive imidazolide intermediate, followed by reaction with a primary amine to generate aptamers modified at the 5'end. Because the 5' phosphate group is required for the reaction, synthetic oligonucleotides can be first treated with a kinase (e.g. PNK).

Random chemical labeling can be performed with different methods. Because they allow labeling at random sites along the aptamer, a higher degree of modification can be achieved compared to end-labeling methods. However, since the nucleobases are modified, binding of the aptamers to their target can be disrupted. The most common random chemical modification methods involve the use of photoreactive reagents, such as phenylazide-based reagents. When the phenylazide group is exposed to UV light, it forms a labile nitrene that reacts with double bonds and C—H and N—H sites of the aptamers.

Additional information about methods for modification of aptamers is summarized in Hermanson G. T., "Bioconjugate Techniques", pp. 969-1002, 2nd Edition, Academic Press, San Diego, 2008, the content of which is incorporated herein by reference.

After selection, in addition to chemical modifications, sequence truncations can be performed to remove regions that are not essential for binding or for folding into the structure. Moreover, aptamers can be linked together to provide different features or better affinity. Thus, any truncations or combinations of the aptamers described herein can also be incorporated in the aptamer composition.

IV. Application of Aptamer Compositions in Personal Health Care Products

Described herein are personal health care compositions and methods for using such compositions for the prevention and treatment of cold-like symptoms due to respiratory tract viral infections. In some aspects, a personal health care composition comprises at least one aptamer as disclosed herein; wherein the at least one aptamer has a binding affinity for ICAM-1 and is configured to reduce the binding of one or more human rhinoviruses to the intercellular adhesion molecule 1 (ICAM-1). The personal health care composition can be preferably applied to areas of the upper respiratory tract, such as the nasal cavity and throat, to provide a barrier to rhinovirus binding and entrance into cells.

The personal health care composition preferably comprises a pharmaceutically effective amount of at least one aptamer. In some aspects, the personal health care composition can comprise between about 0.001% to about 1% of the at least one aptamer, alternatively from about 0.005% to about 0.5%, alternatively from about 0.01% to about 0.1%, all by weight of the composition.

The personal health care compositions can be administered orally or intranasally. In one aspect, the personal health care composition can be an oral composition. An oral composition can be in liquid form, semi-solid form, suspension form, or in any solid form that is capable of quickly dissolving in the mouth. Non-limiting examples of oral dosage forms can include tablets, lyophilized tablets, lollipops, lozenges, liquid center-filled confectioneries, candies, powders, granular substances, films, liquids, solutions, suspensions, mouth rinses or gargles, saline washes, dispersible fluids, sprays, quick dissolving fibers, such as polyvinylpyrrolidone and poly(vinyl alcohol), and combinations thereof. Solid oral dosage forms can be of any desired size, shape, weight, consistency or hardness, bearing in mind that it should not be swallowed before it disintegrates and can easily fit inside the mouth. Alternatively, the personal health care composition can be a nasal composition. A nasal composition can be in any dosage form capable of quickly dispersing in the nose. Non-limiting examples of nasal dosage forms can include vapors, creams, ointments, powders, granular substances, films, liquids, dispersible fluids, sprays, and combinations thereof.

As used herein, the term "administering" with respect to a human/mammal means that the human/mammal ingests or is directed to ingest, or does ingest, or deliver, or chew, or drink, or spray, or place in mouth or nose, or inhale one or more of the personal health care compositions. Administration may be on an as-needed or as-desired basis, for example, once-weekly, or daily, including multiple times daily, for example, at least once daily, at least twice daily, at least three times daily, or at least four times daily.

The personal health care compositions may be administered to prevent and treat cold-like symptoms. As used herein "cold-like symptoms" refer to symptoms typically associated with respiratory tract viral infections. These symptoms include, but are not limited to, nasal congestion, chest congestion, sneezing, rhinorrhea, fatigue or malaise, coughing, fever, sore throat, headache, and other known cold symptoms.

As further used herein, "treat" or "treatment" with respect to respiratory illness means that administration of the referenced composition prevents, alleviates, ameliorates, inhibits, or mitigates one or more symptoms of the respiratory illness or the respiratory illness itself, or any like benefit with respect to the respiratory illness in a mammalian subject in need thereof, preferably in humans. As such, this includes, for example: preventing a respiratory illness or its associated symptoms from occurring in a mammal, for example when the mammal is predisposed to acquiring the respiratory illness, but has not yet been diagnosed with the illness; inhibiting the respiratory illness or its associated symptoms; and/or alleviating, reversing, or curing the respiratory illness or its associated symptoms. Insofar as the methods of the present invention are directed to preventing a respiratory illness, it is understood that the term "prevent" does not require that the respiratory illness be completely thwarted. Rather, as used herein, the term "preventing" or the like refers to the ability of the skilled artisan to identify susceptibility to respiratory illness (such as, for example, in humans during winter months), such that administration of the referenced compositions may occur prior to the onset of the symptoms associated with the illness.

The personal health care compositions and methods of the present invention can comprise, consist of, or consist essentially of, the essential elements and limitations of the invention described herein, as well as any additional or optional ingredients, components, or limitations described herein or otherwise useful in personal health care compositions intended for use by a subject.

All parts, percentages, and ratios herein are by weight unless otherwise specified. All such weights as they pertain to listed ingredients are based on the active level and, therefore do not include solvents or by-products that may be included in commercially available materials, unless otherwise specified. All measurements referred to herein are made at 25° C. unless otherwise specified.

The personal health care compositions of the present invention may include one or more of the following:

The personal health care composition can comprise a solvent. Non-limiting examples of solvents include water, propylene glycol, ethanol, glycerin, polyethylene glycol, and combinations thereof. Solvent can be present in an amount of from about 2% to about 99%, by weight of the composition, alternatively from about 5% to about 95%, alternatively from about 10% to about 80, alternatively from about 12% to about 65%, alternatively from about 20% to about 50%.

The personal health care composition can comprise a thickening agent. Non-limiting examples of thickening agents can include carboxymethylcellulose (CMC), carboxymethylcellulose sodium; and mixtures thereof. When present, the composition can comprise from about 0.01% to about 60% of a thickening agent, alternatively from about 0.1% to about 40%, alternatively from about 1% to about 30%, alternatively from about 2% to about 20%, alternatively from about 3% to about 15%, all by weight of the composition. In one aspect, the thickening agent can provide a moisturizing and/or hydration benefit that relieves the cough on contact and/or provides aid in healing the mouth and/or throat.

The personal health care composition can comprise a diluent. Non-limiting examples of diluents can include microcrystalline cellulose, silicified microcrystalline cellulose, such as ProSolv® SMCC 90 (commercially available from JRS Pharma, Patterson, NY, USA), dextrose, mannitol, sorbitol, maltodextrin, maltitol, and combinations thereof. Suitable diluent levels are from about 20% to about 90% diluent, by weight of the composition, alternatively from about 30% to about 85%, alternatively from about 40% to about 83%, alternatively from about 50% to about 80%, alternatively from about 60% to about 78%.

The personal health care composition can comprise a disintegrant. A disintegrant can be included to formulate a rapid disintegration of the solid oral dosage form following administration. Non-limiting examples of disintegrants can include crospovidone, sodium starch glycolate, crosslinked sodium carboxymethyl cellulose, low substituted hydroxypropylcellulose, guar gum, sodium alginate, and mixtures thereof. Suitable disintegrant levels are from about 1% to about 20%, by weight of the composition, alternatively from about 2% to about 15%, alternatively from about 3% to about 10%, alternatively from about 5% to about 8%.

In one aspect, a composition can comprise mannitol and crospovidone to provide quick disintegration and dissolution. One advantage to using a soluble sugar, like mannitol, is that it can pick up water and dissolve quickly. One advantage to using a disintegrant, like crospovidone, is that it can absorb water and swell, thus causing the dosage form to break apart. As a dosage form breaks apart it is exposed to liquid, such as saliva in the oral cavity, and can dissolve faster. The ratio of mannitol to crospovidone can be about 15:1, alternatively about 13:1 alternatively about 10:1.

The personal health care composition can comprise a lubricant. Non-limiting examples of lubricants can include sodium stearyl fumarate, magnesium stearate, calcium stearate, zinc stearate, stearic acid, glyceryl behenate, hydrogenated vegetable oils, talc, polyethylene glycol, mineral oil, and combinations thereof. Suitable levels of lubricant are from about 0.05% to about 5% lubricant, by weight of the composition, alternatively from about 0.1% to about 3%, alternatively from about 0.25% to about 1.5%, alternatively from about 0.3% to about 1%, alternatively from about 0.4% to about 0.6%.

In one aspect, the personal health care composition can be a non-Newtonian, or thixotropic, fluid, exhibiting a reduced apparent viscosity while being subjected to shear forces, but a high apparent viscosity while at rest. One advantage to a non-Newtonian fluid is that it permits application by spraying with a pump spray device or squeeze-type spray bottle immediately following the application of a shearing force (such as those created by vigorously shaking the device) but causes the sprayed material to remain at least temporarily relatively immobile on mucosal membranes or the skin. Preferably, the composition can have a very rapid rate of viscosity recovery following withdrawal of the shearing force.

The personal health care composition can comprise a rheology-modifying agent. Non-limiting examples of rheology-modifying agents can include sodium carboxymethyl cellulose, algin, carrageenans (including iota, kappa, lambda carrageenan, and combinations thereof), carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch, microcrystalline cellulose, mixtures of microcrystalline cellulose and carboxymethylcellulose sodium (commercially available as Avicel® RC-591 from FMC Corporation, Philadelphia, Pa), xanthan gum, and combinations thereof. Suitable levels of rheology-modifying agents can be from about 0.5% to about 15%, alternatively from about 1% to about 12%, alternatively from about 2% to about 6%, all by weight of the composition. Rheology-modifying agents can not only provide viscosity benefits but can also coat the nose and throat longer to sooth and/or deliver an agent of choice.

The personal health care composition may further comprise a humectant. Humectants, which can be hygroscopic materials such as glycerin, a polyethylene or other glycol, a polysaccharide, aloe, and the like, act to inhibit water loss from the composition and may add moisturizing qualities.

The personal health care composition can comprise an acidic agent. The acidic agent can comprise organic acids, pyroglutamic acid, and combinations thereof. Suitable organic acid can include, but are not limited to, ascorbic acid, monocarboxylic acids, dicarboxylic acids, tricarboxylic acids, and mixtures thereof. Specific non-limiting examples of suitable monocarboxylic, dicarboxylic, or tricarboxylic acids include salicylic, fumaric, benzoic, glutaric, lactic, citric, malonic, acetic, glycolic, malic, adipic, succinic, aspartic, phthalic, tartaric, glutamic, gluconic, and mixtures thereof. Without being limited by theory, it is believed that incorporating acids in a nasal composition can create a hostile environment for viruses without significantly irritating specific areas of the respiratory tract such as the nasal tissues. The composition can comprise from about 0.01% to about 10% organic acid, alternatively from about 0.05% to about 5%, alternatively from about 0.10% to about 2.5%, all by weight of the composition.

The personal health care composition can comprise a surfactant spreading aid such as polyoxyethylene (20) sorbitan mono-oleate, commercially sold as Polysorbate 80, Polyoxyethylene (20) sorbitan monolaurate, commercially sold as Polysorbate 20, Polyoxyl 400 stearate, polyethylene glycol, Polyethylene-polypropylene glycol, commercially sold as Poloxamer 407, and combinations thereof. The surfactants can be included in the composition at concentrations ranging from about 0.001% to about 10%, alternatively from about 0.01% to about 5%, alternatively from about 0.1% to about 3%, by weight of the composition.

Additional Components

The personal health care composition described herein may optionally comprise one or more additional components known for use in personal health care products, provided that the additional components are physically and chemically compatible with the components described herein, or do not otherwise unduly impair product stability, aesthetics, or performance. Optional components suitable for use herein include materials such as preservatives, pH adjusting agents, chelating agents, metal compounds, pharmaceutical active ingredients, vitamins, herbal ingredients, sweeteners, sensates, flavoring agents, natural honey, volatile oils, aromatic components such as camphor, eucalyptol, menthol, fragrances and the like, antioxidants, amino acids, energy boosting ingredients, sleep aids, sodium chloride, and combinations thereof. The optional components can be included in the personal health care composition at concentrations ranging from about 0.001% to about 20%, alternatively from about 0.01% to about 10%, alternatively from about 0.1% to about 5%, all by weight of the composition.

In one aspect, the personal health care composition can comprise a preservative. Preservatives can optionally be included to prevent microbial contamination. Non-limiting examples of preservatives can include benzalkonium chloride, chlorhexidine gluconate, phenyl ethyl alcohol, phenoxyethanol, benzyl alcohol, sorbic acid, thimerosal, phenylmercuric acetate, methylparaben, propylparaben, butylparaben, chlorobutanol, and mixtures thereof.

In one aspect, the personal health care composition can comprise a pH adjusting agent. Non-limiting examples of pH adjusting agents can include sodium bicarbonate, sodium phosphate, sodium hydroxide, ammonium hydroxide, sodium stannate, triethanolamine, sodium citrate, disodium succinate, and mixtures thereof. Optional pH adjusting agents can be included in the composition to adjust the pH to a value of from about 2 to about 8, alternatively from about 2 to about 5. If present, the pH adjusting agents are generally included at concentrations ranging from about 0.01 to about 5.0%, by weight of the composition.

In one aspect, the personal health care composition can comprise a chelating agent. Non-limiting examples of suitable optional chelating agents can include phytic acid, disodium and calcium salts of ethylene diamine tetraacetic acid (EDTA), tetrasodium EDTA, sodium hexametaphosphate (SHMP), di(hydroxyethyl)glycine, 8-hydroxyquinoline, and mixtures thereof. The chelating agents can be included at concentrations ranging from about 0.001% to 10%, preferably from about 0.005% to about 5%, more preferably from about 0.01% to about 2%, by weight of the composition.

The personal health care composition can comprise a metal compound. Metal compounds suitable for use herein include those metal compounds containing a metal ion selected from the group consisting of manganese (Mn), silver (Ag), zinc (Zn), tin (Sn), iron (Fe), copper (Cu), aluminum (Al), nickel (Ni), cobalt (Co), and mixtures thereof. Non-limiting examples of a metal compound suitable for use herein include zinc acetate, zinc chloride, zinc ascorbate, zinc gluconate, zinc pidolate, zinc succinate, zinc sulphate, zinc edetate, and mixtures thereof. Zinc acetate is the most preferred metal compound.

When the personal health care composition comprises a metal compound containing a zinc ion, it is believed that the zinc ion provides for antiviral properties. Zinc ions have been shown to be both antiviral and antibacterial. They are believed to inhibit cleavage of rhinovirus polypeptides, preventing replication and formation of infective virions. Zinc ions reduce the ability of rhinoviruses to penetrate cell membranes, partly by lowering expression of intercellular adhesion molecule ICAM. Zinc ions have also been shown to stimulate T-cell lyphocytes, including production of the natural antiviral, interferon-gamma. They stabilize cell plasma membranes, protecting cells from cytotoxic agents, and preventing cell leakage. Furthermore, it is known that metal ions such as iron, silver, copper, and zinc can provide antiviral properties for the prevention and treatment of cold and influenza-like symptoms. The concentration of the metal compound in the personal health care compositions can range from about 0.001% to about 20%, alternatively from about 0.01% to about 10%, alternatively from about 0.05% to about 5%, alternatively from about 0.1% to about 2%, alternatively from 0.2% to about 1%, all by weight of the composition.

Non-limiting examples of pharmaceutical active ingredients can include menthol; anesthetics such as benzocaine and lidocaine; decongestants such as phenylephrine, pseudoephedrine, xylometazoline, and oxymetazoline; antihistamines such as doxylamine, diphenhydramine, loratadine, and cetirizine; expectorants such as guaifenesin, ambroxol, and bromhexine; pain relievers such as acetaminophen (APAP), ibuprofen, ketoprofen, diclofenac, naproxen, and aspirin; antitussives such as dextromethorphan, codeine, chlophedi32101, and levodropropizine; the free and addition salts thereof; and combinations thereof. Pharmaceutical active ingredients can be present at a level from about 0.01% to about 25%, alternatively from about 0.05% to about 15%, alternatively from about 0.1% to about 10%, from about 1% to about 5%, all by weight of the composition. In one aspect, the personal healthcare composition can comprise at least one aptamer and one or more pharmaceutical active ingredients to provide relief of one or more symptoms and inhibit rhinovirus binding.

Non-limiting examples of vitamins can include Vitamin A, Vitamin C, Vitamin D2, Vitamin D3, Vitamin E, Vitamin K1, Vitamin K3, Vitamin B1, vitamin B3, folic acid, Vitamin B12, Vitamin B3, Vitamin B7, and combinations thereof. In some aspects, the composition can comprise from about 0.1 to about 10% vitamins, alternatively from about 1 to about 8%, alternatively from about 2 to about 6%, all by weight of the composition.

Non-limiting examples of herbal ingredients can include rosemary (leaf), ginger, lemon balm, green tea, holy basil, oregano, thyme, ashwagandha, bacopa, chamomile, valerian, rosemary, turmeric, grapeseed, blueberry, coffee, curcumin, elderberry, marshmallow root, ivy leaf, black tea, white tea, oolong tea, green tea, and combinations thereof. In some aspects, the herbal ingredient can be whole herbs or plant parts, extracts, powders, concentrates, or combinations thereof. In some aspects, the composition can comprise from about 0.1 to about 10% herbal ingredients, alternatively from about 1 to about 8%, alternatively from about 2 to about 6%, all by weight of the composition.

In one aspect, the sweetener can be selected from the group comprising sugar alcohols, synthetic sweeteners, high intensity natural sweeteners, and combinations thereof.

Non-limiting examples of nutritive sweeteners can include sucrose, dextrose, glucose, fructose, lactose, tagatose, maltose, trehalose, high fructose corn syrup, and combinations thereof. Nutritive sweeteners can be present in an amount from about 1% to about 99%, by weight of the composition, alternatively from about 4% to about 95%, alternatively from about 10% to about 70%, alternatively from about 15% to about 60%, alternatively from about 25% to about 50%, in another example about 35% to about 45%.

Non-limiting examples of sugar alcohols can include xylitol, sorbitol, mannitol, maltitol, lactitol, isomalt, erythritol, and combinations thereof. Sugar alcohols can be present in an amount from about 5% to about 70%, by weight of the composition, alternatively from about 10% to about 60%, alternatively from about 15% to about 55%, alternatively from about 25% to about 50%, alternatively from about 30% to about 45%.

Non-limiting examples of synthetic sweeteners can include aspartame, acesulfame potassium, alitame, sodium saccharin, sucralose, neotame, cyclamate, and combinations thereof. Synthetic sweeteners can be present in an amount from about 0.01% to about 10%, by weight of the composition, alternatively from about 0.05% to about 5%, alternatively about 0.1% to about 3%, alternatively from about 0.2% to about 1%, alternatively from about 0.1% to about 0.5%.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. High intensity natural sweeteners can be present in an amount from about 0.01% to about 10% by weight of the composition, alternatively about 0.05% to about 5%, alternatively from about 0.1% to about 3%, alternatively from about 0.5% to about 1%.

The personal health care composition can comprise a flavoring system comprising sensates, flavoring agents, salivating agents, and combinations thereof.

The personal health care composition can comprise a sensate. Non-limiting examples of sensates can include cooling sensates, warming sensates, tingling sensates, and combinations thereof. Sensates can deliver sensory signals to the mouth, throat, nasal, and/or sinus passages so that the personal health care composition may be perceived by the user as immediately acting to alleviate an ailment and/or to provide a soothing sensation.

Non-limiting examples of cooling sensates can include WS-23 (2-Isopropyl-N,2,3-trimethylbutyramide), WS-3 (N-ethyl-p-menthane-3-carboxamide), WS-30 (1-glyceryl-p-menthane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (ethyl 3-(p-menthane-3-carboxamido) acetate), menthol, levomenthol, 1-menthone glycerol ketal (sold as Frescolat® MGA by Symrise, Holzminden, Germany), (−)-Menthyl lactate (sold as Frescolat® ML by Symrise, Holzminden, Germany), (−)-Menthoxypropane-1,2-diol (sold as Coolact® 10 by Vantage Specialty Ingredients, Inc., Warren, NJ), 3-(1-menthoxy)-2-methylpropane-1,2-diol, (−)-Isopulegol (sold as Coolact P® by Takasago International, Tokyo, Japan), cis & trans p-Menthane-3,8-diols (sold Coolact® 38D by Takasago International), menthyl pyrrolidone carboxylate (sold as Questice® by Givaudan Active Beauty, Verbuer, Switzerland), (1R,3R,4S)-3-menthyl-3,6-dioxaheptanoate (available from Firmenich, Geneva, Switzerland), (1R,2S,5R)-3-menthyl methoxyacetate (available from Firmenich), (1R,2S,5R)-3-menthyl 3,6,9-trioxadecanoate (available from Firmenich), (1R,2S,5R)-menthyl 11-hydroxy-3,6,9-trioxaundecanoate (available from Firmenich), (1R,2S,5R)-3-menthyl (2-hydroxyethoxy) acetate (available from Firmenich), Icilin also known as AG-3-5 (chemical name 1-(2-hydroxyphenyl)-4-(3-nitrophenyl)-3,6-dihydropyrimidin-2-one), 4-methyl-3-(1-pyrrolidinyl)-2[5H]-furanone, Peppermint oil, Spearmint oil, L-Monomenthyl succinate, L-monomenthyl glutarate, 2-1-menthoxyethanol (Coolact® 5), 3-1-Menthoxy propane-1,2-diol (sold as TK10 by Takasago International), N-(4-cyanomethylphenyl)-p-menthanecarboxamide (sold as Evercool™ 180 by Givaudan), and combinations thereof. Cooling sensates can be present from about 0.001% to about 1%, by weight of the composition, alternatively from about 0.01% to about 0.5%, alternatively from about 0.02% to about 0.25%, alternatively from about 0.03% to about 0.10%.

Non-limiting examples of warming sensates can include vanillyl alcohol n-butyl ether (sold as TK-1000 by Takasago International), Heatenol™ (available from Sensient Pharmaceutical, St. Louis, MO), Optaheat (sold by Symrise, Holzminden, Germany), ginger extract, *capsicum* tincture, cinnamon, capsaicin, curry, Isobutavan, Nonivamide, vanillyl butyl ether (commercially available as Hotact® VBE), piperine, and combinations thereof. Warming sensates can be present from about 0.005% to about 2%, by weight of the composition, alternatively from about 0.01% to about 1%, and alternatively from about 0.1% to about 0.5%.

Non-limiting examples of flavoring agents can include natural flavoring agents, artificial flavoring agents, artificial extracts, natural extracts and combination thereof. Non-limiting examples of flavoring agents can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, apricot, anethole, ginger, jack fruit, star fruit, blueberry, fruit punch, lemon grass, banana, strawberry banana, grape, blue raspberry, lemon lime, wintergreen mint, bubble gum, tart honey lemon, green apple, apple, tangerine, grapefruit, kiwi, pear, tangerine, tangerine lime, menthol, and combinations thereof. Flavoring agents can be present from about 0.05% to about 10%, by weight of the composition, alternatively from about 0.1% to about 8%, alternatively from about 0.2% to about 6%, alternatively from about 0.4% to about 3%, alternatively from about 0.6% to about 1.5%.

Also described herein is a kit comprising the personal health care composition described herein. In one aspect, the kit can comprise a delivery device and the personal health care composition contained in the delivery device. In one aspect, the kit can optionally comprise at least one additional component, such as a supplement or a vitamin composition.

Also described herein is a method of providing one or more health benefits comprising administering a personal health care composition as described herein comprising an aptamer to a subject in need thereof, wherein the aptamer has a binding affinity for ICAM-1. Non-limiting examples of the one or more health benefits can include providing a physical barrier to block rhinovirus binding and entering cells, helping to stop a cold caused by rhinovirus from forming, reducing the severity and/or duration of a cold caused by rhinovirus, reducing the chances of getting a cold, and combinations thereof.

EXAMPLES

The following examples illustrate non-limiting examples of the invention described herein. The exemplified personal health care compositions can be prepared by conventional formulation and mixing techniques. It will be appreciated that other modifications of the personal health care compositions within the skill of those in the formulation art can be undertaken without departing from the spirit and scope of this invention.

The following are non-limiting examples of personal health care compositions described herein.

Oral Composition Examples

Throat Spray

|  | Ex. 1 (Wt %) | Ex. 2 (Wt %) |
| --- | --- | --- |
| Benzocaine | 5.0 | 0 |
| Menthol | 1.0 | 1.0 |
| Glycerin | 17.0 | 17.0 |
| Flavoring system | 0.15 | 0.15 |
| Propylene Glycol | 65.0 | 65.0 |
| Ethyl Alcohol 95% | 7.99 | 7.99 |
| Saccharin Sodium | 0.13 | 0.13 |
| Sucralose | 0.18 | 0.18 |
| Color | 0.005 | 0.005 |
| Aptamer | 0.001-1.0 | 0.001-1.0 |
| Water | Q.S. | Q.S. |

Orally Dissolving Tablet Formula

| | Ex. 3 (Wt %) | Ex. 4 (Wt %) | Ex. 5 (Wt %) | Ex. 6 (Wt %) | Ex. 7 (Wt %) |
|---|---|---|---|---|---|
| Mannitol | 59.5 | 49.5 | 39.5 | 39.5 | 39.5 |
| Sucrose | 4.0 | 4.0 | 4.0 | 4.0 | 4.0 |
| Crospovidone | 4.0 | 4.0 | 4.0 | 4.0 | 4.0 |
| ProSolv ® SMCC 90 | Q.S. | Q.S. | Q.S. | Q.S. | Q.S. |
| Diphenhydramine HCl (Active) | 0 | 12.5 | 12.5 | 12.5 | 12.5 |
| Sodium Caprate | 0 | 0 | 0 | 1.0 | 0 |
| Cetylpyridinium Chloride | 0 | 0 | 0 | 0 | 1.0 |
| Magnesium Stearate | 1.0 | 1.0 | 1.0 | 1.0 | 1.0 |
| Aptamer | 0.001-1.0 | 0.001-1.0 | 0.001-1.0 | 0.001-1.0 | 0.001-1.0 |

Liquid Composition

| | Ex. 8 (Wt %) | Ex. 9 (Wt %) |
|---|---|---|
| Phenylephrine HCl | 0.031 | 0 |
| Acetaminophen | 2.01 | 0 |
| Dextromethorphan | 0.06 | 0 |
| Guaifenesin | 1.24 | 0 |
| Propylene glycol | 23.02 | 23.02 |
| Glycerin Solution (96%) | 8.00 | 8.00 |
| Sorbitol Solution (70%) | 13.15 | 13.15 |
| Xanthan gum | 0.15 | 0.15 |
| Sodium citrate dihydrate | 0.20 | 0.20 |
| Citric acid USP | 0.22 | 0.22 |
| Sodium benzoate | 0.10 | 0.10 |
| Saccharin sodium | 0.20 | 0.20 |
| Sucralose | 0.20 | 0.20 |
| Flavor | 0.001-0.6 | 0.001-0.6 |
| Color | 0.02 | 0.02 |
| Water | Q.S. | Q.S. |
| Aptamer | 0.001-1.0 | 0.001-1.0 |

Throat Lozenge Composition

| | Ex. 10 (Wt %) |
|---|---|
| Menthol | 0.2882 |
| Color | 0.1 |
| Ascorbic Acid | 0.26 |
| Sucrose | Q.S. |
| Liquid Glucose | 33.26 |
| Flavor | 0-0.6 |
| Aptamer | 0.001-1.0 |

Nasal Compositions

Saline Nasal Spray Composition

| | Ex. 11 (Wt %) |
|---|---|
| Water | Q.S. |
| Sodium Chloride | 2.0 |
| Aloe | 0-1.0 |
| Sodium Bicarbonate | 0-2.0 |
| Eucalyptus Oil | 0-0.3 |
| Aptamer | 0.001-1.0 |

Nasal Spray Compositions

| Ingredient | Ex. 12 (Wt %) | Ex. 13 (Wt %) |
|---|---|---|
| Water | Q.S. | Q.S. |
| Avicel ™ 591 | 3 | 3 |
| Polyvinylpyrrolidone | 3 | 3 |
| Carbowax ™ PEG 1450 | 5 | 5 |
| Sodium phosphate, dibasic | 0.0975 | 0.0975 |
| Sodium phosphate, monobasic | 0.5525 | 0.5525 |
| Levomenthol | 0.027 | 0.027 |
| Eucalyptol | 0.009 | 0.009 |
| Camphor | 0.009 | 0.009 |
| Benzalkonium Chloride 50% Solution | 0.1471 | 0.1471 |
| Benzyl Alcohol | 0.35 | 0.35 |
| Disodium EDTA | 0.03 | 0.03 |
| Oxymetazoline HCl | 0.05 | 0 |
| Aptamer | 0.001-1.0 | 0.001-1.0 |

Additional Nasal Spray Compositions

| | Ex. 14 (Wt %) | Ex. 15 (Wt %) | Ex. 16 (Wt %) |
|---|---|---|---|
| Pyroglutamic Acid | 0.35 | 0.70 | 1.00 |
| Succinic Acid | 1.00 | 0.70 | 0.35 |
| Zinc Acetate Dihydrate | 0.12 | 0.012 | 0.12 |
| Polysorbate 80 | 0.05 | 0.05 | 0.05 |
| Carbopol 980 | — | — | 1.20 |
| Hydroxypropyl methyl cellulose | 1.20 | — | — |
| Poloxamer 407 | — | 15.8 | — |
| Sodium Saccharin | — | 0.025 | 0.025 |
| Sucralose | 0.025 | — | — |
| Phenyl ethyl alcohol | 0.37 | 0.37 | 0.35 |
| Sodium chloride | 0.20 | 0.20 | 0.50 |
| Camphor | — | 0.03 | — |
| Menthol | 0.02 | 0.06 | 0.02 |

-continued

|  | Ex. 14 (Wt %) | Ex. 15 (Wt %) | Ex. 16 (Wt %) |
|---|---|---|---|
| Eucalyptol | — | 0.02 | — |
| Aromatic System | 0.05 | 0.38 | 0.05 |
| Sodium Hydroxide (30%) | — | — | 0.10 |
| Disodium succinate | 1.00 | 0.50 | — |
| Water | Q.S. | Q.S. | Q.S. |
| Aptamer | 0.001-1.0 | 0.001-1.0 | 0.001-1.0 |

V. EXAMPLES

Example 1. Aptamer Selection and Next Generation Sequence Characterization

A. Selection Strategy

One objective of this invention was to develop aptamers that would not just specifically bind to ICAM-1 receptors but would do so in a way that would block or inhibit the binding of virus particles to the receptor protein. The selection of aptamers against the extracellular domain of the ICAM-1 receptor alone would not necessarily be sufficient to block virus binding to the same protein as aptamers are relatively small and their blocking footprint will be limited to the epitopes that they bind to. If the epitopes that the aptamer binds to are not involved in virus binding to the ICAM-1 receptor, they will not inhibit binding of the virus particles.

This objective was consciously incorporated into the selection strategy, first by including several rounds of positive selection against the exo-cellular domain of the ICAM-1 protein (SEQ ID NO: 214); secondly, by imposing a double positive selection such that aptamers would be enriched for binding to the ICAM-1 extra-cellular domain in the context of nasal cells; thirdly, by imposing counter selection against HEK293 cells that carry similar receptor proteins (ICAM-3 and ICAM-5); and fourthly, by performing selection channels against specific desirable and undesirable aptamer binding outcomes including, specific elution of bound aptamers from nasal cells with the addition of rhinovirus particles, blocking of aptamer binding to ICAM-1 cells by the pre-application of rhinovirus particles, positive selection against HEK293 cells, positive selection against the extra-cellular domain of ICAM-1, and double positive selection against the extra-cellular domain of ICAM-1 and nasal cells.

Double positive selection (extra-cellular domain of ICAM-1 and nasal cells) ensures that enriched aptamers are favored that bind to the ICAM-1 receptor as it is presented on nasal cells. If selection was only performed against the extra-cellular domain of ICAM-1, it is possible that epitopes would be present that are not present in vivo. If selection was only performed against nasal cells, it is possible that aptamers would be enriched for binding targets other than ICAM-1 on the surface of such cells.

The counter selection against HEK293 cells was implemented to drive enrichment of aptamers that bound to the N-terminus of the ICAM-1 extracellular domain. HEK293 cells express other members of the ICAM receptor family, ICAM-3 and ICAM-5. These receptor proteins differ in their extracellular domain from ICAM-1 predominantly at their N-terminus. The N-terminus of the ICAM-1 receptor is the region of the extra-cellular domain that rhinovirus particles bind to. Thus, this counter selection step was included to drive aptamer selection towards those aptamers that will block or inhibit rhinovirus binding to nasal cells.

Finally, once the aptamer library was enriched with double positive selection against the extra-cellular domain of ICAM-1 and nasal cells, and counter selection against HEK293 cells, the enriched library was separated into aliquots and applied to several different targets, including continued double positive selection, positive selection against HEK293 cells, positive selection against the extra-cellular domain alone, selection based on rhinovirus particle elution of aptamers bound to nasal cells, and selection based on blocking aptamer binding to nasal cells through pre-treatment with rhinovirus particles.

Each of these selected libraries was characterized by next generation sequencing. Aptamers that exhibit higher levels of enrichment against the double positive selection, the extracellular domain selection, and either of the rhinovirus particle enabled selection processes and lower enrichment against HEK293 alone would be desirable sequences for the blocking or inhibition of rhinovirus binding to nasal cells.

B. Growth of Human Cells

B.1. Human Nasal Epithelial Cells Growth Conditions

Primary human nasal epithelial cells (HNepC; PromoCell, Catalog #C-21060) were grown in airway epithelial cell growth medium (PromoCell, Catalog #C-21160) at 37° C. and 5% $CO_2$.

B.2. Growth of HEK293 Cells

HEK293 cells purchased from ATCC (CRL-1573) were grown in Eagle's Minimum Essential Medium (EMEM)+ 10% Fetal Bovine Serum (FBS) at 37° C. and 5% $CO_2$.

B.3. Human Rhinovirus A16 Suspension

UV inactivated HRV16 virus particles were purchased (Zeptometrix Corporation) and stored at −80° C. until use. The concentration of the virus particles (VPs) was calculated to be 98,700 vp/mL.

C. Aptamer Selection

C.1. Library Preparation

In the first step, a DNA library of about $10^{15}$ different sequences (TriLink BioTechnologies), containing a random region of 40 nucleotides flanked by two conserved regions, forward primer recognition sequence (5'-GGGTG-CATCGTTTACGC-3'; SEQ ID No 224) and a 3' reverse primer recognition sequence (5'-CTGCTGCTGAG-GAAGGATATGAG-3' SEQ ID No 225) (see FIG. 1), was transcribed to RNA using a mixture of 2'-fluoro pyrimidines nucleotides (2F-UTP and 2F-CTP) and natural purine nucleotides.

In brief, about 1.66 nmoles of single stranded DNA were amplified in 390×50 µL PCR reactions for 4 cycles using the primers Lib7_T7 Fwd primer (sequence: 5'-TAATACGACTCACTATAGGGTGCATCGTTTACGC-3', (SEQ ID No 226) with transcription starting at the first G underlined) and Lib7_Rvs primer (sequence 5'-CT-CATATCCTTCCTCAGCAGCAG-3' SEQ ID No 227). The amplified DNA was purified using the Genejet PCR purification kit (Fisher Scientific, Catalog #K0701). This amplification of the ssDNA library created a dsDNA library with a T7 promoter, which was used as a templated to generate a modified RNA library for selection.

Post DNA amplification, 52 µg of purified dsDNA was transcribed in 26×20 µL transcription reactions by using a mutant T7 polymerase (T7 R&DNA polymerase, Lucigen, Catalog #D7P9205K) polymerase and a mixture of rATP, rGTP and the modified nucleotides 2F-UTP and 2F-CTP. The NTPs were mixed together at a ratio of 3:1 modified to non-modified. Each reaction mixture contained 4 µL 5×T7 R&D polymerase, 1 µL NTP 3:1 mix, 2 µL DTT (0.1M), 0.7 µL T7 R&D polymerase, 1.2 µL inorganic pyrophosphatase, 0.5 μL Rnase inhibitor, and 10.6 μL DNA template. The reactions were incubated at 37° C. for 16 hours.

The transcribed library was subjected to Dnase treatment by setting up reaction mixtures consisting of 10 μL 10× Dnase buffer, 4 μL Dnase I, 66 μL Rnase free water, and 20 μL transcription reaction. The reaction mixtures were then incubated at 37° C. for 30 min, 1 μL of 0.5 M EDTA was added and mixed, further incubated at 75° C. for 10 minutes and purified using Monarch RNA cleanup kit (New England Biolabs, Catalog #T2040L).

C.2. Immobilization of ICAM-1 onto his-Pur Ni-NTA Resin

Lyophilized ICAM-1 protein (50 μg Ray-Biotech, Catalog #: 228-21751-2) with a His-tag on the C-terminus region was resuspended in 100 μL of sH$_2$O (final concentration of 0.5 μg/μL or 9.88 μM). The solution was aliquoted and stored at −20° C. until use. The protein sequence was:

(SEQ ID No 228)
QTSVSPSKVILPRGGSVLVTCSTSCDQPKLLGIETPLPKKELL

LPGNNRKVYELSNVQEDSQPMCYSNCPDGQSTAKTFLTVYWTP

ERVELAPLPSWQPVGKNLTLRCQVEGGAPRANLTVVLLRGEKE

LKREPAVGEPAEVTTTVLVRRDHHGANFSCRTELDLRPQGLEL

FENTSAPYQLQTFVLPATPPQLVSPRVLEVDTQGTVVCSLDGL

FPVSEAQVHLALGDQRLNPTVTYGNDSFSAKASVSVTAEDEGT

QRLTCAVILGNQSQETLQTVTIYSFPAPNVILTKPEVSEGTEV

TVKCEAHPRAKVTLNGVPAQPLGPRAQLLLKATPEDNGRSFSC

SATLEVAGQLIHKNQTRELRVLYGPRLDERDCPGNWTWPENSQ

QTPMCQAWGNPLPELKCLKDGTFPLPIGESVTVTRDLEGTYLC

RARSTQGEVTRKVTVNVLSPRYEVDHHHHHH.

An aliquot of His-Pur Ni-NTA (Fisher Scientific, Catalog #PI88221) resin was transferred to a 0.6 mL tube and centrifuged at 700×g for 2 minutes. The supernatant was removed, and the resin was washed 3 times with 500 μL of PBS buffer (pH 7.4). Then, aliquots of ICAM-1 protein in 1×PBS buffer (pH 7.4) were incubated with the His-Pur Ni-NTA resin overnight at 4° C. while mixing. For selection round 1, 300 pmoles of ICAM-1 protein was immobilized onto 50 μL of resin. For subsequent rounds, 50 pmoles of ICAM-1 protein was immobilized onto 25 μL of resin. After protein immobilization, the resin was transferred to a 1 mL cartridge with a frit filter and washed with 2 mL of 1×PBS buffer. Finally, aliquots of 0.5-1 mM imidazole in 1×PBS buffer were added and incubated with the resin for 30 minutes at 4° C. to block unreacted binding sites on the resin. The resin was washed three times with 1 mL aliquots of 1×PBS buffer.

For negative selections with imidazole blocked resin, aliquots of the His-Pur Ni-NTA resin were incubated with an appropriate concentration of imidazole in 1×PBS buffer for 30 minutes to block unreacted binding sites on the resin, followed by washing with 1× selection buffer. The selection buffer used for all the examples in this application was Dulbecco's PBS buffer supplemented with calcium chloride (CaCl2, 0.9 mM), magnesium chloride (MgCl2 0.49 mM), potassium chloride (KCl, 2.67 mM), potassium phosphate monobasic (KH2PO4, 1.47 mM), sodium chloride (NaCl, 137.93 mM), and sodium phosphate dibasic (Na2HPO4, 8.06 mM).

C.3. Aptamer Selection Overview

Figure 2:
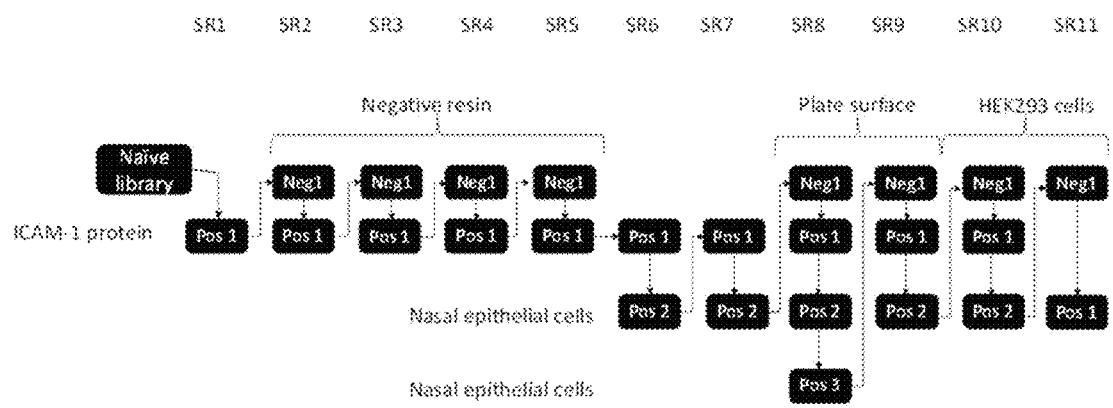
FIG. 2 illustrates the aptamer selection strategy during selection rounds 1 to 11.

The aptamer selection was performed in fourteen selection rounds ("SR"), which are illustrated in FIG. 2. The selection rounds 1 to 5 enrich the sequences in the aptamer library that bind to ICAM-1 immobilized onto the Ni-NTA Resin. In selection rounds 6 to 9, the aptamer library was subjected to the same ICAM-1 immobilized Ni-NTA Resin procedure and the eluted aptamers were further enriched towards sequences that bind to human nasal epithelial cells (HNepC), this is referred to as double positive selection. In selection rounds 10 to 11, counter selection against HEK293 cells and positive selections against HNepC were performed. Selection rounds 12 to 14, illustrated in FIG. 3, break out to different selection conditions and are referred to as splits. Five different splits were performed: split A: nasal epithelial cells, split B: HEK293 cells, split C: ICAM-1 protein, split D: human rhinovirus A16 (HRV16) elution, and split E: HRV16 blocking.

C.4. Aptamer Selection Process

C.4.1 Selection Round 1

The aptamer selection round 1 was completed by performing a positive selection against ICAM-1 immobilized Ni-NTA resin. The RNA library (produced as described in section C.1) was heated to 45° C. for 10 minutes and allowed to cool to room temperature for 10 minutes. Then, the prepared aptamer library was added to 300 pmol of the ICAM-1 immobilized on Ni-NTA resin (prepared as described in section C.2) and incubated with rotation at room temperature for 30 minutes. Unbound RNA was washed off the resin with 500 μL of selection buffer (pH 7.4).

The bound RNA was then eluted twice by adding aliquots of 200 μL of 6 M urea to the resin and incubating the suspension at 85° C. for 5 minutes. The recovered RNA library was collected and purified using Monarch RNA cleanup kit.

The collected aptamer library was reverse transcribed following the Protoscript II Reverse Transcriptase manufacturer's protocol. The number of reverse transcription reactions varied depending on the amount of RNA going into that specific round of selection.

Then, the reverse transcribed aptamer library was amplified by polymerase chain reaction (PCR) using a standard PCR protocol and the following amplification steps:

Step 1: 95° C.—5 minutes
Step 2: 95° C. —10 seconds
Step 3: 56° C.—15 seconds
Step 4: 72° C.—30 seconds
Repeat steps 2 to 4 for 4 cycles
Step 5: 95° C.—10 seconds
Step 6: 59° C.—15 seconds
Step 7: 72° C.—30 seconds
Repeat steps 5 to 7 for up to 26 cycles.

The PCR amplified dsDNA aptamer library was then transcribed back into RNA and subjected to Dnase treatment using the protocols described in section C.1.

C.4.2 Selection Rounds 2 to 5

Selection rounds 2 to 5 incorporate two selection strategies: negative selection against imidazole blocked Ni-NTA resin and positive selection with ICAM-1 immobilized Ni-NTA resin (see FIG. 2). The negative selection was performed to select aptamer sequences that do not bind to the imidazole blocked Ni-NTA resin (prepared as described in Section C.2). First, an aliquot of 50 μL of imidazole blocked resin was transferred to a 1 mL cartridge fitted with a 20 μm frit and washed twice with 1 mL aliquots of selection buffer. Then, the prepared RNA library from the previous selection round was heated to 45° C. for 10 minutes and allowed to cool to room temperature for 10 minutes. The RNA library was added to the cartridge and incubated at room temperature for 30 minutes with the imidazole blocked Ni-NTA resin. Following incubation, the flow through solution was collected. Then, the cartridge was washed using an aliquot of 500 µL of selection buffer and the solution was collected. The flow through solution and column wash collections were pooled together and purified with Monarch RNA cleanup kit following manufacture protocols.

The RNA library that was obtained from the negative selection was then subjected to the positive selection, which selects for sequences that bind to ICAM-1 immobilized Ni-NTA resin (prepared as described in Section C.2). In brief, the RNA library was heated to 45° C. for 10 minutes and allowed to cool to room temperature for 10 minutes. Then, the RNA library was added to 50 pmoles of the ICAM-1 immobilized on Ni-NTA resin (prepared as described in Section C.2) and incubated with rotation at room temperature for 30 minutes. Unbound RNA was washed off the resin with aliquots of 500 µL of selection buffer. The number of washes varied depending on the selection round and the number of positive selections completed and was pre-determined by selection modelling. Then, the bound RNA library was eluted twice by adding aliquots of 200 µL of 6 M urea to the resin and incubating the suspension at 85° C. for 5 minutes. The eluted RNA library was collected and purified with the Monarch RNA cleanup kit, followed by reverse transcription, PCR amplification, transcription, and DNAse treatment as described in sections C.1 and C.4.1.

C.4.3. Selection Rounds 6 to 9

The RNA aptamer library that was enriched from selection rounds 1 to 5 was further enriched in selection rounds 6 to 9, which utilizes two selection strategies: a positive selection with ICAM-1 immobilized Ni-NTA resin and another positive selection against human nasal epithelial cells (HNepC) that express the ICAM-1 receptor. This group of selection rounds is referred to as "double positive selection". In selection round 8, two positive selections against HNepC were performed (i.e. "triple positive selection").

In selection rounds 6 and 7, the RNA library was resuspended in 500 µL of 1× selection buffer. The first positive selection (selecting against ICAM-1 immobilized Ni-NTA resin) started by adding the resuspended RNA to the ICAM-1 immobilized on Ni-NTA resin, followed by incubation at 37° C. for 30 minutes. The unbound RNA was discarded and the resin was washed with aliquots of 500 µL of 1× selection buffer. For the elution step, an aliquot of 200 µL of 6 M urea was added to the resin and incubated at 85° C. for 5 minutes and the elution solution was collected. The elution step was repeated and the eluants were pooled together and cleaned up using a Monarch RNA clean up kit.

The second positive selection started by preparing the HNepC cells by aspirating the medium from the 6-well plate (~3 mL) where the cells were grown, followed by washing the cells three times with 3 mL of prewarmed 1× selection buffer. A solution of 1 mL of RNA library in 1× selection buffer was immediately applied to the washed cells and incubated for 30 minutes at 37° C. and 50 revolutions per minute (rpm). After the 30 minute incubation, the supernatant containing ~50% of the cells was collected, the cells were pelleted at 500×g for 2 minutes and washed twice with 200 µL prewarmed 1× selection buffer. The cell pellet was collected, and the bound RNA was eluted from the cells by the addition of 6 M urea, followed by incubation at 85° C. and RNA purification.

The adhered cells (i.e. remaining ~50% cells) were washed twice with 1 mL of preheated 1× selection buffer.

Then, an aliquot of 1 mL of 10 mM EDTA was added and allowed to incubate with the cells at 37° C. for 15 minutes at 50 rpm. The EDTA treated cells were pelleted at 500×g for 2 minutes. Then, an aliquot of 200 µL of 6 M urea was added to the pellet and the suspension was heated to 85° C. for 5 minutes, followed by centrifugation at 13,000 rpm to recover the RNA aptamers in the supernatant. The elution step was repeated one more time, the eluants were combined, and the RNA aptamers were purified. The reverse transcription, PCR amplification, and transcription following the protocol in sections C.1 and C.4.1 was performed on the purified samples.

In selection rounds 8 and 9, the EDTA lifting of the cells was removed from the protocol and the RNA bound to the cells was eluted using 6 M urea while they were still attached to the 6-well plate. Additionally, a negative selection step was included in both rounds to remove any RNA sequences that bind to the plastic of the 6-well culture plate. For the negative selection, the RNA library was resuspended in 1 mL of 1× selection buffer, followed by heating to 37° C. for at least 10 minutes. One well in a 6-well culture plate was pre-washed twice with 1 mL of 1× selection buffer. Then, the heated RNA library was added to the well and incubated at 37° C. and 50 rpm for 30 minutes. The solution in the well was collected and brought up to 1 mL volume with selection buffer. The resulting 1 mL solution of RNA library was incubated with HNepC, grown in a 6-well plate, at 37° C. at 50 rpm for 1 hour. The unbound RNA was removed from the cells and the cells were washed twice with 1 mL of 1× selection buffer (prewarmed to 37° C.). The bound RNA was eluted by adding 1 mL of 6 M urea and incubating the cells at 85° C. for 5 minutes. The elution step was repeated. The eluants were pooled together and the RNA was purified using the Monarch RNA clean up kit. The selected RNA was reverse transcribed, PCR amplified, transcribed and DNAse treated as previously described.

C.4.4. Selection Rounds 10 and 11

In selection rounds 10 and 11, a negative selection against HEK293 cells was introduced (see FIG. 2). HEK293 cells do not express the ICAM-1 receptor, which allows for the counterselection of sequences that bind elsewhere on the cell surface that is not ICAM-1.

The HEK293 cells were grown in a 6-well culture plate and were used at 80% confluency or greater. The cells were prepared by removing and discarding all media from the well and by washing the cells three times with 3 mL of pre-warmed 1× selection buffer. Then, the prepared RNA library was added to the cells and the library and cell solution were incubated for 1 hour at 37° C. with gentle shaking (50 rpm). After incubation, the supernatant with the unbound RNA library was removed and collected. Then, the cells were washed with 1 mL of pre-warmed 1× selection buffer and the solution was also collected. The collected RNA solutions were combined and purified with a Monarch RNA Cleanup Kit. This purified RNA library was then subjected to a positive selection round against HNepC, following the same protocol as described on selection rounds 8 and 9 (see section C.4.3). Two positive selections were performed in selection round 10, while a single positive selection was completed in selection round 11.

C.4.5. Selection Rounds 12 to 14: Nasal Epithelial Cell Split

In the nasal epithelial cell split of selection rounds 12 to 14 (see FIG. 3), the RNA library collected from selection round 11 was further subjected to the negative selection against the HEK293 cells followed by the positive selection with the HNepC, using the protocol described in section C.4.4.

C.4.6. Selection Rounds 12 to 14: HEK293 Cell Split

In the HEK293 cell split of selection rounds 12 to 14 (see FIG. 3), the RNA library collected from selection round 11 was enriched towards sequences that bind to HEK293 cells. The protocol for this selection round followed the procedure of selection rounds 10 to 11 described in section C.4.4, excluding the selection with the HNepC.

C.4.7. Selection Rounds 12 to 14: ICAM-1 Protein Split

In the ICAM-1 split of selection rounds 12 to 14 (see FIG. 3), the RNA library collected from selection round 11 was enriched towards sequences that bind to ICAM-1 immobilized onto the Ni-NTA Resin. The protocol for this selection round followed the procedure of selection round 1 described in sections C.1 and C.4.1.

C.4.8. Selection Rounds 12 to 13: Human Rhinovirus A16 (HRV16) Elution Split

Figure 3:
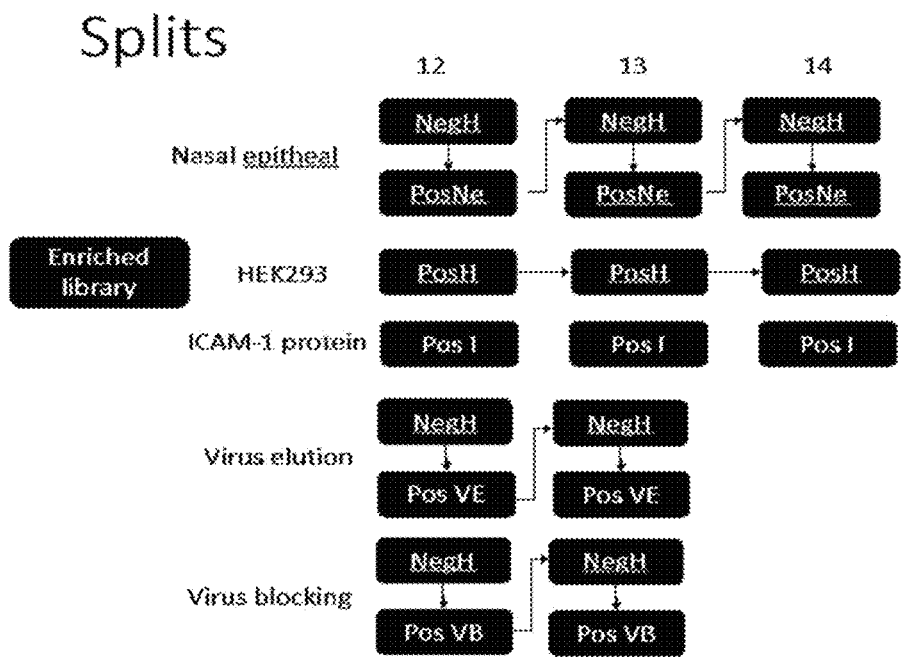
FIG. 3 shows a schematic of the aptamer splits selection strategy during selection rounds 12 to 14.

The HRV16 elution split only occurred during selection rounds 12 and 13 (see FIG. 3). The RNA library collected in selection round 11 was further enriched by a negative selection against HEK293 cells followed by a positive selection on HNepC using Human Rhinovirus A16 (HRV16) particles to elute the aptamer library. The negative selection on HEK293 cells followed the same protocol of selection rounds 10 and 11 described in section C.4.4 but excluding the selection against the HNepC.

Following the negative selection with the HEK293 cells, the collected RNA was diluted in 1× selection buffer and heated to 37° C. for 15 minutes. The HNepC cells were washed three times with 1 mL of prewarmed selection buffer and the heated RNA library was added to the cells and incubated for 1 hour at 37° C. and 50 rpm. After incubation, the unbound RNA was removed and discarded. The recovered cells were washed ten times with 1 mL of preheated 1× selection buffer. Then, a suspension of 50% (v/v) virus particles (VPs) (see Section B.3) in 1× selection buffer were mixed with the cells and incubated for 1 hour at 37° C. with 50 rpm mixing. The supernatant was collected, and the RNA was purified and reverse transcribed following the protocol described in sections C.1 and C.4.1.

C.4.9. Selection Rounds 12 and 13: HRV16 Blocking Split

The HRV16 blocking split was performed during selection rounds 12 and 13 (see FIG. 3). The RNA library of selection round 11 was further enriched by a negative selection against HEK293 cells followed by a positive selection on HNepC with HRV16 bound to the ICAM-1 receptor before exposing the cells to the RNA library. The HEK293 negative selection followed the same protocol of selection rounds 10 and 11 described in section C.4.4, excluding the selection with the HNepC.

Following the negative selection on the HEK293 cells, a suspension of 50% (v/v) virus particles (VPs) in 1× selection buffer was prepared. Then, the suspension was heated to 37° C. for 15 minutes and mixed with prewashed HNepC cells, followed by incubation for 1 hour at 37° C. and 50 rpm. After incubation, all unbound VPs were removed and discarded. Then, the RNA library recovered from the negative selection was resuspended in 1× selection buffer, added to the cells, and incubated at 37° C. for 1 hour. The supernatant containing the unbound RNA was collected, purified and reverse transcribed following the protocols described in sections C.1 and C.4.1.

D. Aptamers Sequencing

After 14 selection rounds, the aptamer libraries were sequenced. In summary, the selection libraries from rounds 10 to 14 were prepared for next generation sequencing (NGS) through a two-step PCR process. In the first step, a different hex code (6 base sequence) and a portion of a universal sequencing primer was added to the 5' end of each aptamer library. In the second step, complete universal sequencing primers were added to both ends. After the second PCR step, the libraries were purified through acrylamide electrophoresis and balanced for relative quantity. These libraries were then pooled and sent to the Hospital for Sick Children in Toronto for NGS with an Illumina HiSeq 2500 instrument.

The sequencing data was tabulated and analyzed. A total of 16,116,086 sequences were analyzed and each library contained more than 200,000 sequences. The sequences from selection round 14 (nasal epithelial cell split) were sorted by copy number and named in descending order with the highest copy number sequence being named Nas.R-1. These top sequences are listed in Table 3.

Figure 4:
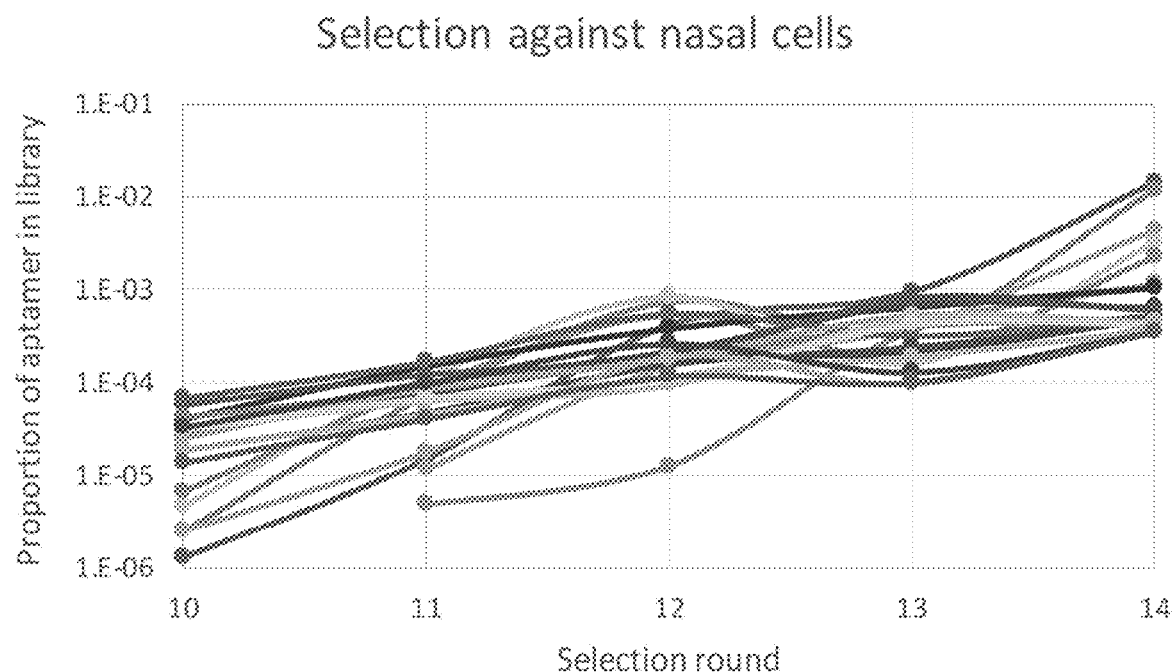
FIG. 4 illustrates the enrichment trajectories for the top twenty aptamers.

The copy numbers of the top sequences of selection round 14 were determined on the libraries obtained from the other selection rounds. Finally, the frequency was computed for each sequence by dividing observed copy number by the total number of sequences observed in the particular selection library. Enrichment trajectories of the top 20 sequences in terms of frequency across different selection rounds were plotted (see FIG. 4). During the selection, these sequences were enriching at a similar rate.

Example 2. Aptamer Binding Specificity

It was desired to identify aptamer sequences that bind specifically to the ICAM-1 receptor and block the ability of the rhinovirus from infecting human nasal epithelial cells. The previous section, Example 1, detailed the protocol on the selection process of determining sequences that enriched in the presence ICAM-1. This section will highlight the protocols that were used to determine the sequences discovered in Example 1 that have the highest affinity and specificity towards the ICAM-1 receptor target.

Multiple strategies were implemented to determine the top sequences from selection process for RNA aptamers that bind specifically and with high affinity towards human epithelial cells (HNepC), but not towards HEK293 cells that do not express the ICAM-1 target. The first protocol included exposing HNepC and HEK293 cells to some of the selected aptamer sequences, followed by incubation, elution, and quantification of the concentration of aptamers that bound to each cell type. Another strategy implemented included the visualization and identification of fluorescently labeled RNA aptamers that bind to HNepC, but do not visually bind to HEK293 cells. A final strategy included immobilizing the top RNA aptamer sequences, followed by flowing the exo-cellular domain of the ICAM-1 protein and other various proteins across the aptamer and using plasmon resonance to determine binding affinity. The following section describes in detail the strategies that are summarized above.

A. Detecting Binding Specificity and Affinity Via qPCR

A.1. Synthesis of Aptamer RNA Sequences

DNA oligos that corresponded to the RNA aptamer sense and antisense sequences plus the T7 RNA polymerase promoter were purchased (Integrated DNA Technologies). Each of the oligos were mixed at equimolar concentrations in 10 mM Tris buffer (pH 8.3) containing 50 mM KCl and 1.5 mM MgCl2, followed by incubation at 95° C. for 5 minutes. Then, the modified RNA aptamers were synthesized by transcription of the dsDNA template, followed by DNAse treatment, and purification as described in Example 1 Sections C.1 and C.4.1.

A.2. RNA Aptamers, HNepC and Hek293 Cell Preparation

The modified RNA aptamers were dissolved at a concentration of 28.2 nM in 1× selection buffer. HNepC or HEK293 cells were grown in a well of a 24-well plate at densities ranging from 70-75% (HNepC) or 90-95% (HEK293 cells) following the protocol outlined in Example 1 Sections B.1 and B.2.

A.3. qPCR Analysis Procedure

For each sample, two 20 µL qPCR reactions were prepared using the Luna qPCR universal mastermix (New England Biolabs, Catalog #M3003L), 0.2 µM of each primer (forward primer: 5'-TAATACGACTCACTATAGGGTG-CATCGTTTACGC-3' (SEQ ID No 226), reverse primer: 5'-CTCATATCCTTCCTCAGCAGCAG-3" (SEQ ID No 227)), and 5 µL of the cDNA sample. qPCR reactions containing known amounts of the sense DNA template were also prepared. The PCR reactions were performed using the following conditions:

Step 1: 95° C. for 3 minutes
Step 2: 95° C. for 15 seconds
Step 3: 56° C. for 15 seconds
Step 4: 60° C. for 30 seconds
Steps 2 to 4 were repeated for 40 cycles.

The Ct values of the binding assay samples were compared to the Ct values of the known amounts of DNA samples to determine the amount of RNA that bound to the cells.

A.4. Human Nasal Epithelial and HEK293 Aptamer Binding Assay

Six of the top aptamer sequences (Nas.R-1, Nas.R-2, Nas.R-4, Nas.R-5, Nas.R-7 and Nas.R-8) that were identified in the selection process (Example 1) were tested for their binding specificity and affinity towards HNepC or HEK293 cells. The RNA aptamers, HNepC, and HEK293 cells were prepared as described in Section A.2.

Figure 5:
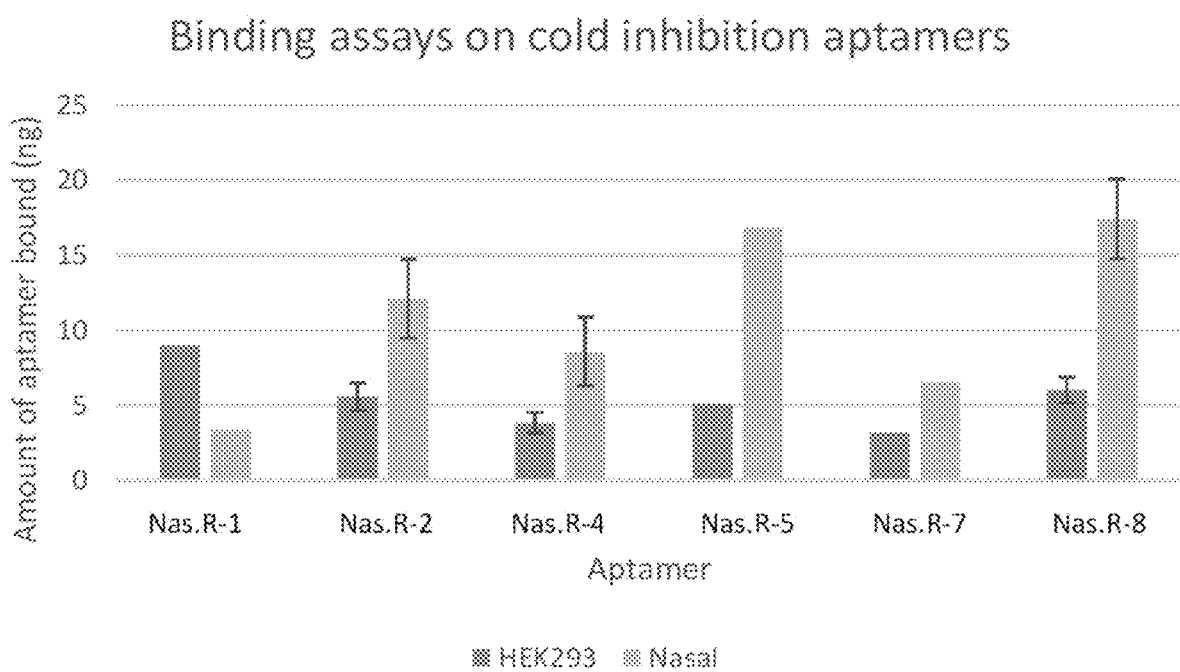
FIG. 5 illustrates the binding assay results of selected aptamers on HNepC and HEK293 cells.

The aptamers were incubated with the HNepC for 1 hour at 37° C. and 5% CO2 with gentle shaking every 15 minutes. The unbound RNA was removed and the cells were washed four times with 150 µL of 1× selection buffer prewarmed at 37° C. To elute the bound RNA aptamers, aliquots of 200 µL of 6 M urea were added to the cells, followed by incubation at 85° C. for 5 minutes. The elution step was repeated, the eluants were combined, and the RNA aptamers were purified using a Monarch RNA clean up kit following the manufacture's protocol. Each RNA sample was reverse transcribed in a 20 µL M-MµLV (New England Biolabs, M0253L) reverse transcriptase reaction following the manufacturer's protocol. The reverse transcribed sequences were quantified using qPCR analysis following the protocol described in section A.3. The same procedure was followed for the HEK293 cells. The results are illustrated in FIG. 5. For aptamers Nas.R-2, Nas.R-4, Nas.R-5, Nas.R-7, and Nas.R-8, the binding affinity towards HNepC was higher than for HEK293 cells.

B.1. Visualizing Aptamer Bound to ICAM-1 on HNepC and HEK293 by Fluorescence

B.1.1. Preparation of Fluorescently Tagged RNA Aptamers

Modified RNA aptamer Nas.R-4 with a spacer (AAACAAACAAAC; SEQ ID No. 235) and a sense binding sequence (GUAUGGCGGUCUCCAACAGG; SEQ ID No 236)

at the 3' end was synthesized, as previously described in section A.1.

(SEQ ID No 229)
5'-GGGUGCAUCGUUUACGCGCAACAUAAA

AAUUUAAAGUGCUCAGUUGUCAAUCUAUG

ACUGCUGCUGAGGAAGGAUAUGAG AAAC

AAACAAAC GUAUGGCGGUCUCCAACAGG-3'

The sense binding sequence was added to anneal to a 6-FAM labelled fluorescent antisense oligonucleotide. Before each binding assay, the NAS-FAM antisense oligo (5' 6-FAM/CCTGTT GGAGACCGCCATAC-3' (SEQ ID No 230)) was mixed with the modified RNA aptamer at equimolar concentrations in 1× selection buffer, followed by incubation at 37° C. for 15 minutes.

B.1.2. HNepC and Hek293 Cell Preparation

HNepC and HEK293 cells were prepared following the procedure outlined in Section A.2 but were seeded at densities of about 50% one to two days before the assay, onto 12 mm glass coverslips (Fisher Scientific, Catalog #12-545-82) submersed in medium in wells of 24-well plates.

B.1.3. Binding of the Fluorescently Labelled Aptamers to Cells

Figure 6A:
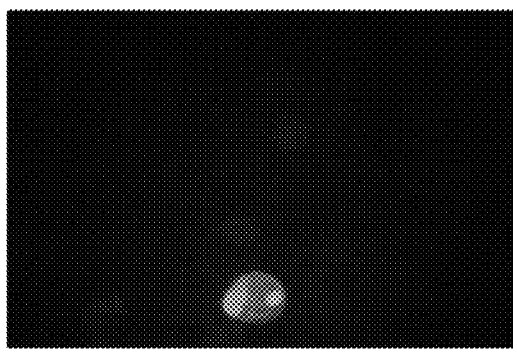
FIG. 6A shows the fluorescence image and FIG. 6B shows the brightfield image of the HNepC cells.
Figure 6B:
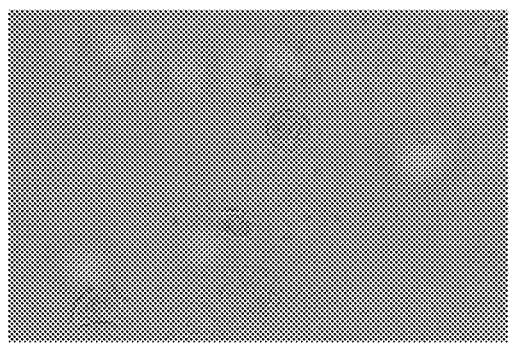
Figure 6C:
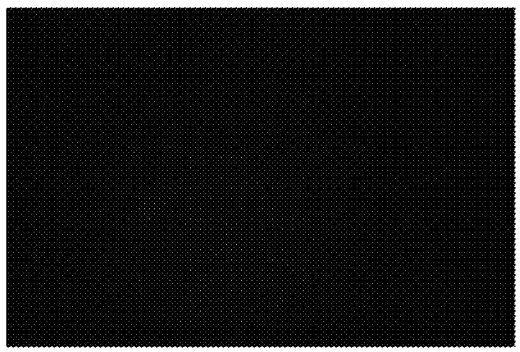
FIG. 6C shows the fluorescence image and FIG. 6D shows the brightfield image of the HEK293 cells.
Figure 6D:
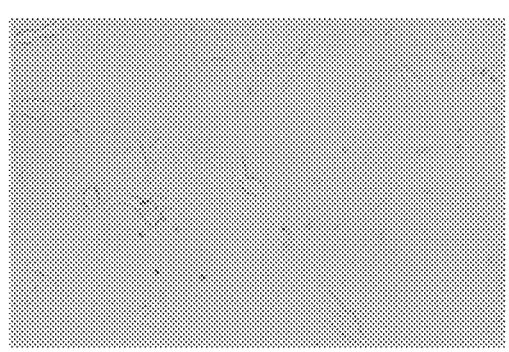
Figure 7A:
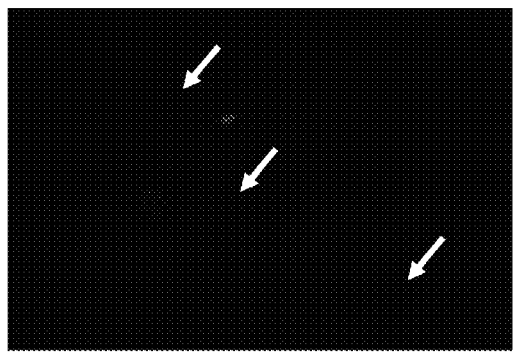
FIG. 7A shows the fluorescence image and FIG. 7B shows the brightfield image using the Nas.R-2 aptamer.
Figure 7B:
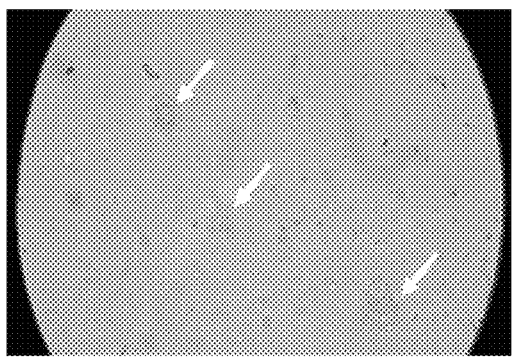
Figure 7C:
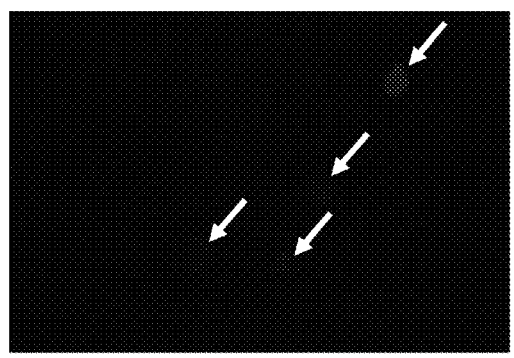
FIG. 7C shows the fluorescence image and FIG. 7D shows the brightfield image using the Nas.R-8 aptamer.
Figure 7D:
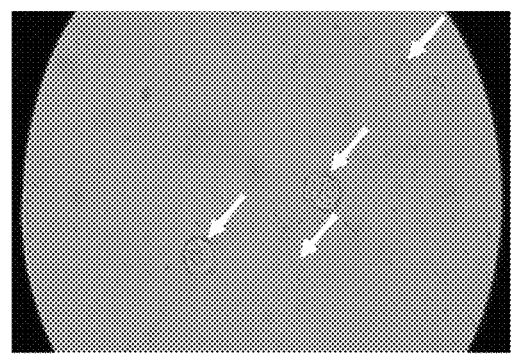
Figure 7E:
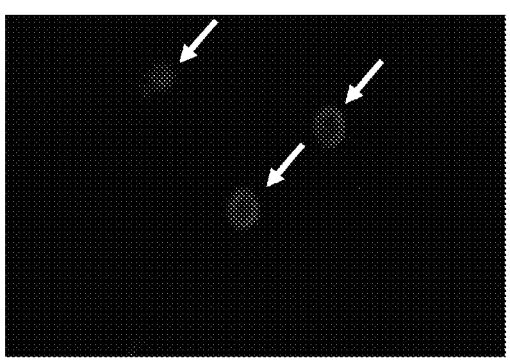
FIG. 7E shows the fluorescence image and FIG. 7F shows the brightfield image using the control aptamer.
Figure 7F:
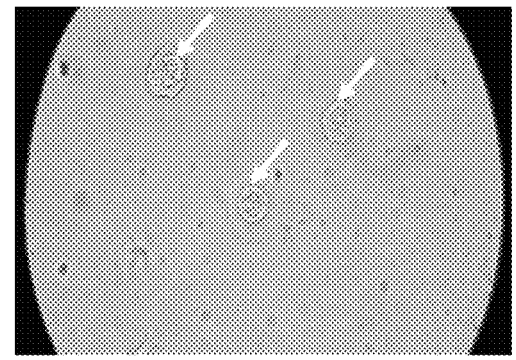
Figure 7G:
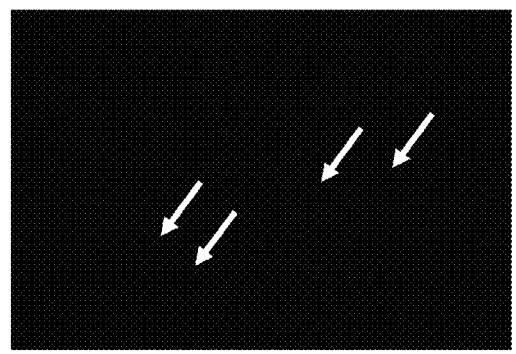
FIG. 7G shows the fluorescence image and FIG. 7H shows the brightfield image of cells only.
Figure 7H:
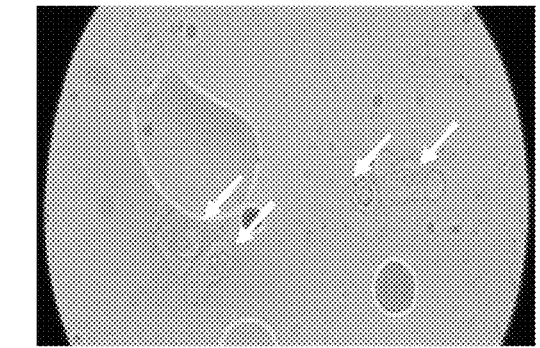

The medium was aspirated from the HNepC culture. Then, an aliquot of 150 µL of the aptamer/NAS-FAM antisense mixture, prepared as described in Section B.1, was applied to the cells, followed by incubation for 15 minutes at 37° C. and 5% $CO_2$ and with gentle agitation every 5 minutes. The unbound RNA aptamer was aspirated and the HNepC were washed three times with 150 µL of 1× selection buffer prewarmed at 37° C. The coverslip was removed and submersed into a drop of selection buffer on a glass microscope slide. Fluorescence of the cells was monitored for up to about 1 hour using a Nikon inverted fluorescent microscope and a FITC fluorescence filter. Images (see FIG. 6) were taken using a Nikon D7500 camera at 1/30 sec exposure. The same process was followed using HEK293 cells (see FIGS. 6C and 6D). As illustrated in FIGS. 6A and 6B, significant fluorescence was observed when the labelled aptamers were incubated with HNepC, while no fluorescence was detected with HEK293 cells, confirming the stronger binding affinity of the aptamers towards surface markers on the surface of HNepC (e.g. ICAM-1) compared to markers on HEK293 cells.

B.2. Visualizing Virus Inhibition on H1-HeLa Cells by a Viral Inhibition Assay Using Fluorescence DNA aptamers Nas.R-2 and Nas.R-8 that bind to ICAM-1 were tested in a viral inhibition assay compared to a negative control aptamer to demonstrate their efficacy in blocking Rhinovirus infection (FIG. 7).

B.2.1. Aptamer Incubation and Viral Infection

H1-HeLa cells in RPMI+2% Fetal Bovine Serum were seeded onto 24-well plates at $1 \times 10^5$ cells/mL and 1.0 mL/well. The seed medium was aspirated, and 0.5 mL of each aptamer at 40 µM was added to the host cell wells. The host cells were incubated for 30±5 minutes at 33±2° C. with 5±3% $CO_2$. 0.5 mL of Rhinovirus Type 14 at $10^3$ $TCID_{50}$/well was added to the host cell wells without aspiration. The host cell wells were incubated 120±10 minutes at 33±2° C. with 5±3% $CO_2$. The host cells wells were aspirated and refed with 1.0 mL of each aptamer in cell culture medium and returned to incubation at 33±2° C. with 5±3% $CO_2$. After 18±1 hours, the cells were refed with 1.0 mL of a 2× concentration of aptamer in cell culture medium and incubated for 12±1 hours at 33±2° C. with 5±3% $CO_2$.

B.2.2. Quantification of Viral Inhibition

After the total incubation period the host cell plates were frozen at −60 to −90° C. overnight and then thawed at ambient temperature. The contents of each well were individually harvested and centrifuged at 2,000 rpm for 10 minutes. The supernatant of each harvest was collected, serially diluted in cell culture medium and inoculated onto fresh H1-HeLa cells to determine the quantity of infectious virus using a Tissue Culture Infectious Does 50% ($TCID_{50}$) assay. The average yield of virus from control wells with cells treated with cell culture medium only were used to calculate the viral inhibitory activity ($Log_{10}$ reduction) by each aptamer.

TABLE 1

B.2.3.: Results

| Aptamer | Log Viral Titer Reduction | Reduction (%) |
| --- | --- | --- |
| Nas.R-2 | 2.08 | 99.2 |
| Nas.R-8 | 1.33 | 95.3 |

FIG. 7 shows the result as images. Red labelled cells can be seen in the fluorescent image, if the TRITC-labelled virus was able to infect the cells. The position of the cells in the fluorescent images was marked with an arrow based on the corresponding position in the brightfield image. No infection can be seen using the Nas.R-2 aptamer (FIG. 7A fluorescent image; FIG. 7B brightfield image). Nearly no infection can be seen using the Nas.R-8 aptamer (FIG. 7C fluorescent image; FIG. 7D brightfield image). The cells were infected and appear red (FIG. 7E) using the negative control aptamer (FIG. 7F brightfield image) and FIGS. 7G and H show the control cells which were not infected with the virus (FIG. 7G fluorescent image FIG. 7H brightfield image).

C. Determination of Binding Affinity by Surface Plasmon Resonance (SPR)

C.1. Immobilization of RNA Aptamers in Gold Chips

RNA aptamers Nas.R-1, Nas.R-2, Nas.R-4, Nas.R-8, and a negative control were immobilized on the surface of gold chips. In brief, the RNA aptamer was dissolved in 1×PBS buffer supplemented with 10 mM EDTA. Then, an aliquot of 20 µL of this solution was added to 3.375 mg of 1-ethyl-3-(3-dimethylaminopropyl)carbodiimide (EDC) in a 1.5 mL tube. Next, an aliquot of 13.5 µL of cystamine-imidazole solution was added to the RNA aptamer and EDC solution, followed by mixing and centrifugation. The supernatant was removed and an additional aliquot of 54 µL of 100 µM imidazole (pH 6.0) was added. The solution was incubated at room temperature overnight. Finally, an RNA cleanup column was used to remove unincorporated cystamine and imidazole.

After conjugation of the cystamine moeities to phosphoramidate bonds at the 5' phosphate group, the aptamer was immobilized on a gold chip by depositing an aliquot of 10 nL of aptamer solution at a concentration of 10 µM onto the surface of the chip. The gold reduces the cystamine to a pair of thiols and then catalyzes the reduction reaction that results in the covalent bond between the gold surface and the thiol groups of the modified aptamers.

C.2. Surface Plasmon Resonance (SPR) Procedure

Figure 8:
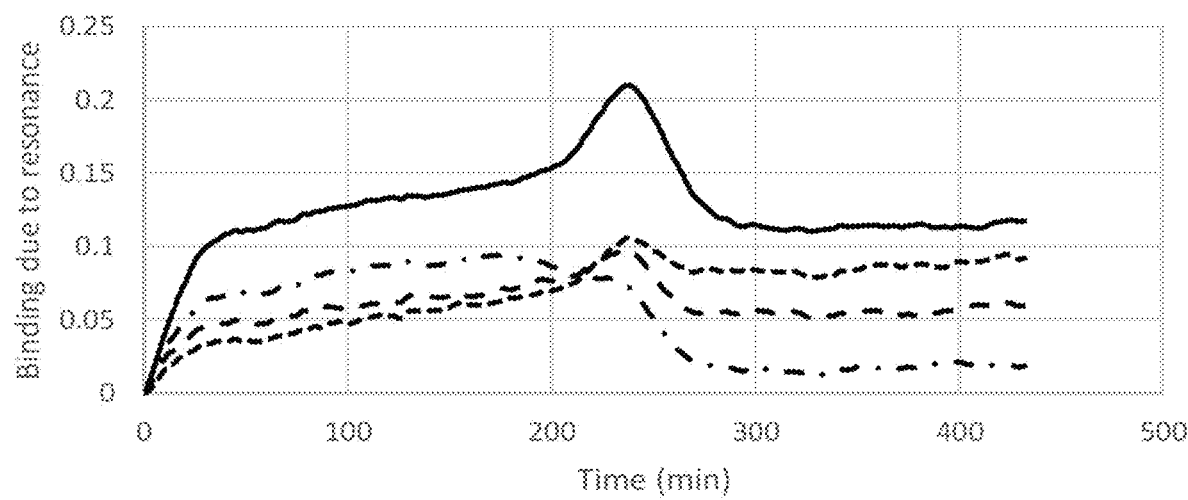
FIG. 8 illustrates the surface plasmon resonance curve of aptamers Nas.R-1, Nas.R-2, Nas.R-4, and Nas.R-8 with 250 nM exogenous ICAM-1.
Figure 9:
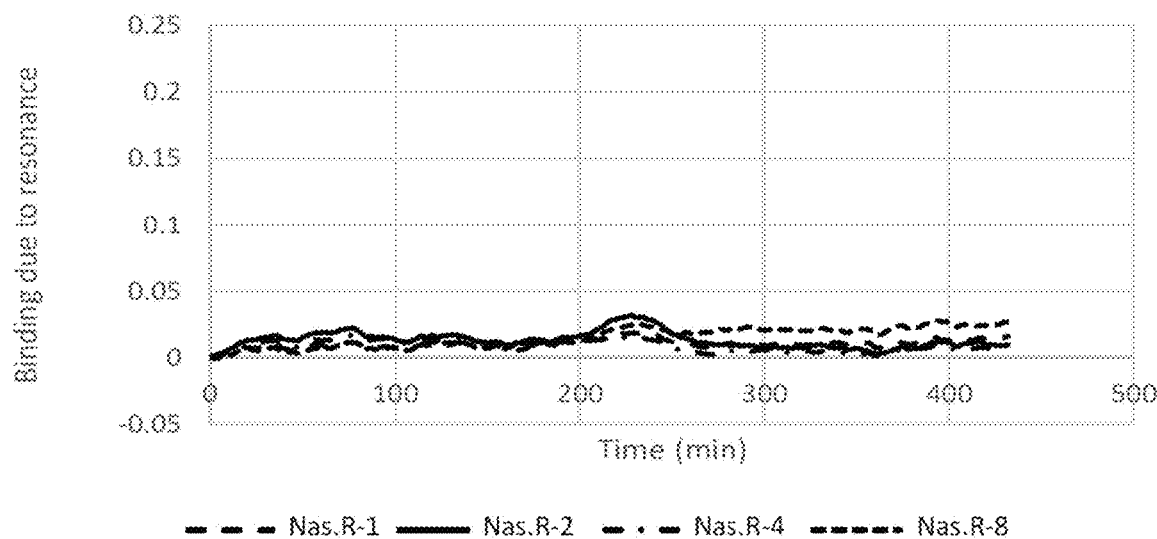
FIG. 9 illustrates the surface plasmon resonance curve of aptamers Nas.R-1, Nas.R-2, Nas.R-4, and Nas.R-8 with 250 nM human serum albumin.

Solutions of 200 µL of ICAM-1 protein or human serum albumin were flown over the gold chip at a concentration of 250 nM and a flow rate of 50 µL/min using an Openplex Surface Plasmon Resonance System (Horiba, Kyoto, Kyoto, Japan). Thus, the association phase lasted for 4 minutes after injection and was immediately followed by the disassociation phase (see FIGS. 8 and 9). The total resonance of the negative control aptamer was subtracted from the total resonance observed for each of the candidate aptamers. The result corresponds to the resonance contribution due to the binding of the protein to the aptamer.

The kd (koff) value was calculated by fitting the curve to equation [1]:

$$x' \sim -kd^*x \qquad [1]$$

wherein x is the resonance due to binding and x' is the derivative of this value at each time point captured on the disassociation curve. The kd value is then used to determine the ka value by using equation [2]:

$$x' \sim ka^*Rmax^*c - (ka^*c + kd)^*x \qquad [2]$$

where Rmax is the maximum resonance due to binding observed, and c is the concentration of the injectant. Finally, the dissociation equilibrium constant kD was calculated as the ratio of kd over ka (see Table 2). The low nanomolar kD values obtained for the different aptamers confirm the strong binding affinity of such molecules towards ICAM-1 and validate the aptamer selection process described in Example 1. As used herein, "kd" refers to the dissociation rate, "ka" refers to the association rate, and "kD" refers to the dissociation equilibrium constant.

TABLE 2

Binding Coefficients of Nas.R-1, Nas.R-2, Nas.R-4, and Nas.R-8 on 250 nM Exogenous ICAM-1.

| Aptamer | Nas.R-1 | Nas.R-2 | Nas.R-4 | Nas.R-8 |
| --- | --- | --- | --- | --- |
| kd, [1/s] | 1.27E−02 | 1.42E−02 | 2.25E−02 | 2.63E−03 |
| ka, [1/M · s] | 1.97E+05 | 2.02E+05 | 5.08E+05 | 9.27E+04 |
| kD, [M] | 6.44E−08 | 7.02E−08 | 4.43E−08 | 2.84E−08 |

D. Aptamer Binding Specificity

As described in Example 1, in the selection process, a counter selection was performed against with HEK293 cells. HEK293 cells do not express the ICAM-1 receptor, but they do express the related receptor proteins ICAM-3 and ICAM-5. For certain sequences, for instance Nas.R-2 (SEQ ID NO: 2), substantially higher affinity to nasal cells compared to HEK293 cells was observed. Not wishing to be bound by theory, given the presence of ICAM-5 and ICAM-3 on the HEK293 cells, it stands to reason that the selected aptamers are binding to epitopes from regions of the ICAM-1 receptor protein that are different in sequence from those of the ICAM-5 or ICAM-3 receptors. FIG. 10 illustrates the sequence alignment of ICAM-1, ICAM-3, and ICAM-5 and the regions that are likely to give rise to ICAM-1 specific binding are highlighted.

Rhinoviruses bind to the N-terminal Ig-like C2-type 1 domain of ICAM-1 receptor. Given the selection strategy, including elution with human rhinovirus particles, and counter selection against HEK293 cells, it is clear to one trained in the art that the mature selected aptamer library would be enriched in aptamer sequences that not only bind to the extracellular domain of the ICAM-1 receptor but do so specifically to the Ig-like C2-type 1 domain at the N-terminus.

Figure 11:
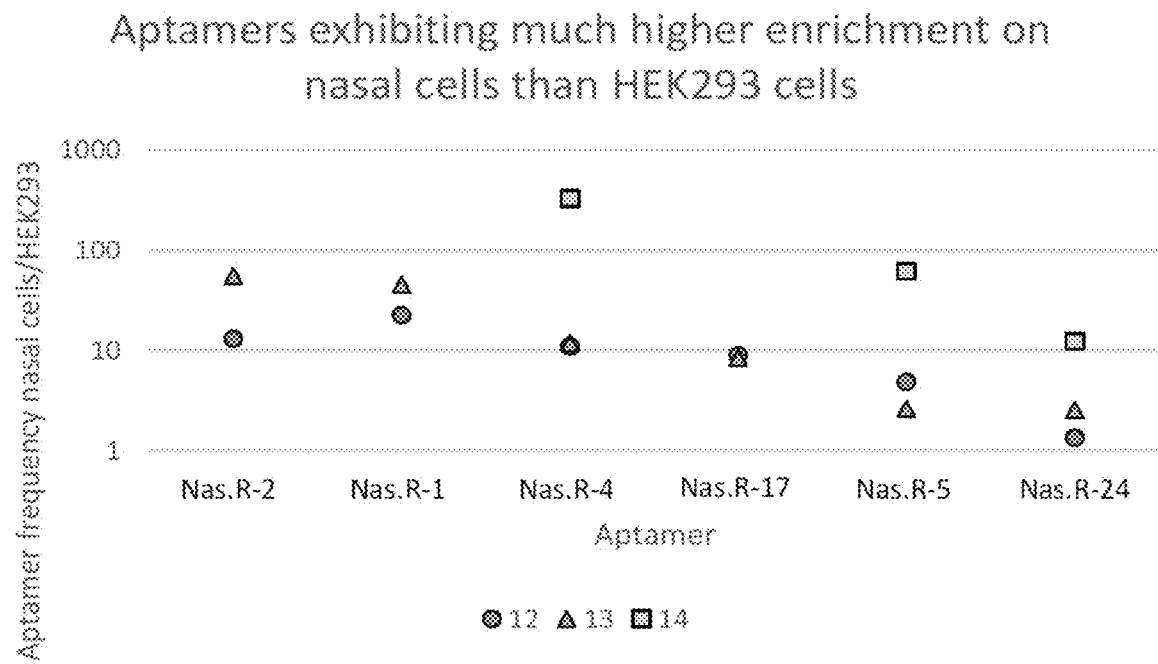
FIG. 11 illustrates examples of sequences that exhibited higher enrichment levels with nasal cells positive selection than with HEK293 cells positive selection.

FIG. 11 illustrates a fold comparison in aptamer frequency over the final three selection rounds applied in the aptamer selection process. The data is presented as the frequency of the individual aptamer sequence as selected against nasal cells divided by the frequency of the same sequence observed in selection against HEK293 cells. For aptamers Nas.R-2, Nas.R-1, and Nas.R-17, the sequences were not observed in the selections against HEK293 cells (the legend refers to the selection round). That is, at least in terms of the subsample of sequences observed in the next generation sequencing process, these sequences were observed at high frequency in selection round 14 against the nasal cells but not observed at all in the selections against HEK293 cells.

Figure 12:
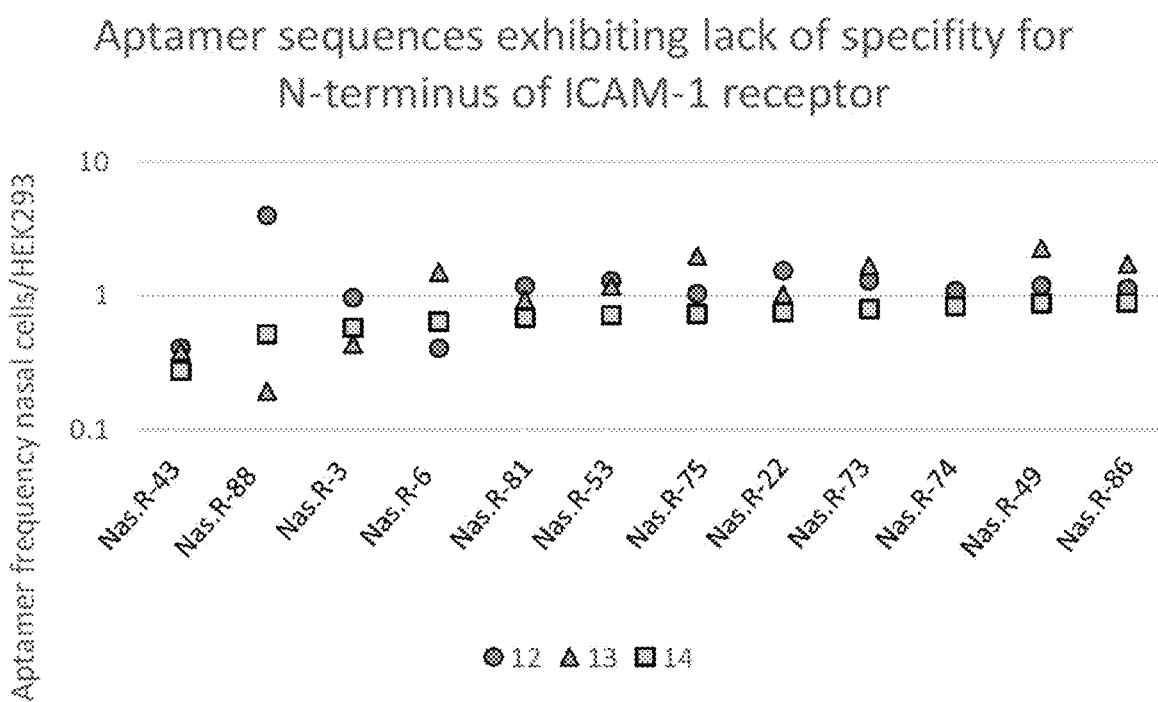
FIG. 12 illustrates examples of sequences in selection round 14 that exhibited higher enrichment levels with HEK293 positive selection than with positive selection against nasal cells.

Not wishing to be bound by theory, aptamers that did not exhibit enrichment in frequency when selected on nasal cells compared to HEK293 cells should be considered as aptamers that likely would not block HRV binding. FIG. 12 depicts sequences that in selection round 14 all exhibited higher enrichment levels with HEK293 positive selection than with positive selection against nasal cells. These aptamers would be expected to bind to regions of the ICAM-1 receptor that are not in the N-terminus and that have considerable sequence identity with regions of ICAM-3 or ICAM-5.

Example 3. Analysis of Sequences Similarity

Alignment of SEQ ID NO: 1 to SEQ ID NO: 100 was performed using the software Align X, a component of Vector NTI Advanced 11.5.4 by Invitrogen. Several groups of sequences have at least 90%, at least 70%, or at least 50% nucleotide sequence identity as illustrated in the alignments of FIGS. 13, 14, and 15. In these alignments, only the central variable region of the aptamers was included for simplicity. Thus, oligonucleotides with at least 50%, at least 70%, or at least 90% nucleotide sequence identity to sequences selected from the group consisting of SEQ ID NO: 1 to SEQ ID NO: 200 are included as part of the current invention.

Example 4. Motif Analysis and Predicted Secondary Structure

Aptamers bind to target molecules on the basis of the lowest free-energy shape that they form. The lowest free energy shape is a function of homology between regions within the single stranded sequence. These regions of homology fold back onto each other and thus create the secondary and tertiary shape of the aptamer that is crucial to enable binding. We characterized the core characteristics of these aptamers through a combined analysis of conserved motif sequences and their effect on the predicted structure of the whole aptamer. A motif in this context is defined as a contiguous sequence of nucleotides of a defined length. For this example, we considered each possible overlapping six nucleotide motif within the random region of each aptamer characterized.

The frequency of motifs of six nucleotides from the random regions of the top aptamers (Nas.R-1, Nas.R-2, Nas.R-4, and Nas.R-8) within all the sequences of selection round 14—Nasal Epithelial Cell Split library was determined. Then, the average motif frequency was subtracted from the frequency of each motif and this value was divided by the standard deviation of all the motifs frequencies in that selection round, resulting in a Z value for every motif. It stands to reason that sequences containing high frequency motifs also bind to the target molecule and are part of the present invention.

The prediction of the secondary structures of the aptamers was performed with The Vienna RNA Websuite. (http://rna.tbi.univie.ac.at//cgi-bin/RNAWebSuite/RNAfold.cgi. Gruber A R, Lorenz R, Bernhart S H, Neuböck R, Hofacker IL; Nucleic Acids Research, Volume 36, Issue suppl_2, 1 Jul. 2008, Pages W70-W74, DOI: 10.1093/nar/gkn188) and the motifs are highlighted within these structures.

Figure 16:
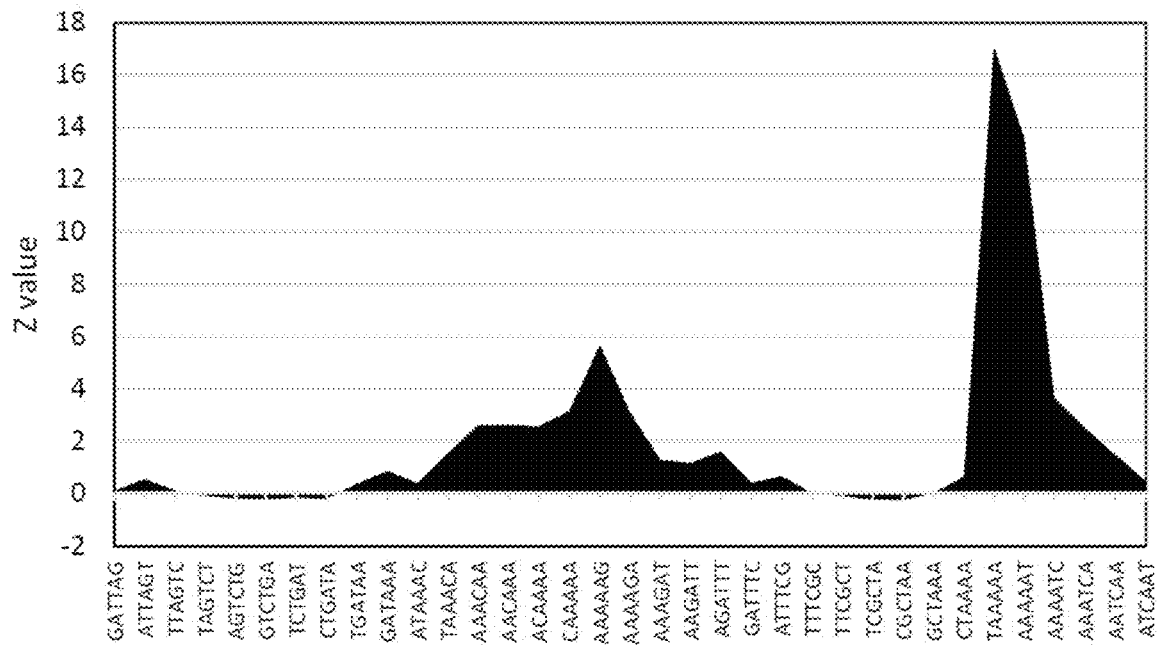
FIG. 16 illustrates the results of the motif analysis of random region of aptamer Nas.R-1.

A. Analysis of the Role of Conserved Motifs on Structure within the Aptamer Nas.R-1:

The results of motif analysis are presented in FIG. 16. The overlapping six nucleotide motifs comprising the random region of the aptamer are provided consecutively along the x axis in this figure. The y axis provides a statistical significance (Z value) for each motif in the library. The Z value was computed as the observed frequency of this motif in the library minus the average of the frequency for all motifs in the library and this subtractant was divided by the standard deviation of all motifs in the library to provide the Z value. Thus, a Z value of 2 represents a frequency of this motif in the library that is two standard deviations greater than the average value for all motifs.

Figure 17:
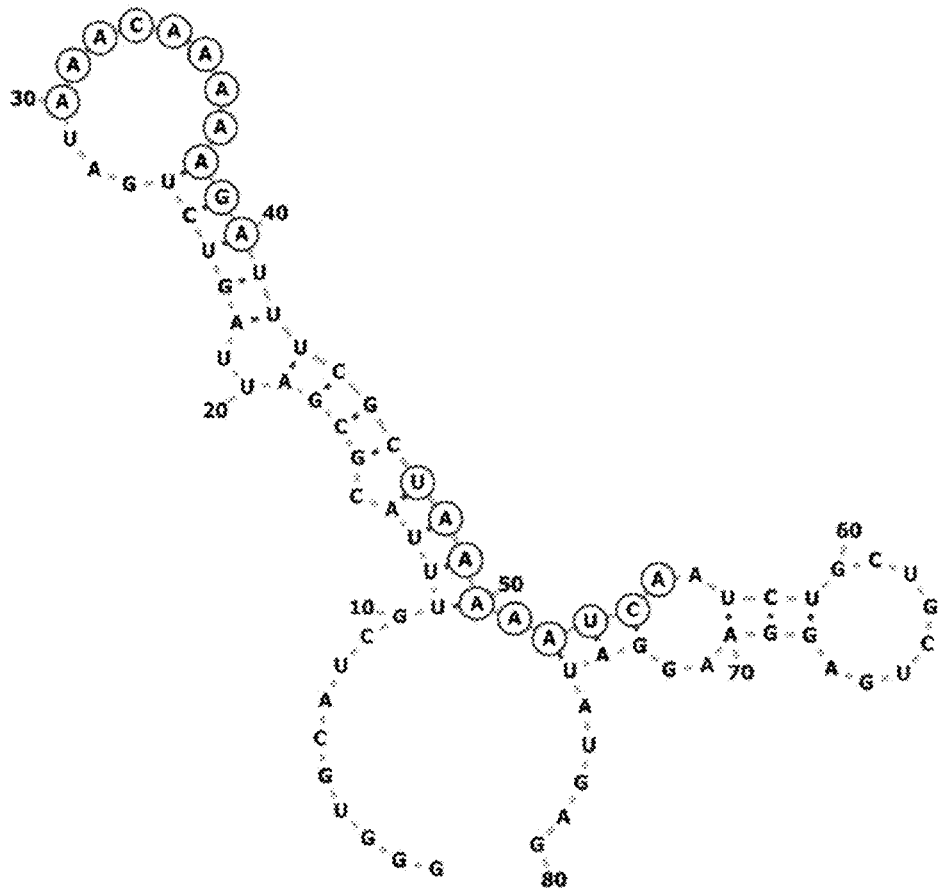
FIG. 17 illustrates the predicted secondary structures of aptamer Nas.R-1 and its conserved motifs (see, e.g., SEQ ID NO: 201, and SEQ ID NO: 202).

In FIG. 16, it is clear that the sequences AAACAAAAAGA (see, e.g., SEQ ID NO: 201) and UAAAAAUCA (see, e.g., SEQ ID NO: 202) were conserved at a level that represented more than two standard deviations from the average. The lowest free energy predicted structure of the Nas.R-1 aptamer and the consensus sequences are shown in FIG. 17.

```
SEQ ID NO: 201:
5'-AAACAAAAAGA-3'

SEQ ID NO: 202:
5'-UAAAAAUCA-3'
```

Sequences containing any of these motifs are also expected to bind to ICAM-1 and are included as embodiments of the present invention. The conclusions arrived at within this example regarding conserved motifs in the RNA sequence would apply to the DNA sequence as well. Thus, any sequences containing the corresponding deoxyribonucleotide motif

```
SEQ ID NO: 203:
5'-AAACAAAAAGA-3'

SEQ ID NO: 204:
5'-TAAAAATCA-3'
``` are also included as embodiments.

Figure 18:
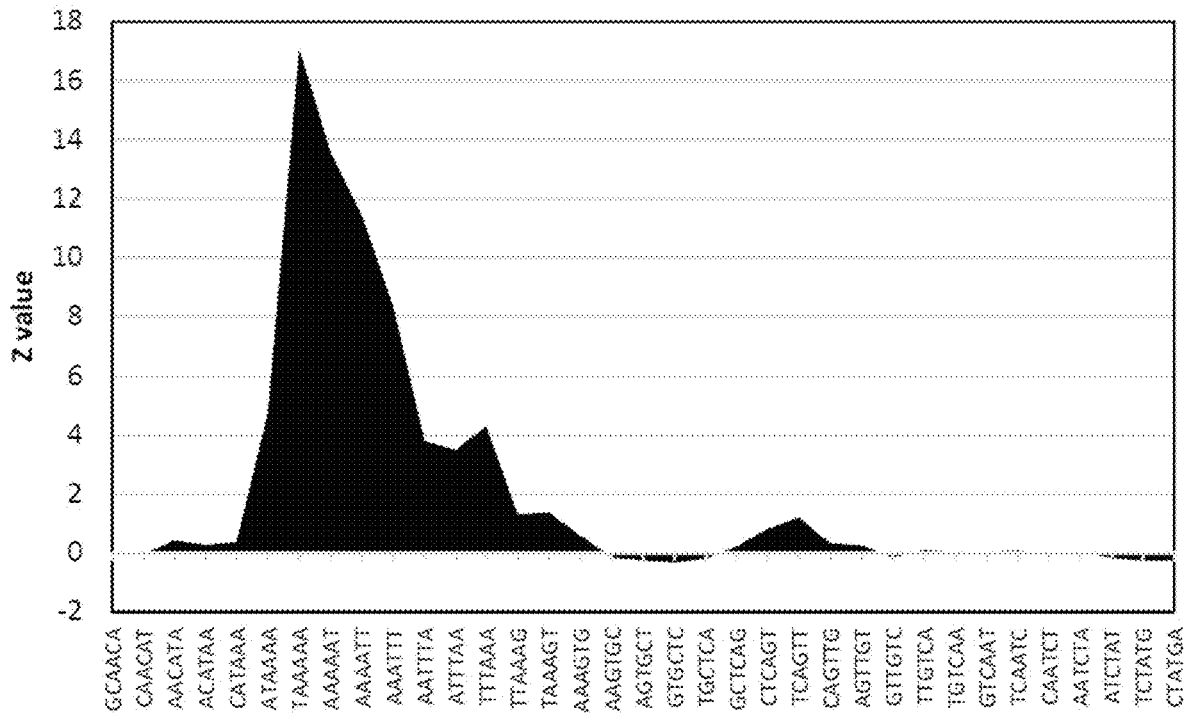
FIG. 18 illustrates the results of the motif analysis of random region of aptamer Nas.R-4.

B. Analysis of the Role of Conserved Motifs on Structure within the Aptamer Nas.R-4:

The analysis of the role of conserved motifs on structure within aptamer Nas.R-4 was performed in a manner identical to that described for Nas.R-1. FIG. 18 provides a summary of the motif analysis for aptamer Nas.R-4. There is a thirteen-nucleotide motif present at a frequency that was more than two standard deviations from the overall average motif frequency in the selected libraries,

```
SEQ ID NO 205:
5'-AUAAAAAUUUAAA-3'.
```

Sequences containing this motif are also expected to bind to ICAM-1 and are included as embodiments of the present invention. Any sequences containing the corresponding deoxyribonucleotide motif:

```
SEQ ID NO 206:
5'-ATAAAAATTTAAA-3'.
``` are also expected to bind to ICAM-1 and are included as embodiments of the present invention.

Figure 19:
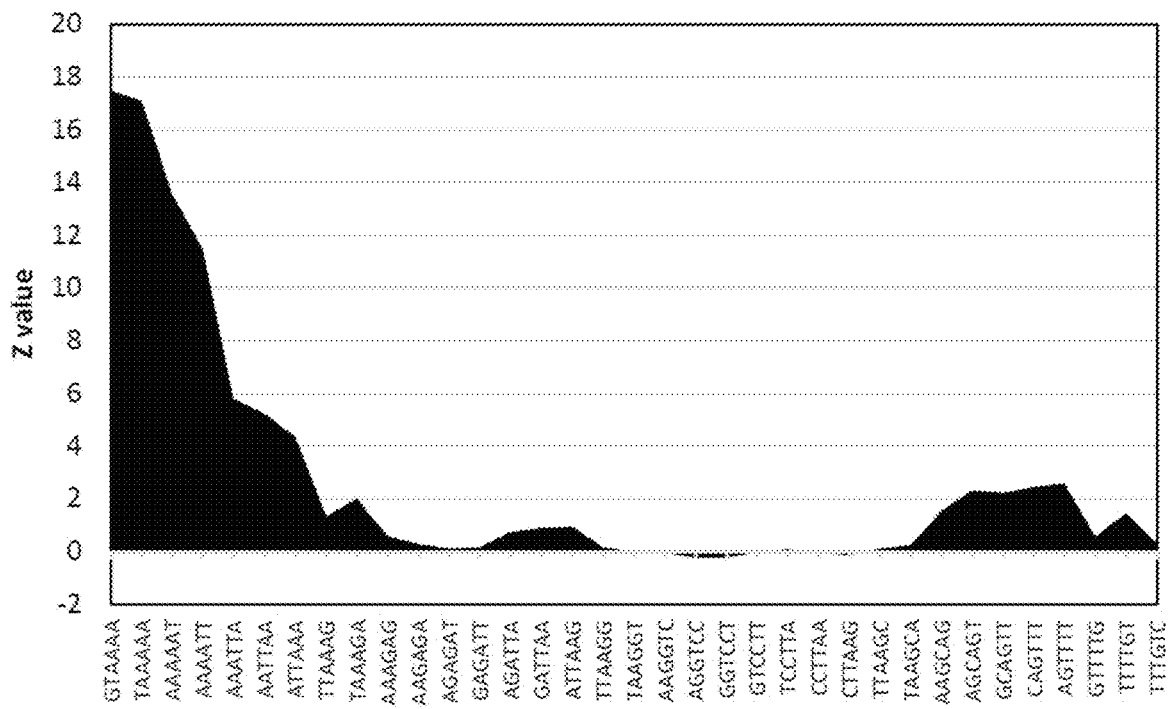
FIG. 19 illustrates the results of the motif analysis of random region of aptamer Nas.R-8.

C. Analysis of the Role of Conserved Motifs on Structure within the Aptamer Nas.R-8:

The analysis of the role of conserved motifs on structure within aptamer Nas.R-8 was performed in a manner identical to that described for Nas.R-1 and Nas.R-4. FIG. 19 provides a summary of the motif analysis for aptamer Nas.R-8. There is a twelve-nucleotide motif present at a frequency that was more than two standard deviations from the overall average motif frequency in the selected libraries,

```
           SEQ ID NO: 207:
           5'-GUAAAAAUUAAA-3'
```

Sequences containing this motif are also expected to bind to ICAM-1 and are included as embodiments of the present invention. Furthermore, any sequences containing the corresponding deoxyribonucleotide motif:

```
           SEQ ID NO 208:
           5'-GTAAAAATTAAA-3'
``` are also expected to bind to ICAM-1 and are included as embodiments.

Figure 20:
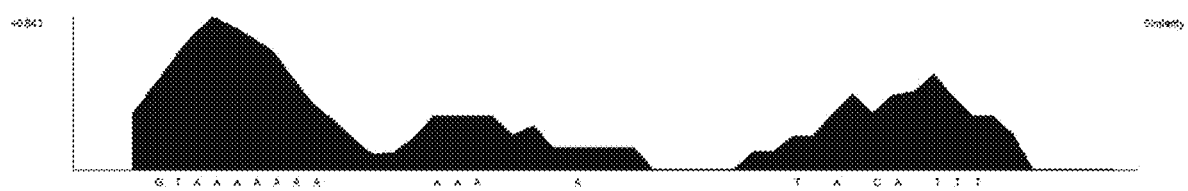
FIG. 20 illustrates the motif analysis of the random region of the top 100 aptamers shown as DNA sequences.

D. Analysis of Common Motifs within Aptamer Library:

A search for common motifs within the top 100 sequences in terms of frequency was performed (see FIG. 20). The lead motifs identified in terms of significant deviation from random distribution were SEQ ID NO: 209 and SEQ IP NO: 210.

```
           SEQ ID NO: 209:
           5'-GUAAAAAA-3'

SEQ ID NO: 210:
           5'-UNAGCANUUU-3'
```

Oligonucleotides comprising the motifs SEQ ID NO: 209, SEQ ID NO: 210, or both are included as an embodiment of the current invention. Similarly, any sequences containing the corresponding deoxyribonucleotide motifs

```
           SEQ ID NO: 211:
           5'-GTAAAAAA-3'

SEQ ID NO: 212:
           5'-TNAGCANTTT-3'
``` are also expected to bind to ICAM-1 and are included as embodiments of the present invention.

TABLE 3

List of top sequences from selection experiment. All the pyrimidine nucleotides are fluorinated at the 2' position of the pentose group.

| SEQ ID NO | Name | Sequence |
|---|---|---|
| 1 | Nas.R-1 | GGGUGCAUCGUUUACGCGAUUAGUCUGAUAAACAAAAAGAUUUCGCUAAAAAUCAAUCUGCUGCUGAGGAAGGAUAUGAG |
| 2 | Nas.R-2 | GGGUGCAUCGUUUACGCAGAUAGCAGCAGGAAUCAAGCGGUAGGAGUCUAGCAGAAGCUGCUGCUGAGGAAGGAUAUGAG |
| 3 | Nas.R-3 | GGGUGCAUCGUUUACGCAUUUCGUUUUAUUUCAGUUUAAUUGCGUUUAGUAUCUGGCUGCUGAGGAAGGAUAUGAG |
| 4 | Nas.R-4 | GGGUGCAUCGUUUACGCGCAACAUAAAAAUUUAAAGUGCUCAGUUGUCAAUCUAUGACUGCUGCUGAGGAAGGAUAUGAG |
| 5 | Nas.R-5 | GGGUGCAUCGUUUACGCGUAAAUGGUCCGCUAUUAAAAGAAAAGAAUGAAGUCUCAGCUGCUGCUGAGGAAGGAUAUGAG |
| 6 | Nas.R-6 | GGGUGCAUCGUUUACGCUAUUUCAUUUGUUUUUUAAUUUACUAGUGUAAACAAUCCUGCUGCUGAGGAAGGAUAUGAG |
| 7 | Nas.R-7 | GGGUGCAUCGUUUACGCGUAAAUAAGUAGAUAAAGUGGCAGUUUGUUUUCCUUGGAACUGCUGCUGAGGAAGGAUAUGAG |
| 8 | Nas.R-8 | GGGUGCAUCGUUUACGCGUAAAAAUUAAAGAGAUUAAGGUCCUUAAGCAGUUUUGUCCUGCUGCUGAGGAAGGAUAUGAG |
| 9 | Nas.R-9 | GGGUGCAUCGUUUACGCGUAAAAAAAUCAAAACUUCAGCAAAUUAUUUAUCAACGUCCUGCUGCUGAGGAAGGAUAUGAG |
| 10 | Nas.R-10 | GGGUGCAUCGUUUACGCGUAAAUAAAUUAAAAGAACUUCUUCAGCAAUCAAUAUCCUGCUGCUGAGGAAGGAUAUGAG |
| 11 | Nas.R-11 | GGGUGCAUCGUUUACGCGUAAAUAAAAAUGAAAAAUUGUCUCUCAGCUUUCAAAGUCCUGCUGCUGAGGAAGGAUAUGAG |
| 12 | Nas.R-12 | GGGUGCAUCGUUUACGCGUAAAAAAAAAAUAUCUUCGGAGAAUUCAGCAAUUUUAUCCUGCUGCUGAGGAAGGAUAUGAG |
| 13 | Nas.R-13 | GGGUGCAUCGUUUACGCGUAAAAAUUUUCAUCUCAGCAAUUAAAUCCAAAGAAUCCACUGCUGCUGAGGAAGGAUAUGAG |
| 14 | Nas.R-14 | GGGUGCAUCGUUUACGCGUAAAAUAUAUCAGCAAAGUAGUUUAAGCCUCCUCAGUUUCUGCUGCUGAGGAAGGAUAUGAG |
| 15 | Nas.R-15 | GGGUGCAUCGUUUACGCGUAAAUUAUGAAAAAUACAGCAAGGAUUUAACCUCAGUUUCUGCUGCUGAGGAAGGAUAUGAG |

TABLE 3-continued

List of top sequences from selection experiment. All the pyrimidine nucleotides are fluorinated at the 2' position of the pentose group.

| SEQ ID NO | Name | Sequence |
|---|---|---|
| 16 | Nas.R-16 | GGGUGCAUCGUUUACGCGUAAAAUAAAUAAAUCUUCAAAGUACAGACCUCGAUUUUUCUGCUGCUGAGGAAGGAUAUGAG |
| 17 | Nas.R-17 | GGGUGCAUCGUUUACGCUUAUAGGUAUUAGACAUUUCAAUUAAAGUGAAUUAGUGUCUGCUGCUGAGGAAGGAUAUGAG |
| 18 | Nas.R-18 | GGGUGCAUCGUUUACGCGUAAAAUGUGACAGCAGGAUAAUAAAAUAAGUACUCAGUACUGCUGCUGAGGAAGGAUAUGAG |
| 19 | Nas.R-19 | GGGUGCAUCGUUUACGCGUAAUUAAGAAAAAUAAAAGUACUCUGCAGUUUUUAUCCACUGCUGCUGAGGAAGGAUAUGAG |
| 20 | Nas.R-20 | GGGUGCAUCGUUUACGCGUAAAAAUAAAAUUUCCCAGACCAGUUAUCUGCCUUAAACUGCUGCUGAGGAAGGAUAUGAG |
| 21 | Nas.R-21 | GGGUGCAUCGUUUACGCGUAAAGAAAAAAAUCAGCUUUUAGUCGCCUUCCAUUUUGACUGCUGCUGAGGAAGGAUAUGAG |
| 22 | Nas.R-22 | GGGUGCAUCGUUUACGCGUAAAUAAAUAAUCAAAAUUACACUCAGUGGCAAUUUCCUCUGCUGCUGAGGAAGGAUAUGAG |
| 23 | Nas.R-23 | GGGUGCAUCGUUUACGCGUAAAAUACAGGAUACGACAAUAACUCAGCAGAUUUUAUCCUGCUGCUGAGGAAGGAUAUGAG |
| 24 | Nas.R-24 | GGGUGCAUCGUUUACGCGUUAAAAAUUGUGCACUGAGAUGACGCAGCAUUAACUACACUGCUGCUGAGGAAGGAUAUGAG |
| 25 | Nas.R-25 | GGGUGCAUCGUUUACGCGUAAAUAAAAUUAAUCAGCAAUUUCCACUCAGUUGUACCUGCUGCUGAGGAAGGAUAUGAG |
| 26 | Nas.R-26 | GGGUGCAUCGUUUACGCGUAAAAAUAAAAAAUCUCGAUCACUGCAGUUUUAUUCCGGCUGCUGCUGAGGAAGGAUAUGAG |
| 27 | Nas.R-27 | GGGUGCAUCGUUUACGCGUAAACAAAUAUCGAUUAAAAUAAAAUCUCAGCAAGAAUCCUGCUGCUGAGGAAGGAUAUGAG |
| 28 | Nas.R-28 | GGGUGCAUCGUUUACGCGUAAAAUAAAUAAAAUUAUCCCAGGAGCAAAUUUUCUUCGCUGCUGCUGAGGAAGGAUAUGAG |
| 29 | Nas.R-29 | GGGUGCAUCGUUUACGCGUAGAAGAAUUAAUAGUGGACAUAUCAAUAGCAGUUUUAUCCUGCUGCUGAGGAAGGAUAUGAG |
| 30 | Nas.R-30 | GGGUGCAUCGUUUACGCGUAAACAUAUUCAGCAGUUAAAAUUUAGUAGGUUCAGUAGCUGCUGCUGAGGAAGGAUAUGAG |
| 31 | Nas.R-31 | GGGUGCAUCGUUUACGCGUAAAAAAGAUAAAACUUAGUUGCAGAAUUUGCCUUCAUUCUGCUGCUGAGGAAGGAUAUGAG |
| 32 | Nas.R-32 | GGGUGCAUCGUUUACGCGUAAAAAGUUUGAUGGAAGCAGAUUAGUUUAGUCAAAUUUCUGCUGCUGAGGAAGGAUAUGAG |
| 33 | Nas.R-33 | GGGUGCAUCGUUUACGCGUAAAAUGAAAUAAGGAAUCCUUCAGCAGUAUUUAUCCUUCUGCUGCUGAGGAAGGAUAUGAG |
| 34 | Nas.R-34 | GGGUGCAUCGUUUACGCGUAAAGAAUAAAAAUGACAAAAUUCUCAGCUUUUGUCAACCUGCUGCUGAGGAAGGAUAUGAG |
| 35 | Nas.R-35 | GGGUGCAUCGUUUACGCGUAAAAAUGAAAUGAAAAAAUUCUCAGCUGUCUAUCUUCCUGCUGCUGAGGAAGGAUAUGAG |
| 36 | Nas.R-36 | GGGUGCAUCGUUUACGCGUAAAUAAGUAAAAAACUCAGUUUUCAGUUAAGUAUCCAACUGCUGCUGAGGAAGGAUAUGAG |
| 37 | Nas.R-37 | GGGUGCAUCGUUUACGCGUAAAUUUCAGCAGUAAUAAUAACACUUCUUCAGUUUGCUGCUGCUGAGGAAGGAUAUGAG |
| 38 | Nas.R-38 | GGGUGCAUCGUUUACGCGUAAAAUUAAGAAGUAUUAUCAGUUAGCUUUUUCUUCCAACUGCUGCUGAGGAAGGAUAUGAG |
| 39 | Nas.R-39 | GGGUGCAUCGUUUACGCGUAAAAUAAAAGUUUCCUAUCAGCAAACUCACAAAUUCCUGCUGCUGAGGAAGGAUAUGAG |
| 40 | Nas.R-40 | GGGUGCAUCGUUUACGCGUAAAAUGAAAUGAAAAGAAUUGAACUUGGCAGAUUUUCCUGCUGCUGAGGAAGGAUAUGAG |
| 41 | Nas.R-41 | GGGUGCAUCGUUUACGCGUAAAUUAAAGUAGCAGUAAUUUCAGCAGUUUUUACCUCUCUGCUGCUGAGGAAGGAUAUGAG |
| 42 | Nas.R-42 | GGGUGCAUCGUUUACGCGUAAAUAAAGGAUAAAAUAAUUUCAGGGCAGUUUCUCAUCCUGCUGCUGAGGAAGGAUAUGAG |
| 43 | Nas.R-43 | GGGUGCAUCGUUUACGCAGGAUCGUUUUAAGUAAAAUAAAAGAUUUCCUUGGUAAUCCUGCUGCUGAGGAAGGAUAUGAG |

TABLE 3-continued

List of top sequences from selection experiment. All the pyrimidine nucleotides are fluorinated at the 2' position of the pentose group.

| SEQ ID NO | Name | Sequence |
|---|---|---|
| 44 | Nas.R-44 | GGGUGCAUCGUUUACGCGUAAAAUA AAGAUCAAUUAAAGGCUUUGAUCGA UUUUCCUCUGCUGCUGAGGAAGGAU AUGAG |
| 45 | Nas.R-45 | GGGUGCAUCGUUUACGCGUAAAAAU UAGAGAUUAAAAUAGUUCCUUUCAG UUUUGUCCUGCUGCUGAGGAAGGAU AUGAG |
| 46 | Nas.R-46 | GGGUGCAUCGUUUACGCGUAAAAUU GACAUGUGAAAAGCAGACAGCAAA UAUUCCUCUGCUGCUGAGGAAGGAU AUGAG |
| 47 | Nas.R-47 | GGGUGCAUCGUUUACGCGUAAAUAA CCAGUUAUACAGAAAGAUCUCAGCA AUUUAUCCUGCUGCUGAGGAAGGAU AUGAG |
| 48 | Nas.R-48 | GGGUGCAUCGUUUACGCUUACGAAA GGAUUGCACCACAUGCGUACUCGAU GAAACACCUGCUGCUGAGGAAGGAU AUGAG |
| 49 | Nas.R-49 | GGGUGCAUCGUUUACGCGUAAAAUA AUAAUUAAACUCAGCAAAUUCAAUC CAACUUUCUGCUGCUGAGGAAGGAU AUGAG |
| 50 | Nas.R-50 | GGGUGCAUCGUUUACGCGUAAACAA GAAUAAAUUCAGCAGUGGUUUUGAU CCUUUGACUGCUGCUGAGGAAGGAU AUGAG |
| 51 | Nas.R-51 | GGGUGCAUCGUUUACGCGUAAAUUA AUCAGAUUGAACAAAAGUUUUCCCU CAGUUUUCUGCUGCUGAGGAAGGAU AUGAG |
| 52 | Nas.R-52 | GGGUGCAUCGUUUACGCGUAAAGAA AAACAUCAGAGCAGUUAUAAUAGUC CUUUUUCCUGCUGCUGAGGAAGGAU AUGAG |
| 53 | Nas.R-53 | GGGUGCAUCGUUUACGCGUAAAGAA AAUAAACUUGAUCAAACUUAGCAGU UUUUAUCCUGCUGCUGAGGAAGGAU AUGAG |
| 54 | Nas.R-54 | GGGUGCAUCGUUUACGCAUUUUCGU UAUAUUUCUGGUUUUUAUGCGUGAG AAUCCUGCUGCUGCUGAGGAAGGAU AUGAG |
| 55 | Nas.R-55 | GGGUGCAUCGUUUACGCGUAAAAAU AAGAUCUCACAGCGACAAAUUUUUC UUCCAGUCUGCUGCUGAGGAAGGAU AUGAG |
| 56 | Nas.R-56 | GGGUGCAUCGUUUACGCGUAAAUUU AAGACAUGACAGCAGACAUUUUAUC UUCAGACCUGCUGCUGAGGAAGGAU AUGAG |
| 57 | Nas.R-57 | GGGUGCAUCGUUUACGCGUAAUAAC AGAAAUAUAACUCAGCUGAAUUUAU UUUUCCGCUGCUGCUGAGGAAGGAU AUGAG |
| 58 | Nas.R-58 | GGGUGCAUCGUUUACGCGUAAAAAU AAAUUCCAAAAUAUUCAGCAGAAAU CCUCGAACUGCUGCUGAGGAAGGAU AUGAG |
| 59 | Nas.R-59 | GGGUGCAUCGUUUACGCGUAAAAAU AAUAGGUUCCAAUCAAGCAGUACAA AAUUCCUCUGCUGCUGAGGAAGGAU AUGAG |
| 60 | Nas.R-60 | GGGUGCAUCGUUUACGCGUAAAAAA UCUAAAAAGAUAUCAGCAGGCAAAU UUUCCUUCUGCUGCUGAGGAAGGAU AUGAG |
| 61 | Nas.R-61 | GGGUGCAUCGUUUACGCGUAAAUA AAGAGGAUAACUACAAUCAUCAGCA AUCAUAUCUGCUGCUGAGGAAGGAU AUGAG |
| 62 | Nas.R-62 | GGGUGCAUCGUUUACGCGUAAAUUU AGUAGAAAGGAAAGACGAAGUUUCC UCAGUUUCUGCUGCUGAGGAAGGAU AUGAG |
| 63 | Nas.R-63 | GGGUGCAUCGUUUACGCGUAAAAAU AAUAGAUCUCAGAAUAUGAAAGCAG UUCUUUCCUGCUGCUGAGGAAGGAU AUGAG |
| 64 | Nas.R-64 | GGGUGCAUCGUUUACGCGUAACAAG AUAUUCACAGCAGAUUUUAAAAAAU UCCUCGUCUGCUGCUGAGGAAGGAU AUGAG |
| 65 | Nas.R-65 | GGGUGCAUCGUUUACGCGUAAAAAG UUGACAAUUAAUAAAAUCUUCUUAG CAUUUUCCUGCUGCUGAGGAAGGAU AUGAG |
| 66 | Nas.R-66 | GGGUGCAUCGUUUACGCGUAAAACA AAAUGAAACUUAUAGCUCAGCAUAU UUUGAUCCUGCUGCUGAGGAAGGAU AUGAG |
| 67 | Nas.R-67 | GGGUGCAUCGUUUACGCGUAAAUUA UCAAAAAGCAGAUUUAAGUAUACC UCAGUUACUGCUGCUGAGGAAGGAU AUGAG |
| 68 | Nas.R-68 | GGGUGCAUCGUUUACGCGUAAAUAA AAUAGCUCAGCAAGGAAGUUUUUUU CCUCAAACUGCUGCUGAGGAAGGAU AUGAG |
| 69 | Nas.R-69 | GGGUGCAUCGUUUACGCGUAAAUUU GAGAAAAGAACAGCAGACUCAAAUC UUUUUAACUGCUGCUGAGGAAGGAU AUGAG |
| 70 | Nas.R-70 | GGGUGCAUCGUUUACGCGUAACAGA AAAUUAAGCUCAGCAAUAGUAAUUA UCCUAGUCUGCUGCUGAGGAAGGAU AUGAG |
| 71 | Nas.R-71 | GGGUGCAUCGUUUACGCGUAAUGAA AAUAAAUCAGUCUCACAGCAUUUUA AAACUUCCUGCUGCUGAGGAAGGAU AUGAG |

TABLE 3-continued

List of top sequences from selection experiment. All the pyrimidine nucleotides are fluorinated at the 2' position of the pentose group.

| SEQ ID NO | Name | Sequence |
|---|---|---|
| 72 | Nas.R-72 | GGGUGCAUCGUUUACGCGUAUUUACAAGCAACAAAGUUACAAUCAGCAGAAUUUAUCCUGCUGCUGAGGAAGGAUAUGAG |
| 73 | Nas.R-73 | GGGUGCAUCGUUUACGCGUAAAAAAUUGUCUAUAGCACUUUUAGAUUCCCAAACUAACUGCUGCUGAGGAAGGAUAUGAG |
| 74 | Nas.R-74 | GGGUGCAUCGUUUACGCGUAAAAAAAUCAGCAAAAUCGAAAACUCAUGCAGUUUGUCCUGCUGCUGAGGAAGGAUAUGAG |
| 75 | Nas.R-75 | GGGUGCAUCGUUUACGCGUAAAAAAUUCCUUAAAAAUUUAACUAACUGGAUAGGUCUCUGCUGCUGAGGAAGGAUAUGAG |
| 76 | Nas.R-76 | GGGUGCAUCGUUUACGCGUAAAACAAAAUUUCUGACAGCAAUUCCUUCGUUAAAAAUCUGCUGCUGAGGAAGGAUAUGAG |
| 77 | Nas.R-77 | GGGUGCAUCGUUUACGCGUAAAUUAUUAAAAAAAAUCAGCAAAGUUUAUUUCCCACGGCUGCUGCUGAGGAAGGAUAUGAG |
| 78 | Nas.R-78 | GGGUGCAUCGUUUACGCGUAAUUAAUCAAACAAUAGCAGCAAAUCUCAGCAAUUUUCCUGCUGCUGAGGAAGGAUAUGAG |
| 79 | Nas.R-79 | GGGUGCAUCGUUUACGCGUAAUUUGAAAGUCUCAUAAAUUUUUUUUUUUUUUCAAUCUGCUGCUGAGGAAGGAUAUGAG |
| 80 | Nas.R-80 | GGGUGCAUCGUUUACGCGUAAAAAUUCAGCAUGAUUUCAUUACUCCUUUCAUUGAUCUGCUGCUGAGGAAGGAUAUGAG |
| 81 | Nas.R-81 | GGGUGCAUCGUUUACGCGUAAAAUAAAUAAAAAUCAGUAGCAAUCUUUCUCACAGUGCUGCUGCUGAGGAAGGAUAUGAG |
| 82 | Nas.R-82 | GGGUGCAUCGUUUACGCGUAAAUAAAAAGCAGAUCUCAGCAAAACUCGUAAAUUCAACUGCUGCUGAGGAAGGAUAUGAG |
| 83 | Nas.R-83 | GGGUGCAUCGUUUACGCGUAAAUAAUGAAGGACUCAGACAGUUAAAAGAUGCAUUAACUGCUGCUGAGGAAGGAUAUGAG |
| 84 | Nas.R-84 | GGGUGCAUCGUUUACGCGUAAAAAAGAUCAAUAUGAAAAUCAGCAGUUAAUAUCUUCCUGCUGCUGAGGAAGGAUAUGAG |
| 85 | Nas.R-85 | GGGUGCAUCGUUUACGCGUAAAAAUAACAAACUUCUCAGCUGUUUAUAUCUCCUGACUGCUGCUGAGGAAGGAUAUGAG |
| 86 | Nas.R-86 | GGGUGCAUCGUUUACGCGUAAAAUUAAACAAAUAGCUCAGCACGAAAAUUUGCGUAACUGCUGCUGAGGAAGGAUAUGAG |
| 87 | Nas.R-87 | GGGUGCAUCGUUUACGCGUAAUUAAAAAACCUUCACACAGAAAACAUUCCUCAAUUUCUGCUGCUGAGGAAGGAUAUGAG |
| 88 | Nas.R-88 | GGGUGCAUCGUUUACGCAUUUUCGUUUUAUUUUAGUUUAAUUGCGUUUAGUAUCUGGCUGCUGAGGAAGGAUAUGAG |
| 89 | Nas.R-89 | GGGUGCAUCGUUUACGCGUAAAAAGUAUAAAGGUUAGAAAUUCAGCAGUUUGAUAUCCUGCUGCUGAGGAAGGAUAUGAG |
| 90 | Nas.R-90 | GGGUGCAUCGUUUACGCGUAAAAAGGAGAAUUAGUACUCACCAGUCGUUUAAAAUUUCUGCUGCUGAGGAAGGAUAUGAG |
| 91 | Nas.R-91 | GGGUGCAUCGUUUACGCGUAAAAAUAAAUAACUACGAGAUCUCAGCAGAUCAUUAUCCUGCUGCUGAGGAAGGAUAUGAG |
| 92 | Nas.R-92 | GGGUGCAUCGUUUACGCGUAAAAUGGUUUUUCAGCAGUUAACAUAAUGCCUCAGUUUCUGCUGCUGAGGAAGGAUAUGAG |
| 93 | Nas.R-93 | GGGUGCAUCGUUUACGCGUAAAUAACAAAAAUCUCAGCUUUUGCAGAAUUUAUCCACCUGCUGCUGAGGAAGGAUAUGAG |
| 94 | Nas.R-94 | GGGUGCAUCGUUUACGCGUAAAUAAACUCACAGCAGAAAAAAUUCCUUCAACUUGUACUGCUGCUGAGGAAGGAUAUGAG |
| 95 | Nas.R-95 | GGGUGCAUCGUUUACGCAGUAGUUAAUAACAAAUAGUCAGUUUUGUCCUUCAUUCUGCUGCUGAGGAAGGAUAUGAG |
| 96 | Nas.R-96 | GGGUGCAUCGUUUACGCGUAAAAAUAGCAGUAGAUAGCGGCAGUUUUGUAUUUGUUACUGCUGCUGAGGAAGGAUAUGAG |
| 97 | Nas.R-97 | GGGUGCAUCGUUUACGCGUAAAAAUUUAAAUAACUCAGCAAUCAUAGAUCCGACUGACUGCUGCUGAGGAAGGAUAUGAG |
| 98 | Nas.R-98 | GGGUGCAUCGUUUACGCGUAAAGAACAGCUGACAAGAAAUUCAAACCUUCAGAUUUUCUGCUGCUGAGGAAGGAUAUGAG |
| 99 | Nas.R-99 | GGGUGCAUCGUUUACGCGUAAAGAUAAUAAGCAGUAUUCAGCAGAUUUGUAAGGUUUCUGCUGCUGAGGAAGGAUAUGAG |

TABLE 3-continued

List of top sequences from selection experiment. All the pyrimidine nucleotides are fluorinated at the 2' position of the pentose group.

| SEQ ID NO | Name | Sequence |
|---|---|---|
| 100 | Nas.R-100 | GGGUGCAUCGUUUACGCGUAAAUAA GAGGCAGACAGUAUUACAAAUAUCC UAAAAUACUGCUGCUGAGGAAGGAU AUGAG |

TABLE 4

List of deoxyribonucleotides aptamers based on the top sequences from selection experiments.

| SEQ ID NO | Name | Sequence |
|---|---|---|
| 101 | Nas.D-1 | GGGTGCATCGTTTACGCGAT TAGTCTGATAAACAAAAGA TTTCGCTAAAAATCAATCTG CTGCTGAGGAAGGATATGAG |
| 102 | Nas.D-2 | GGGTGCATCGTTTACGCAGA TAGCAGCAGGAATCAAGCGG TAGGAGTCTAGCAGAAGCTG CTGCTGAGGAAGGATATGAG |
| 103 | Nas.D-3 | GGGTGCATCGTTTACGCATT TTCGTTTTATTTCAGTTTAA TTGCGTTTAGTATCTGGCTG CTGCTGAGGAAGGATATGAG |
| 104 | Nas.D-4 | GGGTGCATCGTTTACGCGCA ACATAAAAATTTAAAGTGCT CAGTTGTCAATCTATGACTG CTGCTGAGGAAGGATATGAG |
| 105 | Nas.D-5 | GGGTGCATCGTTTACGCGTA AATGGTCCGCTATTAAAAGA AAAGAATGAAGTCTCAGCTG CTGCTGAGGAAGGATATGAG |
| 106 | Nas.D-6 | GGGTGCATCGTTTACGCTAT TTTCATTTGTTTTTTTAATT TACTAGTGTAAACAATCCTG CTGCTGAGGAAGGATATGAG |
| 107 | Nas.D-7 | GGGTGCATCGTTTACGCGTA AATAAGTAGATAAAGTGGCA GTTTGTTTTCCTTGGAACTG CTGCTGAGGAAGGATATGAG |
| 108 | Nas.D-8 | GGGTGCATCGTTTACGCGTA AAAATTAAAGAGATTAAGGT CCTTAAGCAGTTTTGTCCTG CTGCTGAGGAAGGATATGAG |
| 109 | Nas.D-9 | GGGTGCATCGTTTACGCGTA AAAAAATCAAAACTTCAGCA AATTATTTATCAACGTCCTG CTGCTGAGGAAGGATATGAG |
| 110 | Nas.D-10 | GGGTGCATCGTTTACGCGTA AAATAAATTAAAAAGAACTT CTTCAGCAATCAATATCCTG CTGCTGAGGAAGGATATGAG |
| 111 | Nas.D-11 | GGGTGCATCGTTTACGCGTA AATAAAAATGAAAAATTGTC TCTCAGCTTTCAAAGTCCTG CTGCTGAGGAAGGATATGAG |
| 112 | Nas.D-12 | GGGTGCATCGTTTACGCGTA AAAAAAAAATATCTTCGGAG AATTCAGCAATTTTATCCTG CTGCTGAGGAAGGATATGAG |
| 113 | Nas.D-13 | GGGTGCATCGTTTACGCGTA AAAATTTTCATCTCAGCAAT TAAATCCAAAGAATCCACTG CTGCTGAGGAAGGATATGAG |
| 114 | Nas.D-14 | GGGTGCATCGTTTACGCGTA AAATATATCAGCAAAGTAGT TTAAGCCTCCTCAGTTTCTG CTGCTGAGGAAGGATATGAG |
| 115 | Nas.D-15 | GGGTGCATCGTTTACGCGTA AATTATGAAAAATACAGCAA GGATTTAACCTCAGTTTCTG CTGCTGAGGAAGGATATGAG |
| 116 | Nas.D-16 | GGGTGCATCGTTTACGCGTA AAATAAATAAATCTTCAAAG TACAGACCTCGATTTTTCTG CTGCTGAGGAAGGATATGAG |
| 117 | Nas.D-17 | GGGTGCATCGTTTACGCTTA TAGGTATTAGACATTTTCAA TTAAAGTGAATTAGTGTCTG CTGCTGAGGAAGGATATGAG |
| 118 | Nas.D-18 | GGGTGCATCGTTTACGCGTA AAATGTGACAGCAGGATAAT AAAATAAGTACTCAGTACTG CTGCTGAGGAAGGATATGAG |
| 119 | Nas.D-19 | GGGTGCATCGTTTACGCGTA ATTAAGAAAAATAAAAGTAC TCTGCAGTTTTTATCCACTG CTGCTGAGGAAGGATATGAG |
| 120 | Nas.D-20 | GGGTGCATCGTTTACGCGTA AAAATAAAATTTTCCCAGAC CAGTTATCTGCCTTAAACTG CTGCTGAGGAAGGATATGAG |
| 121 | Nas.D-21 | GGGTGCATCGTTTACGCGTA AAGAAAAAAATCAGCTTTTA GTCGCCTTCCATTTTGACTG CTGCTGAGGAAGGATATGAG |
| 122 | Nas.D-22 | GGGTGCATCGTTTACGCGTA AATAAATAATCAAAATTACA CTCAGTGGCAATTTCCTCTG CTGCTGAGGAAGGATATGAG |
| 123 | Nas.D-23 | GGGTGCATCGTTTACGCGTA AAATACAGGATACGACAATA ACTCAGCAGATTTTATCCTG CTGCTGAGGAAGGATATGAG |
| 124 | Nas.D-24 | GGGTGCATCGTTTACGCGTT AAAAATTGTGCACTGAGATG ACGCAGCATTAACTACACTG CTGCTGAGGAAGGATATGAG |

TABLE 4-continued

List of deoxyribonucleotides aptamers based on the top sequences from selection experiments.

| SEQ ID NO | Name | Sequence |
|---|---|---|
| 125 | Nas.D-25 | GGGTGCATCGTTTACGCGTAAATAAAAATTAATCAGCAATTTTCCACTCAGTTGTACCTGCTGCTGAGGAAGGATATGAG |
| 126 | Nas.D-26 | GGGTGCATCGTTTACGCGTAAAAATAAAAAATCTCGATCACTGCAGTTTTATTCCGGCTGCTGCTGAGGAAGGATATGAG |
| 127 | Nas.D-27 | GGGTGCATCGTTTACGCGTAAACAAATATCGATTAAAATAAATCTCAGCAAGAATCCTGCTGCTGAGGAAGGATATGAG |
| 128 | Nas.D-28 | GGGTGCATCGTTTACGCGTAAAATAAATAAAATTATCCCAGGAGCAAATTTTCTTCGCTGCTGCTGAGGAAGGATATGAG |
| 129 | Nas.D-29 | GGGTGCATCGTTTACGCGTAGAAGAATTAATAGTGGACATATCAATAGCAGTTTATCCTGCTGCTGAGGAAGGATATGAG |
| 130 | Nas.D-30 | GGGTGCATCGTTTACGCGTAAACATATTCAGCAGTTAAAATTTAGTAGGTTCAGTAGCTGCTGCTGAGGAAGGATATGAG |
| 131 | Nas.D-31 | GGGTGCATCGTTTACGCGTAAAAAAGATAAAACTTAGTTGCAGAATTTGCCTTCATTCTGCTGCTGAGGAAGGATATGAG |
| 132 | Nas.D-32 | GGGTGCATCGTTTACGCGTAAAAAGTTTGATGGAAGCAGATTAGTTTAGTCAAATTTCTGCTGCTGAGGAAGGATATGAG |
| 133 | Nas.D-33 | GGGTGCATCGTTTACGCGTAAAATGAAATAAGGAATCCTTCAGCAGTATTTATCCTTCTGCTGCTGAGGAAGGATATGAG |
| 134 | Nas.D-34 | GGGTGCATCGTTTACGCGTAAAGAATAAAAATGACAAAATTCTCAGCTTTTGTCAACCTGCTGCTGAGGAAGGATATGAG |
| 135 | Nas.D-35 | GGGTGCATCGTTTACGCGTAAAAAATGAAATGAAAAATTCTCAGCTGTCTATCTTCCTGCTGCTGAGGAAGGATATGAG |
| 136 | Nas.D-36 | GGGTGCATCGTTTACGCGTAAATAAGTAAAAAACTCAGTTTTCAGTTAAGTATCCAACTGCTGCTGAGGAAGGATATGAG |
| 137 | Nas.D-37 | GGGTGCATCGTTTACGCGTAAATTTCAGCAGAGTAATAATAACACTTCTTCAGTTTGCTGCTGCTGAGGAAGGATATGAG |
| 138 | Nas.D-38 | GGGTGCATCGTTTACGCGTAAAATTAAGAAGTATTATCAGTTAGCTTTTTCTTCCAACTGCTGCTGAGGAAGGATATGAG |
| 139 | Nas.D-39 | GGGTGCATCGTTTACGCGTAAAATAAAAAGTTTTCCTATCAGCAAACTCACAAATTCCTGCTGCTGAGGAAGGATATGAG |
| 140 | Nas.D-40 | GGGTGCATCGTTTACGCGTAAAATGAAATGTAAAAGAATTGAACTTGGCAGATTTTCCTGCTGCTGAGGAAGGATATGAG |
| 141 | Nas.D-41 | GGGTGCATCGTTTACGCGTAAATTAAAGTAGCAGTAATTTCAGCAGTTTTTACCTCTCTGCTGCTGAGGAAGGATATGAG |
| 142 | Nas.D-42 | GGGTGCATCGTTTACGCGTAAATAAAGGATAAAATAATTTCAGGGCAGTTTCTCATCCTGCTGCTGAGGAAGGATATGAG |
| 143 | Nas.D-43 | GGGTGCATCGTTTACGCAGGATCGTTTTAAGTAAAATAAAGATTTCCTTGGTAATCCTGCTGCTGAGGAAGGATATGAG |
| 144 | Nas.D-44 | GGGTGCATCGTTTACGCGTAAAATAAAGATCAATTAAAGGCTTTGATCGATTTTCCTCTGCTGCTGAGGAAGGATATGAG |
| 145 | Nas.D-45 | GGGTGCATCGTTTACGCGTAAAAATTAGAGATTAAAATAGTTCCTTTCAGTTTTGTCCTGCTGCTGAGGAAGGATATGAG |
| 146 | Nas.D-46 | GGGTGCATCGTTTACGCGTAAAATTGACAATGTGAAAAGCAGACAGCAAATATTCCTCTGCTGCTGAGGAAGGATATGAG |
| 147 | Nas.D-47 | GGGTGCATCGTTTACGCGTAAATAACCAGTTATACAGAAAGATCTCAGCAATTTATCCTGCTGCTGAGGAAGGATATGAG |
| 148 | Nas.D-48 | GGGTGCATCGTTTACGCTTACAGAAGGATTGCACCACATGCGTACTCGATGAAACACCTGCTGCTGAGGAAGGATATGAG |
| 149 | Nas.D-49 | GGGTGCATCGTTTACGCGTAAAATAATAATTAAACTCAGCAAATTCAATCCAACTTTCTGCTGCTGAGGAAGGATATGAG |
| 150 | Nas.D-50 | GGGTGCATCGTTTACGCGTAAACAAGAATAAATTCAGCAGTGGTTTTGATCCTTTGACTGCTGCTGAGGAAGGATATGAG |
| 151 | Nas.D-51 | GGGTGCATCGTTTACGCGTAAATTAATCAGATTGAACAAAAGTTTTCCCTCAGTTTTCTGCTGCTGAGGAAGGATATGAG |
| 152 | Nas.D-52 | GGGTGCATCGTTTACGCGTAAAGAAAAACATCAGAGCAGTTATAATAGTCCTTTTTCCTGCTGCTGAGGAAGGATATGAG |
| 153 | Nas.D-53 | GGGTGCATCGTTTACGCGTAAAGAAAATAAACTTGATCAAACTTAGCAGTTTTTATCCTGCTGCTGAGGAAGGATATGAG |

TABLE 4-continued

List of deoxyribonucleotides aptamers based on the top sequences from selection experiments.

| SEQ ID NO | Name | Sequence |
|---|---|---|
| 154 | Nas.D-54 | GGGTGCATCGTTTACGCATT TTCGTTATATTTCTGGTTTT TATGCGTGAGAATCCTGCTG CTGCTGAGGAAGGATATGAG |
| 155 | Nas.D-55 | GGGTGCATCGTTTACGCGTA AAAATAAGATCTCACAGCGA CAAATTTTTCTTCCAGTCTG CTGCTGAGGAAGGATATGAG |
| 156 | Nas.D-56 | GGGTGCATCGTTTACGCGTA AATTTAAGACATGACAGCAG ACATTTTATCTTCAGACCTG CTGCTGAGGAAGGATATGAG |
| 157 | Nas.D-57 | GGGTGCATCGTTTACGCGTA ATAACAGAAATATAACTCAG CTGAATTAATTTTTCCGCTG CTGCTGAGGAAGGATATGAG |
| 158 | Nas.D-58 | GGGTGCATCGTTTACGCGTA AAAATAAATTCCAAAATATT CAGCAGAAATCCTCGAACTG CTGCTGAGGAAGGATATGAG |
| 159 | Nas.D-59 | GGGTGCATCGTTTACGCGTA AAAATAATAGGTTCCAATCA AGCAGTACAAAATTCCTCTG CTGCTGAGGAAGGATATGAG |
| 160 | Nas.D-60 | GGGTGCATCGTTTACGCGTA AAAAATCTAAAAAGATATCA GCAGGCAAATTTTCCTTCTG CTGCTGAGGAAGGATATGAG |
| 161 | Nas.D-61 | GGGTGCATCGTTTACGCGTA AAAATAAGAGGATAACTACA ATCATCAGCAATCATATCTG CTGCTGAGGAAGGATATGAG |
| 162 | Nas.D-62 | GGGTGCATCGTTTACGCGTA AATTTAGTAGAAAGGAAAGA CGAAGTTTCCTCAGTTTCTG CTGCTGAGGAAGGATATGAG |
| 163 | Nas.D-63 | GGGTGCATCGTTTACGCGTA AAAATAATAGATCTCAGAAT ATGAAAGCAGTTCTTTCCTG CTGCTGAGGAAGGATATGAG |
| 164 | Nas.D-64 | GGGTGCATCGTTTACGCGTA ACAAGATATTCACAGCAGAT TTTAAAAAATTCCTCGTCTG CTGCTGAGGAAGGATATGAG |
| 165 | Nas.D-65 | GGGTGCATCGTTTACGCGTA AAAAGTTGACAATTAATAAA ATCTTCTTAGCATTTTCCTG CTGCTGAGGAAGGATATGAG |
| 166 | Nas.D-66 | GGGTGCATCGTTTACGCGTA AAACAAAATGAAACTTATAG CTCAGCATATTTTGATCCTG CTGCTGAGGAAGGATATGAG |
| 167 | Nas.D-67 | GGGTGCATCGTTTACGCGTA AATTATCAAAAAAGCAGATT TAAGTATACCTCAGTTACTG CTGCTGAGGAAGGATATGAG |
| 168 | Nas.D-68 | GGGTGCATCGTTTACGCGTA AATAAAAATAGCTCAGCAAGG AAGTTTTTTTCCTCAAACTG CTGCTGAGGAAGGATATGAG |
| 169 | Nas.D-69 | GGGTGCATCGTTTACGCGTA AATTTGAGAAAAGAACAGCA GACTCAAATCTTTTTAACTG CTGCTGAGGAAGGATATGAG |
| 170 | Nas.D-70 | GGGTGCATCGTTTACGCGTA ACAGAAAATTAAGCTCAGCA ATAGTAATTATCCTAGTCTG CTGCTGAGGAAGGATATGAG |
| 171 | Nas.D-71 | GGGTGCATCGTTTACGCGTA ATGAAAATAAATCAGTCTCA CAGCATTTTAAAACTTCCTG CTGCTGAGGAAGGATATGAG |
| 172 | Nas.D-72 | GGGTGCATCGTTTACGCGTA TTTACAAGCAACAAAGTTAC AATCAGCAGAATTTATCCTG CTGCTGAGGAAGGATATGAG |
| 173 | Nas.D-73 | GGGTGCATCGTTTACGCGTA AAAAATTGTCTATAGCACTT TTAGATTCCCAAACTAACTG CTGCTGAGGAAGGATATGAG |
| 174 | Nas.D-74 | GGGTGCATCGTTTACGCGTA AAAAAATCAGCAAAATCGAA AACTCATGCAGTTTGTCCTG CTGCTGAGGAAGGATATGAG |
| 175 | Nas.D-75 | GGGTGCATCGTTTACGCGTA AAAAATTCCTTAAAAATTTA ACTAACTGGATAGGTCTCTG CTGCTGAGGAAGGATATGAG |
| 176 | Nas.D-76 | GGGTGCATCGTTTACGCGTA AAACAAAATTTCTGACAGCA ATTCCTTCGTTAAAAATCTG CTGCTGAGGAAGGATATGAG |
| 177 | Nas.D-77 | GGGTGCATCGTTTACGCGTA AATTATTAAAAAAATCAGCA AAGTTTATTTCCCACGGCTG CTGCTGAGGAAGGATATGAG |
| 178 | Nas.D-78 | GGGTGCATCGTTTACGCGTA ATTAATCAAACAATAGCAGC AAATCTCAGCAATTTTCCTG CTGCTGAGGAAGGATATGAG |
| 179 | Nas.D-79 | GGGTGCATCGTTTACGCGTA ATTTGAAAGTCTCATAAATT TTTTTTTTTTTTTCAATCTG CTGCTGAGGAAGGATATGAG |
| 180 | Nas.D-80 | GGGTGCATCGTTTACGCGTA AAAATTCAGCATGATTTCAA TTACTCCTTTCATTGATCTG CTGCTGAGGAAGGATATGAG |
| 181 | Nas.D-81 | GGGTGCATCGTTTACGCGTA AAATAAATAAAAATCAGTAG CAATCTTTCTCACAGTGCTG CTGCTGAGGAAGGATATGAG |
| 182 | Nas.D-82 | GGGTGCATCGTTTACGCGTA AATAAAAAGCAGATCTCAGC AAAACTCGTAAATTCAACTG CTGCTGAGGAAGGATATGAG |

TABLE 4-continued

List of deoxyribonucleotides aptamers based on the top sequences from selection experiments.

| SEQ ID NO | Name | Sequence |
|---|---|---|
| 183 | Nas.D-83 | GGGTGCATCGTTTACGCGTAAATAATGAAGGACTCAGACAGTTAAAAGATGCATTAACTGCTGCTGAGGAAGGATATGAG |
| 184 | Nas.D-84 | GGGTGCATCGTTTACGCGTAAAAAAGATCAATATGAAAATCAGCAGTTAATATCTTCCTGCTGCTGAGGAAGGATATGAG |
| 185 | Nas.D-85 | GGGTGCATCGTTTACGCGTAAAAATAACAAACTTCTCAGCTGTTTAATATCTCCTGACTGCTGCTGAGGAAGGATATGAG |
| 186 | Nas.D-86 | GGGTGCATCGTTTACGCGTAAAATTAAACAAATAGCTCAGCACGAAAATTTGCGTAACTGCTGCTGAGGAAGGATATGAG |
| 187 | Nas.D-87 | GGGTGCATCGTTTACGCGTAATTAAAAAACCTTCACACAGAAAACATTCCTCAATTTCTGCTGCTGAGGAAGGATATGAG |
| 188 | Nas.D-88 | GGGTGCATCGTTTACGCATTTTCGTTTTATTTTAGTTTAATTGCGTTTAGTATCTGGCTGCTGCTGAGGAAGGATATGAG |
| 189 | Nas.D-89 | GGGTGCATCGTTTACGCGTAAAAAGTATAAAGGTTAGAAATTCAGCAGTTTGATATCCTGCTGCTGAGGAAGGATATGAG |
| 190 | Nas.D-90 | GGGTGCATCGTTTACGCGTAAAAAGGAGAATTAGTACTCACCAGTCGTTTAAAATTTCTGCTGCTGAGGAAGGATATGAG |
| 191 | Nas.D-91 | GGGTGCATCGTTTACGCGTAAAAATAAATAACTACGAGATCTCAGCAGATCATTATCCTGCTGCTGAGGAAGGATATGAG |
| 192 | Nas.D-92 | GGGTGCATCGTTTACGCGTAAAATGGTTTTTCAGCAGTTAACATAATGCCTCAGTTTCTGCTGCTGAGGAAGGATATGAG |
| 193 | Nas.D-93 | GGGTGCATCGTTTACGCGTAAATAACAAAAATCTCAGCTTTTGCAGAATTTATCCACCTGCTGCTGAGGAAGGATATGAG |
| 194 | Nas.D-94 | GGGTGCATCGTTTACGCGTAAATAAACTCACAGCAGAAAAAATTCCTTCAACTTGTACTGCTGCTGAGGAAGGATATGAG |
| 195 | Nas.D-95 | GGGTGCATCGTTTACGCAGTAGTTAATAACAAATAGTCAGCAGTTTTGTCCTTCATTCTGCTGCTGAGGAAGGATATGAG |
| 196 | Nas.D-96 | GGGTGCATCGTTTACGCGTAAAAATAGCAGTAGATAGCGGCAGTTTTGTATTTGTTACTGCTGCTGAGGAAGGATATGAG |
| 197 | Nas.D-97 | GGGTGCATCGTTTACGCGTAAAAATTTAAATAACTCAGCAATCATAGATCCGACTGACTGCTGCTGAGGAAGGATATGAG |
| 198 | Nas.D-98 | GGGTGCATCGTTTACGCGTAAAGAACAGCTGACAAGAAATTCAAACCTTCAGATTTTCTGCTGCTGAGGAAGGATATGAG |
| 199 | Nas.D-99 | GGGTGCATCGTTTACGCGTAAAGATAATAAGCAGTATTCAGCAGATTTGTAAGGTTTCTGCTGCTGAGGAAGGATATGAG |
| 200 | Nas.D-100 | GGGTGCATCGTTTACGCGTAAATAAGAGGCAGACAGTATTACAAATATCCTAAAATACTGCTGCTGAGGAAGGATATGAG |

TABLE 5

List of conserved motifs.

| SEQ ID NO | Sequence |
|---|---|
| 201 | AAACAAAAGA |
| 202 | UAAAAAUCA |
| 203 | AAACAAAAGA |
| 204 | TAAAAATCA |
| 205 | AUAAAAAUUUAAA |
| 206 | ATAAAAATTTAAA |
| 207 | GUAAAAUUAA |
| 208 | GTAAAATTAAA |
| 209 | GUAAAAAAA |
| 210 | UNAGCANUUU |
| 211 | GTAAAAAAA |
| 212 | TNAGCANTTT |

TABLE 6

List of protein sequences

| SEQ ID NO | Description | Sequence |
|---|---|---|
| 213 | ICAM-1 | MAPSSPRPALPALLVLLGALFPGPGNAQTSVSPSKVILPRGGSVLVTCSTSCDQPKLLGIETPLPKKELLLPGNNRKVYELSNVQEDSQPMCYSNCPDGQSTAKTFLTVYWTPERVELAPLPSWQPVGKNLTLRCQVEGGAPRANLTVVLLRGEKELKREPAVGEPAEVTTTVLVRRDHHGANFSCRTELDLRPQGLELFENTSAPYQLQTFVLPATPPQLVSPRVLEVDTQGTVVCSLD |

TABLE 6-continued

List of protein sequences

| SEQ ID NO | Description | Sequence |
|---|---|---|
| | | GLFPVSEAQVHLALGDQRLN PTVTYGNDSFSAKASVSVTA EDEGTQRLTCAVILGNQSQE TLQTVTIYSFPAPNVILTKP EVSEGTEVTVKCEAHPRAKV TLNGVPAQPLGPRAQLLLKA TPEDNGRSFSCSATLEVAGQ LIHKNQTRELRVLYGPRLDE RDCPGNWTWPENSQQTPMCQ AWGNPLPELKCLKDGTFPLP IGESVTVTRDLEGTYLCRAR STQGEVTRKVTVNVLSPRYE IVIITVVAAAVIMGTAGLST YLYNRQRKIKKYRLQQAQKG TPMKPNTQATPP |
| 214 | Extracellular domain of ICAM-1 | QTSVSPSKVILPRGGSVLVT CSTSCDQPKLLGIETPLPKK ELLLPGNNRKVYELSNVQED SQPMCYSNCPDGQSTAKTFL TVYWTPERVELAPLPSWQPV GKNLTLRCQVEGGAPRANLT VVLLRGEKELKREPAVGEPA EVTTTVLVRRDHHGANFSCR TELDLRPQGLELFENTSAPY QLQTFVLPATPPQLVSPRVL EVDTQGTVVCSLDGLFPVSE AQVHLALGDQRLNPTVTYGN DSFSAKASVSVTAEDEGTQR LTCAVILGNQSQETLQTVTI YSFPAPNVILTKPEVSEGTE VTVKCEAHPRAKVTLNGVPA QPLGPRAQLLLKATPEDNGR SFSCSATLEVAGQLIHKNQT RELRVLYGPRLDERDCPGNW TWPENSQQTPMCQAWGNPLP ELKCLKDGTFPLPIGESVTV TRDLEGTYLCRARSTQGEVT RKVTVNVLSPRYE |
| 215 | Ig-like C2-type 1 domain | GGSVLVTCSTSCDQPKLLGI ETPLPKKELLLPGNNRKVYE LSNVQEDSQPMCYSNCPDGQ STA |
| 216 | Ig-like C2-type 2 domain | GKNLTLRCQVEGGAPRANLT VVLLRGEKELKREPAVGEPA EVTTTVLVRRDHHGANFSCR TELDLR |
| 217 | Ig-like C2-type 3 domain | DTQGTVVCSLDGLFPVSEAQ VHLALGDQRLNPTVTYGNDS FSAKASVSVTAEDEGTQRLT CAVILGNQ |
| 218 | Ig-like C2-type 4 domain | GTEVTVKCEAHPRAKVTLNG VPAQPLGPRAQLLLKATPED NGRSFSCSATLEVA |
| 219 | Ig-like C2-type 5 domain | NSQQTPMCQAWGNPLPELKC LKDGTFPLPIGESVTVTRDL EGTYLCRARSTQG |
| 220 | Fragment of ICAM-1 | QTSVSPSKVILPR |
| 221 | Fragment of ICAM-2 | SCDQPKLLGI |
| 222 | Fragment of ICAM-3 | PKKELLLPGNNRKVYE |
| 223 | Fragment of ICAM-4 | YSNCPDGQSTAKTFL |
| 231 | ICAM-3 | MATMVPSVLWPRACWTLLVC CLLTPGVQGQEFLLRVEPQN PVLSAGGSLFVNCSTDCPSS EKIALETSLSKELVASGMGW AAFNLSNVTGNSRILCSVYC NGSQITGSSNITVYRLPERV ELAPLPPWQPVGQNFTLRCQ VEDGSPRTSLTVVLLRWEEE LSRQPAVEEPAEVTATVLAS RDDHGAPFSCRTELDMQPQG LGLFVNTSAPRQLRTFVLPV TPPPRLVAPRFLEVETSWPVD CTLDGLFPASEAQVYLALGD QMLNATVMNHGDTLTATATA TARADQEGAREIVCNVTLGG ERREARENLTVFSFLGPIVN LSEPTAHEGSTVTVSCMAGA RVQVTLDGVPAAAPGQPAQL QLNATESDDGRSFFCSATLE VDGEFLHRNSSVQLRVLYGP KIDRATCPQHLKWKDKTRHV LQCQARGNPYPELRCLKEGS SREVPVGIPFFVNVTHNGTY QCQASSSRGKYTLVVVMDIE AGSSHFVPVFVAVLLTLGVV TIVLALMYVFREHQRSGSYH VREESTYLPLTSMQPTEAMG EEPSRAE |
| 232 | Extracellular domain of ICAM-3 | QEFLLRVEPQNPVLSAGGSL FVNCSTDCPSSEKIALETSL SKELVASGMGWAAFNLSNVT GNSRILCSVYCNGSQITGSS NITVYRLPERVELAPLPPWQ PVGQNFTLRCQVEDGSPRTS LTVVLLRWEEELSRQPAVEE PAEVTATVLASRDDHGAPFS CRTELDMQPQGLGLFVNTSA PRQLRTFVLPVTPPPRLVAPR FLEVETSWPVDCTLDGLFPA SEAQVYLALGDQMLNATVMN HGDTLTATATATARADQEGA REIVCNVTLGGERREARENL TVFSFLGPIVNLSEPTAHEG STVTVSCMAGARVQVTLDGV PAAAPGQPAQLQLNATESDD GRSFFCSATLEVDGEFLHRN SSVQLRVLYGPKIDRATCPQ HLKWKDKTRHVLQCQARGNP YPELRCLKEGSSREVPVGIP FFVNVTHNGTYQCQASSSRG KYTLVVVMDIEAGSSH |
| 233 | ICAM-5 | MPGPSPGLRRALLGLWAALG LGLFGLSAVSQEPFWADLQP RVAFVERGGSLWLNCSTNCP RPERGGLETSLRRNGTQRGL RWLARQLVDIREPETQPVCF FRCARRTLQARGLIRFQRPD RVELMPLPPWQPVGENFTLS CRVPGAGPRASLTLTLLRGA QELIRRSFAGEPPRARGAVL TATVLARREDHGANFSCRAE LDLRPHGLGLFENSSAPREL RTFSLSPDAPRLAAPRLLEV GSERPVSCTLDGLFPASEAR VYLALGDQNLSPDVTLEGDA FVATATATASAEQEGARQLV CNVTLGGENRETRENVTIYS FPAPLLTLSEPSVSEGQMVT VTCAAGAQALVTLEGVPAAV PGQPAQLQLNATENDDRRSF FCDATLDVDGETLIKNRSAE |

TABLE 6-continued

List of protein sequences

| SEQ ID NO | Description | Sequence |
|---|---|---|
| | | LRVLYAPRLDDSDCPRSWTW PEGPEQTLRCEARGNPEPSV HCARSDGGAVLALGLLGPVT RALSGTYRCKAANDQGEAVK DVTLTVEYAPALDSVGCPER ITWLEGTEASLSCVAHGVPP PDVICVRSGELGAVIEGLLR VAREHAGTYRCEATNPRGSA AKNVAVTVEYGPRFEEPSCP SNWTWVEGSGRLFSCEVDGK PQPSVKCVGSGGATEGVLLP LAPPDPSPRAPRIPRVLAPG IYVCNATNRHGSVAKTVVVS AESPPEMDESTCPSHQTWLE GAEASALACAARGRPSPGVR CSREGIPWPEQQRVSREDAG TYHCVATNAHGTDSRTVTVG VEYRPVVAELAASPPGGVRP GGNFTLTCRAEAWPPAQISW RAPPGALNIGLSSNNSTLSV AGAMGSHGGEYECAATNAHG RHARRITVRVAGPWLWVAVG GAAGGAALLAAGAGLAFYVQ STACKKGEYNVQEAESSGEA VCLNGAGGGAGGAAGAEGGP EAAGGAAESPAEGEVFAIQL TSA |
| 234 | Extracellular domain of ICAM-5 | EPFWADLQPRVAFVERGGSL WLNCSTNCPRPERGGLETSL RRNGTQRGLRWLARQLVDIR EPETQPVCFFRCARRTLQAR GLIRTFQRPDRVELMPLPPW QPVGENFTLSCRVPGAGPRA SLTLTLLRGAQELIRRSFAG EPPRARGAVLTATVLARRED HGANFSCRAELDLRPHGLGL FENSSAPRELRTFSLSPDAP RLAAPRLLEVGSERPVSCTL DGLFPASEARVYLALGDQNL SPDVTLEGDAFVATATATAS AEQEGARQLVCNVTLGGENR ETRENVTIYSFPAPLLTLSE PSVSEGQMVTVTCAAGAQAL VTLEGVPAAVPGQPAQLQLN ATENDDRRSFFCDATLDVDG ETLIKNRSAELRVLYAPRLD DSDCPRSWTWPEGPEQTLRC EARGNPEPSVHCARSDGGAV LALGLLGPVTRALSGTYRCK AANDQGEAVKDVTLTVEYAP ALDSVGCPERITWLEGTEAS LSCVAHGVPPPDVICVRSGE LGAVIEGLLRVAREHAGTYR CEATNPRGSAAKNVAVTVEY GPRFEEPSCPSNWTWVEGSG RLFSCEVDGKPQPSVKCVGS GGATEGVLLPLAPPDPSPRA PRIPRVLAPGIYVCNATNRH GSVAKTVVVSAESPPEMDES TCPSHQTWLEGAEASALACA ARGRPSPGVRCSREGIPWPE QQRVSREDAGTYHCVATNAH GTDSRTVTVGVEYRPVVAEL AASPPGGVRPGGNFTLTCRA EAWPPAQISWRAPPGALNIG LSSNNSTLSVAGAMGSHGGE YECAATNAHGRHARRITVRV AGPW |

Combinations

A. An aptamer composition comprising at least one oligonucleotide consisting of: deoxyribonucleotides, ribonucleotides, derivatives of deoxyribonucleotides, derivatives of ribonucleotides, and mixtures thereof; wherein the aptamer composition has a binding affinity for intercellular adhesion molecule 1 (ICAM-1); and wherein the aptamer is configured to reduce the binding of one or more human rhinoviruses to the intercellular adhesion molecule 1 (ICAM-1) and wherein the aptamer composition comprises
  i. at least one oligonucleotide selected from the group consisting of oligonucleotides with at least 80% nucleotide sequence identity to sequences selected from the group consisting of SEQ ID NO: 1 to SEQ ID NO: 200; and/or.
  ii. at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

B. The aptamer composition according to Paragraph A, wherein the at least one oligonucleotide is selected from the group consisting of SEQ ID NO: 2, SEQ ID NO: 4, SEQ ID NO: 5, SEQ ID NO: 7, and SEQ ID NO: 8.

C. The aptamer composition according to Paragraph A-B, wherein the at least one oligonucleotide shows at least 90%, or 95%, or 96%, or 97%, or 98% or 99% nucleotide sequence identity to sequences selected from the group consisting of SEQ ID NO: 1 to SEQ ID NO: 200, or wherein the at least one oligonucleotide shows at least 90%, or 95%, or 96%, or 97%, or 98% or 99% nucleotide sequence identity to sequences selected from the group consisting of SEQ ID NO: 2, SEQ ID NO: 4, SEQ ID NO: 5, SEQ ID NO: 7, and SEQ ID NO: 8.

D. The aptamer composition according to Paragraph A-C, comprising at least one oligonucleotide selected from the group consisting of SEQ ID NO: 1 to SEQ ID NO: 200.

E. The aptamer composition according to Paragraph A-D, comprising at least one oligonucleotide selected from the group consisting of SEQ ID NO: 2, SEQ ID NO: 4, SEQ ID NO: 5, SEQ ID NO: 7, and SEQ ID NO: 8.

F. The aptamer composition according to Paragraph A-E, wherein the at least one oligonucleotide comprises natural or non-natural nucleobases; preferably wherein the non-natural nucleobases are selected from the group comprising hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, and mixtures thereof.

G. The aptamer composition according to Paragraph A-F, wherein the nucleosides of the at least one oligonucleotide are linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, and mixtures thereof.

H. The aptamer composition according to Paragraph A-G, where the derivatives of ribonucleotides or the derivatives of deoxyribonucleotides are selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

I. The aptamer composition according to Paragraph A-H, further comprising at least one polymeric material, wherein the at least one polymeric material is covalently linked to the at least one oligonucleotide; preferably wherein the at least one polymeric material is polyethylene glycol.

J. The aptamer composition according to Paragraph A-I wherein the nucleotides at the 5'- and 3'-ends of the at least one oligonucleotide are inverted.

K. The aptamer composition according to Paragraph A-J, wherein at least one nucleotide of the at least one oligonucleotide is fluorinated at the 2' position of the pentose group; preferably wherein the pyrimidine nucleotides of the at least one oligonucleotide are fluorinated at the 2' position of the pentose group.

L. The aptamer composition according to Paragraph A-K, wherein the at least one oligonucleotide is covalently or non-covalently attached to one or more active ingredients, wherein the one or more active ingredients are selected from the group consisting of: respiratory illness treatment agents, cold-treatment agents, flu-treatment agents, antiviral agents, antimicrobial agents, cooling agents, malodor absorbing agents, natural extracts, peptides, enzymes, pharmaceutical active ingredients, metal compounds, and combinations thereof.

M. An aptamer composition comprising at least one peptide or protein, wherein the peptide or protein is translated from at least one of the oligonucleotides of anyone of paragraphs A-L.

N. The aptamer composition according to Paragraph A-M wherein the aptamer has a binding affinity for the Ig-like C2-type 1 domain (SEQ ID NO: 215) of the intercellular adhesion molecule 1 (ICAM-1), any post-translationally modified versions of said domain, and mixtures thereof.

O. The aptamer composition according to Paragraph A-M, wherein the at least one oligonucleotide is covalently or non-covalently attached to one or more nanomaterials comprising one or more active ingredients.

P. A personal health care composition comprising the at least one aptamer composition according to paragraph A-O.

Q. The personal health care composition according to paragraph P, wherein the at least one nucleic acid aptamer is covalently or non-covalently attached to one or more active ingredients, wherein said one or more active ingredients are selected from the group comprising: respiratory illness treatment agents, cold-treatment agents, flu-treatment agents, antiviral agents, antimicrobial agents, cooling agents, malodor absorbing agents, natural extracts, peptides, enzymes, pharmaceutical active ingredients, metal compounds, and mixtures thereof.

R. The aptamer composition according to paragraph A-O or the personal health care composition according to paragraph P or Q for inhibiting human rhinovirus infection by inhibiting binding to the intercellular adhesion molecule 1 (ICAM-1) and thereby inhibiting entering into cells within the nasal cavity and throat and/or for preventing and treating symptoms associated with respiratory tract viral infections, preferably by delivering the composition to the upper respiratory tract.

S. A method for delivering a personal health care composition to the upper respiratory tract comprising administering to a subject in need thereof a personal health care composition comprising at least one nucleic acid aptamer, wherein the aptamer has a binding affinity for intercellular adhesion molecule 1 (ICAM-1) and wherein the aptamer is configured to reduce the binding of one or more human rhinoviruses to the intercellular adhesion molecule 1 (ICAM-1).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Aptamer composition comprising at least one oligonucleotide consisting of: deoxyribonucleotides, ribonucleotides, derivatives of deoxyribonucleotides, derivatives of ribonucleotides, and mixtures thereof, wherein the aptamer composition has a binding affinity for intercellular adhesion molecule 1 (ICAM-1) and wherein the aptamer is configured to reduce the binding of one or more human rhinoviruses to the intercellular adhesion molecule 1 (ICAM-1) and wherein the aptamer composition comprises
at least one oligonucleotide selected from the group consisting of oligonucleotides with at least 95% nucleotide sequence identity to sequences selected from the group consisting of SEQ ID NO: 1 to SEQ ID NO: 200.

2. The aptamer composition of claim 1, comprising at least one oligonucleotide selected from the group consisting of SEQ ID NO: 1 to SEQ ID NO: 200.

3. The aptamer composition of claim 2, comprising at least one oligonucleotide selected from the group consisting of SEQ ID NO: 2, SEQ ID NO: 4, SEQ ID NO: 5, SEQ ID NO: 7, and SEQ ID NO: 8.

4. The aptamer composition of claim 1, wherein the at least one oligonucleotide comprises natural or non-natural nucleobases.

5. The aptamer composition of claim 4, wherein the non-natural nucleobases are selected from the group comprising hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, and mixtures thereof.

6. The aptamer composition of claim 1, wherein the nucleosides of the at least one oligonucleotide are linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, and mixtures thereof.

7. The aptamer composition of claim 1, where the derivatives of ribonucleotides or the derivatives of deoxyribonucleotides are selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

8. The aptamer composition of claim 1, further comprising at least one polymeric material, wherein the at least one polymeric material is covalently linked to the at least one oligonucleotide.

9. The aptamer composition of claim 8, wherein the at least one polymeric material is polyethylene glycol.

10. The aptamer composition of claim 1, wherein the nucleotides at the 5'- and 3'-ends of the at least one oligonucleotide are inverted.

11. The aptamer composition of claim 1, wherein at least one nucleotide of the at least one oligonucleotide is fluorinated at the 2' position of the pentose group.

12. The aptamer composition of claim 1, wherein the pyrimidine nucleotides of the at least one oligonucleotide are fluorinated at the 2' position of the pentose group.

13. The aptamer composition of claim 1, wherein the at least one oligonucleotide is covalently or non-covalently attached to one or more active ingredients, wherein the one or more active ingredients are selected from the group consisting of: respiratory illness treatment agents, cold-treatment agents, flu-treatment agents, antiviral agents, antimicrobial agents, cooling agents, malodor absorbing agents, natural extracts, peptides, enzymes, pharmaceutical active ingredients, metal compounds, and combinations thereof.

14. Aptamer composition comprising at least one oligonucleotide consisting of: deoxyribonucleotides, ribonucleotides, derivatives of deoxyribonucleotides, derivatives of ribonucleotides, and mixtures thereof; wherein the aptamer has a binding affinity for the Ig-like C2-type 1 domain (SEQ ID NO: 215) of the intercellular adhesion molecule 1 (ICAM-1), any post-translationally modified versions of said domain, and mixtures thereof, wherein the aptamer composition comprises
   at least one oligonucleotide selected from the group consisting of oligonucleotides with at least 95% nucleotide sequence identity to sequences selected from the group consisting of SEQ ID NO: 1 to SEQ ID NO: 200.

15. The aptamer composition of claim 14, comprising at least one oligonucleotide selected from the group consisting of oligonucleotides selected from the group consisting of SEQ ID NO: 1 to SEQ ID NO: 200.

16. The aptamer composition of claim 14, comprising at least one oligonucleotide selected from the group consisting of SEQ ID NO: 2, SEQ ID NO: 4, SEQ ID NO: 5, SEQ ID NO: 7, and SEQ ID NO: 8.

17. Personal health care composition comprising at least one nucleic acid aptamer; wherein the nucleic acid aptamer has a binding affinity for intercellular adhesion molecule 1 (ICAM-1), and wherein the aptamer is configured to reduce the binding of one or more human rhinoviruses to the intercellular adhesion molecule 1 (ICAM-1) wherein the aptamer composition comprises
   at least one oligonucleotide selected from the group consisting of oligonucleotides with at least 95% nucleotide sequence identity to sequences selected from the group consisting of SEQ ID NO: 1 to SEQ ID NO: 200.

18. The personal health care composition of claim 17, comprising at least one oligonucleotide selected from the group consisting of oligonucleotides selected from the group consisting of SEQ ID NO: 1 to SEQ ID NO: 200.

19. The personal health care composition of claim 18, comprising at least one oligonucleotide selected from the group consisting of SEQ ID NO: 2, SEQ ID NO: 4, SEQ ID NO: 5, SEQ ID NO: 7, and SEQ ID NO: 8.

20. The personal health care composition of claim 17, wherein the at least one nucleic acid aptamer is covalently or non-covalently attached to one or more active ingredients, wherein said one or more active ingredients are selected from the group comprising: respiratory illness treatment agents, cold-treatment agents, flu-treatment agents, antiviral agents, antimicrobial agents, cooling agents, malodor absorbing agents, natural extracts, peptides, enzymes, pharmaceutical active ingredients, metal compounds, and mixtures thereof.

21. Method for delivering a personal health care composition to the upper respiratory tract comprising administering to a subject in need thereof the personal health care composition of claim 17.

22. The aptamer composition of claim 1, wherein the aptamer composition further comprises at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

23. The aptamer composition of claim 14, wherein the aptamer composition further comprises at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

24. The personal health care composition of claim 17, wherein the personal health care composition further comprises at least one oligonucleotide comprising one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

* * * * *

SEQUENCE LISTING

<160> NUMBER OF SEQ ID NOS: 236

<210> SEQ ID NO 1
<211> LENGTH: 80
<212> TYPE: RNA

<213> ORGANISM: Artificial Sequence
<220> FEATURE:
<223> OTHER INFORMATION: Synthetic aptamer sequences

<400> SEQUENCE: 1
gggugcaucg uuuacgcgau uagucugaua aacaaaaaga uuucgcuaaa aaucaaucug    60
cugcugagga aggauaugag                                                80

<210> SEQ ID NO 2
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 2
gggugcaucg uuuacgcaga uagcagcagg aaucaagcgg uaggagucua gcagaagcug    60
cugcugagga aggauaugag                                                80

<210> SEQ ID NO 3
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 3
gggugcaucg uuuacgcauu uucguuuuau uucaguuuaa uugcguuuag uaucuggcug    60
cugcugagga aggauaugag                                                80

<210> SEQ ID NO 4
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 4
gggugcaucg uuuacgcgca acauaaaaau uuaaagugcu caguugucaa ucuaugacug    60
cugcugagga aggauaugag                                                80

<210> SEQ ID NO 5
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 5
gggugcaucg uuuacgcgua aaugguccgc uauuaaaaga aaagaaugaa gucucagcug    60
cugcugagga aggauaugag                                                80

<210> SEQ ID NO 6
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 6
gggugcaucg uuuacgcuau uucauuugu uuuuuaauu uacuagugua aacaauccug      60
cugcugagga aggauaugag                                                80

```
<210> SEQ ID NO 7
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 7
gggugcaucg uuuacgcgua aauaaguaga uaaaguggca guuguuuuc cuuggaacug      60 cugcugagga aggauaugag                                                80

<210> SEQ ID NO 8
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 8
gggugcaucg uuuacgcgua aaauuaaag agauuaaggu ccuuaagcag uuuguccug       60 cugcugagga aggauaugag                                                80

<210> SEQ ID NO 9
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 9
gggugcaucg uuuacgcgua aaaaaucaa acuucagca aauuauuuau caacguccug      60
cugcugagga aggauaugag                                                80

<210> SEQ ID NO 10
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 10
gggugcaucg uuuacgcgua aauaaauua aaagaacuu cuucagcaau caauauccug      60
cugcugagga aggauaugag                                                80

<210> SEQ ID NO 11
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 11
gggugcaucg uuuacgcgua aauaaaaaug aaaaauuguc ucucagcuuu caaaguccug    60
cugcugagga aggauaugag                                                80

<210> SEQ ID NO 12
<211> LENGTH: 80
<212> TYPE: RNA
<213> ORGANISM: Artificial Sequence
<220> FEATURE:
<223> OTHER INFORMATION: Synthetic aptamer sequences
```

```
<400> SEQUENCE: 12
gggugcaucg uuuacgcgua aaaaaaaaau aucuucggag aauucagcaa uuuuauccug      60
cugcugagga aggauaugag                                                  80

<210> SEQ ID NO 13
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 13
gggugcaucg uuuacgcgua aaauuuuca ucucagcaau aaauccaaa gaauccacug        60 cugcugagga aggauaugag                                                  80

<210> SEQ ID NO 14
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 14
gggugcaucg uuuacgcgua aaauauauca gcaaaguagu uuaagccucc ucaguuucug      60
cugcugagga aggauaugag                                                  80

<210> SEQ ID NO 15
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 15
gggugcaucg uuuacgcgua aauuaugaaa aauacagcaa ggauuuaacc ucaguuucug      60
cugcugagga aggauaugag                                                  80

<210> SEQ ID NO 16
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 16
gggugcaucg uuuacgcgua aaauaaauaa aucuucaaag uacagaccuc gauuuuucug      60
cugcugagga aggauaugag                                                  80

<210> SEQ ID NO 17
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 17
gggugcaucg uuuacgcuua uagguauuag acauuuucaa uuaaagugaa uuagugucug      60
cugcugagga aggauaugag                                                  80

<210> SEQ ID NO 18
<211> LENGTH: 80
```

```
<212> TYPE: RNA
<213> ORGANISM: Artificial Sequence
<220> FEATURE:
<223> OTHER INFORMATION: Synthetic aptamer sequences

<400> SEQUENCE: 18
gggugcaucg uuuacgcgua aaaugugaca gcaggauaau aaaauaagua cucaguacug      60
cugcugagga aggauaugag                                                  80

<210> SEQ ID NO 19
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 19
gggugcaucg uuuacgcgua auuaagaaaa auaaaaguac ucugcaguuu uuauccacug      60
cugcugagga aggauaugag                                                  80

<210> SEQ ID NO 20
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 20
gggugcaucg uuuacgcgua aaaauaaaau uuucccagac caguuaucug ccuuaaacug      60
cugcugagga aggauaugag                                                  80

<210> SEQ ID NO 21
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 21
gggugcaucg uuuacgcgua aagaaaaaaa ucagcuuuua gucgccuucc auuuugacug      60
cugcugagga aggauaugag                                                  80

<210> SEQ ID NO 22
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 22
gggugcaucg uuuacgcgua aauaaauaau caaaauuaca cucaguggca auuccucug       60 cugcugagga aggauaugag                                                  80

<210> SEQ ID NO 23
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 23
gggugcaucg uuuacgcgua aaauacagga uacgacaaua acucagcaga uuuuauccug      60
```
cugcugagga aggauaugag                                          80

<210> SEQ ID NO 24
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 24
gggugcaucg uuuacgcguu aaaaauugug cacugagaug acgcagcauu aacuacacug    60
cugcugagga aggauaugag                                          80

<210> SEQ ID NO 25
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 25
gggugcaucg uuuacgcgua aauaaaaauu aaucagcaau uuccacuca guuguaccug    60 cugcugagga aggauaugag                                          80

<210> SEQ ID NO 26
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 26
gggugcaucg uuuacgcgua aaauaaaaa aucucgauca cugcaguuuu auuccggcug    60
cugcugagga aggauaugag                                          80

<210> SEQ ID NO 27
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 27
gggugcaucg uuuacgcgua aacaaauauc gauuaaaaua aaaucucagc aagaauccug    60
cugcugagga aggauaugag                                          80

<210> SEQ ID NO 28
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 28
gggugcaucg uuuacgcgua aaauaaauaa aauuauccca ggagcaaauu uucuucgcug    60
cugcugagga aggauaugag                                          80

<210> SEQ ID NO 29
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 29
gggugcaucg uuuacgcgua gaagaauuaa uaguggacau aucaauagca guuuauccug    60
cugcugagga aggauaugag                                               80

<210> SEQ ID NO 30
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 30
gggugcaucg uuuacgcgua aacauauuca gcaguuaaaa uuuaguaggu ucaguagcug    60
cugcugagga aggauaugag                                               80

<210> SEQ ID NO 31
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 31
gggugcaucg uuuacgcgua aaaagauaa aacuuaguug cagaauuugc cuucauucug    60
cugcugagga aggauaugag                                               80

<210> SEQ ID NO 32
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 32
gggugcaucg uuuacgcgua aaaguuuga uggaagcaga uuaguuuagu caaauuucug    60
cugcugagga aggauaugag                                               80

<210> SEQ ID NO 33
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 33
gggugcaucg uuuacgcgua aaaugaaaua aggaauccuu cagcaguauu uauccuucug    60
cugcugagga aggauaugag                                               80

<210> SEQ ID NO 34
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 34
gggugcaucg uuuacgcgua aagaauaaaa augacaaaau ucucagcuuu ugucaaccug    60
cugcugagga aggauaugag                                               80

<210> SEQ ID NO 35

```
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 35
gggugcaucg uuuacgcgua aaaaaugaaa ugaaaaaauu cucagcuguc uaucuuccug        60
cugcugagga aggauaugag                                                   80

<210> SEQ ID NO 36
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 36
gggugcaucg uuuacgcgua aauaaguaaa aaacucaguu uucaguuaag uauccaacug        60
cugcugagga aggauaugag                                                   80

<210> SEQ ID NO 37
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 37
gggugcaucg uuuacgcgua aauuucagca gaguaauaau aacacuucuu caguuugcug        60
cugcugagga aggauaugag                                                   80

<210> SEQ ID NO 38
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 38
gggugcaucg uuuacgcgua aaauuaagaa guauuaucag uuagcuuuuu cuuccaacug        60
cugcugagga aggauaugag                                                   80

<210> SEQ ID NO 39
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 39
gggugcaucg uuuacgcgua aauaaaaag uuuuccuauc agcaaacuca caaauuccug         60
cugcugagga aggauaugag                                                   80

<210> SEQ ID NO 40
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 40
gggugcaucg uuuacgcgua aaaugaaaug uaaaagaauu gaacuuggca gauuuuccug        60
```
cugcugagga aggauaugag                                              80

<210> SEQ ID NO 41
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 41
gggugcaucg uuuacgcgua aauuaaagua gcaguaauuu cagcaguuuu uaccucucug    60
cugcugagga aggauaugag                                              80

<210> SEQ ID NO 42
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 42
gggugcaucg uuuacgcgua aauaaaggau aaaauaauuu cagggcaguu ucucauccug    60
cugcugagga aggauaugag                                              80

<210> SEQ ID NO 43
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 43
gggugcaucg uuuacgcagg aucguuuuaa guaaaauaaa agauuuccuu gguaauccug    60
cugcugagga aggauaugag                                              80

<210> SEQ ID NO 44
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 44
gggugcaucg uuuacgcgua aaauaaagau caauuaaagg cuuugaucga uuuccucug     60 cugcugagga aggauaugag                                              80

<210> SEQ ID NO 45
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 45
gggugcaucg uuuacgcgua aaauuagag auuaaaauag uuccuuucag uuuuguccug     60
cugcugagga aggauaugag                                              80

<210> SEQ ID NO 46
<211> LENGTH: 80
<212> TYPE: RNA
<213> ORGANISM: Artificial Sequence
<220> FEATURE:

<223> OTHER INFORMATION: Synthetic aptamer sequences

<400> SEQUENCE: 46
gggugcaucg uuuacgcgua aaauugacaa ugugaaaagc agacagcaaa uauuccucug    60
cugcugagga aggauaugag    80

<210> SEQ ID NO 47
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 47
gggugcaucg uuuacgcgua aauaaccagu uauacagaaa gaucucagca auuuauccug    60
cugcugagga aggauaugag    80

<210> SEQ ID NO 48
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 48
gggugcaucg uuuacgcuua cagaaggauu gcaccacaug cguacucgau gaaacaccug    60
cugcugagga aggauaugag    80

<210> SEQ ID NO 49
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 49
gggugcaucg uuuacgcgua aaauaauaau uaaacucagc aaauucaauc caacuuucug    60
cugcugagga aggauaugag    80

<210> SEQ ID NO 50
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 50
gggugcaucg uuuacgcgua aacaagaaua aauucagcag ugguuuugau ccuuugacug    60
cugcugagga aggauaugag    80

<210> SEQ ID NO 51
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 51
gggugcaucg uuuacgcgua aauuaaucag auugaacaaa aguuucccu caguuuucug    60 cugcugagga aggauaugag    80

```
<210> SEQ ID NO 52
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 52
gggugcaucg uuuacgcgua aagaaaaaca ucagagcagu uauaauaguc cuuuuuccug    60
cugcugagga aggauaugag                                               80

<210> SEQ ID NO 53
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 53
gggugcaucg uuuacgcgua aagaaaauaa acuugaucaa acuuagcagu uuuuauccug    60
cugcugagga aggauaugag                                               80

<210> SEQ ID NO 54
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 54
gggugcaucg uuuacgcauu uucguuauau uucugguuuu uaugcgugag aauccugcug    60
cugcugagga aggauaugag                                               80

<210> SEQ ID NO 55
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 55
gggugcaucg uuuacgcgua aaaauaagau cucacagcga caaauuuuuc uuccagucug    60
cugcugagga aggauaugag                                               80

<210> SEQ ID NO 56
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 56
gggugcaucg uuuacgcgua aauuuaagac augacagcag acauuuuauc uucagaccug    60
cugcugagga aggauaugag                                               80

<210> SEQ ID NO 57
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 57
```

```
gggugcaucg uuuacgcgua auaacagaaa uauaacucag cugaauuaau uuuccgcug      60 cugcugagga aggauaugag                                                80
```

<210> SEQ ID NO 58
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 58

```
gggugcaucg uuuacgcgua aaaauaaauu ccaaaauauu cagcagaaau ccucgaacug      60
cugcugagga aggauaugag                                                80
```

<210> SEQ ID NO 59
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 59

```
gggugcaucg uuuacgcgua aaaauaauag guuccaauca agcaguacaa aauuccucug      60
cugcugagga aggauaugag                                                80
```

<210> SEQ ID NO 60
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 60

```
gggugcaucg uuuacgcgua aaaaucuaa aaagauauca gcaggcaaau uuccuucug       60 cugcugagga aggauaugag                                                80
```

<210> SEQ ID NO 61
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 61

```
gggugcaucg uuuacgcgua aaauaaagag gauaacuaca aucaucagca aucauaucug      60
cugcugagga aggauaugag                                                80
```

<210> SEQ ID NO 62
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 62

```
gggugcaucg uuuacgcgua aauuuaguag aaaggaaaga cgaaguuucc ucaguuucug      60
cugcugagga aggauaugag                                                80
```

<210> SEQ ID NO 63
<211> LENGTH: 80
<212> TYPE: RNA
<213> ORGANISM: Artificial Sequence

```
<220> FEATURE:
<223> OTHER INFORMATION: Synthetic aptamer sequences

<400> SEQUENCE: 63
gggugcaucg uuuacgcgua aaauaauag aucucagaau augaaagcag uucuuuccug      60
cugcugagga aggauaugag                                                80

<210> SEQ ID NO 64
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 64
gggugcaucg uuuacgcgua acaagauauu cacagcagau uuuaaaaaau uccucgucug     60
cugcugagga aggauaugag                                                80

<210> SEQ ID NO 65
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 65
gggugcaucg uuuacgcgua aaaguugac aauuaauaaa aucuucuuag cauuuuccug     60
cugcugagga aggauaugag                                                80

<210> SEQ ID NO 66
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 66
gggugcaucg uuuacgcgua aaacaaaaug aaacuuauag cucagcauau uuugauccug    60
cugcugagga aggauaugag                                                80

<210> SEQ ID NO 67
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 67
gggugcaucg uuuacgcgua aauuaucaaa aaagcagauu uaaguauacc ucaguuacug    60
cugcugagga aggauaugag                                                80

<210> SEQ ID NO 68
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 68
gggugcaucg uuuacgcgua aauaaaauag cucagcaagg aaguuuuuuu ccucaaacug    60
cugcugagga aggauaugag                                                80
```

```
<210> SEQ ID NO 69
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 69
gggugcaucg uuuacgcgua aauuugagaa aagaacagca gacucaaauc uuuuuaacug      60
cugcugagga aggauaugag                                                 80

<210> SEQ ID NO 70
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 70
gggugcaucg uuuacgcgua acagaaaauu aagcucagca auaguaauua uccuagucug      60
cugcugagga aggauaugag                                                 80

<210> SEQ ID NO 71
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 71
gggugcaucg uuuacgcgua augaaaauaa aucagucuca cagcauuuua aaacuuccug      60
cugcugagga aggauaugag                                                 80

<210> SEQ ID NO 72
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 72
gggugcaucg uuuacgcgua uuuacaagca acaaaguuac aaucagcaga auuuauccug      60
cugcugagga aggauaugag                                                 80

<210> SEQ ID NO 73
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 73
gggugcaucg uuuacgcgua aaaaauuguc uauagcacuu uuagauuccc aaacuaacug      60
cugcugagga aggauaugag                                                 80

<210> SEQ ID NO 74
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 74
```

```
gggugcaucg uuuacgcgua aaaaaaucag caaaaucgaa aacucaugca guuuguccug    60
cugcugagga aggauaugag                                                80
```

<210> SEQ ID NO 75
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 75

```
gggugcaucg uuuacgcgua aaaaauuccu uaaaaauuua acuaacugga uaggucucug    60
cugcugagga aggauaugag                                                80
```

<210> SEQ ID NO 76
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 76

```
gggugcaucg uuuacgcgua aaacaaaauu ucugacagca auccuucgu uaaaaaucug     60 cugcugagga aggauaugag                                                80
```

<210> SEQ ID NO 77
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 77

```
gggugcaucg uuuacgcgua aauuauuaaa aaaaucagca aaguuuauuu cccacggcug    60
cugcugagga aggauaugag                                                80
```

<210> SEQ ID NO 78
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 78

```
gggugcaucg uuuacgcgua auuaaucaaa caauagcagc aaaucucagc aauuuuccug    60
cugcugagga aggauaugag                                                80
```

<210> SEQ ID NO 79
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 79

```
gggugcaucg uuuacgcgua auuugaaagu cucauaaauu uuuuuuuuu uuucaaucug     60 cugcugagga aggauaugag                                                80
```

<210> SEQ ID NO 80
<211> LENGTH: 80
<212> TYPE: RNA

<213> ORGANISM: Artificial Sequence
<220> FEATURE:
<223> OTHER INFORMATION: Synthetic aptamer sequences

<400> SEQUENCE: 80
gggugcaucg uuuacgcgua aaaauucagc augauuucaa uuacuccuuu cauugaucug    60
cugcugagga aggauaugag                                               80

<210> SEQ ID NO 81
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 81
gggugcaucg uuuacgcgua aaauaaauaa aaucaguag caaucuuucu cacagugcug    60
cugcugagga aggauaugag                                               80

<210> SEQ ID NO 82
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 82
gggugcaucg uuuacgcgua aauaaaaagc agaucucagc aaaacucgua aauucaacug    60
cugcugagga aggauaugag                                               80

<210> SEQ ID NO 83
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 83
gggugcaucg uuuacgcgua aauaaugaag gacucagaca guuaaaagau gcauuaacug    60
cugcugagga aggauaugag                                               80

<210> SEQ ID NO 84
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 84
gggugcaucg uuuacgcgua aaaagauca auaugaaaau cagcaguuaa uaucuuccug    60
cugcugagga aggauaugag                                               80

<210> SEQ ID NO 85
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 85
gggugcaucg uuuacgcgua aaauaacaa acuucucagc uguuuaauau cuccugacug    60
cugcugagga aggauaugag                                               80

<210> SEQ ID NO 86
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 86
gggugcaucg uuuacgcgua aaauuaaaca aauagcucag cacgaaaauu ugcguaacug    60
cugcugagga aggauaugag                                                80

<210> SEQ ID NO 87
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 87
gggugcaucg uuuacgcgua auuaaaaaac cuucacacag aaaacauucc ucaauuucug    60
cugcugagga aggauaugag                                                80

<210> SEQ ID NO 88
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 88
gggugcaucg uuuacgcauu uucguuuuau uuuaguuuaa uugcguuuag uaucuggcug    60
cugcugagga aggauaugag                                                80

<210> SEQ ID NO 89
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 89
gggugcaucg uuuacgcgua aaaguauaa agguuagaaa uucagcaguu ugauauccug    60
cugcugagga aggauaugag                                                80

<210> SEQ ID NO 90
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 90
gggugcaucg uuuacgcgua aaaggagaa uuaguacuca ccagucguuu aaaauuucug    60
cugcugagga aggauaugag                                                80

<210> SEQ ID NO 91
<211> LENGTH: 80
<212> TYPE: RNA
<213> ORGANISM: Artificial Sequence
<220> FEATURE:
<223> OTHER INFORMATION: Synthetic aptamer sequences

```
<400> SEQUENCE: 91
gggugcaucg uuuacgcgua aaaauaaaua acuacgagau cucagcagau cauuauccug    60
cugcugagga aggauaugag                                                80

<210> SEQ ID NO 92
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 92
gggugcaucg uuuacgcgua aaaugguuuu ucagcaguua acauaaugcc ucaguuucug    60
cugcugagga aggauaugag                                                80

<210> SEQ ID NO 93
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 93
gggugcaucg uuuacgcgua aauaacaaaa aucucagcuu uugcagaauu uauccaccug    60
cugcugagga aggauaugag                                                80

<210> SEQ ID NO 94
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 94
gggugcaucg uuuacgcgua aauaaacuca cagcagaaaa aauuccuuca acuuguacug    60
cugcugagga aggauaugag                                                80

<210> SEQ ID NO 95
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 95
gggugcaucg uuuacgcagu aguuaauaac aaauagucag caguuuuguc cuucauucug    60
cugcugagga aggauaugag                                                80

<210> SEQ ID NO 96
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 96
gggugcaucg uuuacgcgua aaauagcag uagauagcgg caguuuugua uuguuacug     60 cugcugagga aggauaugag                                                80

<210> SEQ ID NO 97
<211> LENGTH: 80
```

```
<212> TYPE: RNA
<213> ORGANISM: Artificial Sequence
<220> FEATURE:
<223> OTHER INFORMATION: Synthetic aptamer sequences

<400> SEQUENCE: 97
gggugcaucg uuuacgcgua aaaauuuaaa uaacucagca aucauagauc cgacugacug    60
cugcugagga aggauaugag                                               80

<210> SEQ ID NO 98
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 98
gggugcaucg uuuacgcgua aagaacagcu gacaagaaau ucaaaccuuc agauuuucug    60
cugcugagga aggauaugag                                               80

<210> SEQ ID NO 99
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 99
gggugcaucg uuuacgcgua aagauaauaa gcaguauuca gcagauuugu aagguuucug    60
cugcugagga aggauaugag                                               80

<210> SEQ ID NO 100
<211> LENGTH: 80
<212> TYPE: RNA
<213> ORGANISM: Artificial Sequence
<220> FEATURE:
<223> OTHER INFORMATION: Synthetic aptamer sequences

<400> SEQUENCE: 100
gggugcaucg uuuacgcgua aauaagaggc agacaguauu acaaauaucc uaaaauacug    60
cugcugagga aggauaugag                                               80

<210> SEQ ID NO 101
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 101
gggtgcatcg tttacgcgat tagtctgata aacaaaaaga tttcgctaaa aatcaatctg    60
ctgctgagga aggatatgag                                               80

<210> SEQ ID NO 102
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 102
gggtgcatcg tttacgcaga tagcagcagg aatcaagcgg taggagtcta gcagaagctg    60
```

```
ctgctgagga aggatatgag                                              80
```

<210> SEQ ID NO 103
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 103

```
gggtgcatcg tttacgcatt ttcgttttat ttcagtttaa ttgcgtttag tatctggctg   60
ctgctgagga aggatatgag                                              80
```

<210> SEQ ID NO 104
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 104

```
gggtgcatcg tttacgcgca acataaaaat ttaaagtgct cagttgtcaa tctatgactg   60
ctgctgagga aggatatgag                                              80
```

<210> SEQ ID NO 105
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 105

```
gggtgcatcg tttacgcgta aatggtccgc tattaaaaga aagaatgaa gtctcagctg    60 ctgctgagga aggatatgag                                              80
```

<210> SEQ ID NO 106
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 106

```
gggtgcatcg tttacgctat tttcatttgt ttttttaatt tactagtgta aacaatcctg   60
ctgctgagga aggatatgag                                              80
```

<210> SEQ ID NO 107
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 107

```
gggtgcatcg tttacgcgta aataagtaga taaagtggca gtttgttttc cttggaactg   60
ctgctgagga aggatatgag                                              80
```

<210> SEQ ID NO 108
<211> LENGTH: 80
<212> TYPE: DNA
<213> ORGANISM: Artificial Sequence
<220> FEATURE:
<223> OTHER INFORMATION: Synthetic aptamer sequences

```
<400> SEQUENCE: 108
gggtgcatcg tttacgcgta aaaattaaag agattaaggt ccttaagcag ttttgtcctg      60
ctgctgagga aggatatgag                                                  80

<210> SEQ ID NO 109
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 109
gggtgcatcg tttacgcgta aaaaaatcaa aacttcagca aattatttat caacgtcctg      60
ctgctgagga aggatatgag                                                  80

<210> SEQ ID NO 110
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 110
gggtgcatcg tttacgcgta aaataaatta aaagaacttc cttcagcaat caatatcctg      60
ctgctgagga aggatatgag                                                  80

<210> SEQ ID NO 111
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 111
gggtgcatcg tttacgcgta aataaaaatg aaaaattgtc tctcagcttt caaagtcctg      60
ctgctgagga aggatatgag                                                  80

<210> SEQ ID NO 112
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 112
gggtgcatcg tttacgcgta aaaaaaaaat atcttcggag aattcagcaa ttttatcctg      60
ctgctgagga aggatatgag                                                  80

<210> SEQ ID NO 113
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 113
gggtgcatcg tttacgcgta aaaattttca tctcagcaat taaatccaaa gaatccactg      60
ctgctgagga aggatatgag                                                  80

<210> SEQ ID NO 114
```

```
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 114
gggtgcatcg tttacgcgta aaatatatca gcaaagtagt ttaagcctcc tcagtttctg    60
ctgctgagga aggatatgag                                                80

<210> SEQ ID NO 115
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 115
gggtgcatcg tttacgcgta aattatgaaa aatacagcaa ggatttaacc tcagtttctg    60
ctgctgagga aggatatgag                                                80

<210> SEQ ID NO 116
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 116
gggtgcatcg tttacgcgta aaataaataa atcttcaaag tacagacctc gattttctg     60 ctgctgagga aggatatgag                                                80

<210> SEQ ID NO 117
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 117
gggtgcatcg tttacgctta taggtattag acattttcaa ttaaagtgaa ttagtgtctg    60
ctgctgagga aggatatgag                                                80

<210> SEQ ID NO 118
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 118
gggtgcatcg tttacgcgta aaatgtgaca gcaggataat aaaataagta ctcagtactg    60
ctgctgagga aggatatgag                                                80

<210> SEQ ID NO 119
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 119
gggtgcatcg tttacgcgta attaagaaaa ataaaagtac tctgcagttt ttatccactg    60
```

```
ctgctgagga aggatatgag                                            80

<210> SEQ ID NO 120
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 120
gggtgcatcg tttacgcgta aaaataaaat tttcccagac cagttatctg ccttaaactg   60
ctgctgagga aggatatgag                                            80

<210> SEQ ID NO 121
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 121
gggtgcatcg tttacgcgta aagaaaaaaa tcagcttttta gtcgccttcc attttgactg   60
ctgctgagga aggatatgag                                            80

<210> SEQ ID NO 122
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 122
gggtgcatcg tttacgcgta aataaataat caaaattaca ctcagtggca atttcctctg   60
ctgctgagga aggatatgag                                            80

<210> SEQ ID NO 123
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 123
gggtgcatcg tttacgcgta aaatacagga tacgacaata actcagcaga ttttatcctg   60
ctgctgagga aggatatgag                                            80

<210> SEQ ID NO 124
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 124
gggtgcatcg tttacgcgtt aaaaattgtg cactgagatg acgcagcatt aactacactg   60
ctgctgagga aggatatgag                                            80

<210> SEQ ID NO 125
<211> LENGTH: 80
<212> TYPE: DNA
<213> ORGANISM: Artificial Sequence
<220> FEATURE:
```

<223> OTHER INFORMATION: Synthetic aptamer sequences

<400> SEQUENCE: 125
gggtgcatcg tttacgcgta aataaaaatt aatcagcaat tttccactca gttgtacctg    60
ctgctgagga aggatatgag                                                80

<210> SEQ ID NO 126
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 126
gggtgcatcg tttacgcgta aaataaaaa atctcgatca ctgcagtttt attccggctg     60
ctgctgagga aggatatgag                                                80

<210> SEQ ID NO 127
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 127
gggtgcatcg tttacgcgta aacaaatatc gattaaaata aatctcagc aagaatcctg     60 ctgctgagga aggatatgag                                                80

<210> SEQ ID NO 128
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 128
gggtgcatcg tttacgcgta aaataaataa aattatccca ggagcaaatt ttcttcgctg    60
ctgctgagga aggatatgag                                                80

<210> SEQ ID NO 129
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 129
gggtgcatcg tttacgcgta gaagaattaa tagtggacat atcaatagca gtttatcctg    60
ctgctgagga aggatatgag                                                80

<210> SEQ ID NO 130
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 130
gggtgcatcg tttacgcgta aacatattca gcagttaaaa tttagtaggt tcagtagctg    60
ctgctgagga aggatatgag                                                80

```
<210> SEQ ID NO 131
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 131
gggtgcatcg tttacgcgta aaaaagataa aacttagttg cagaatttgc cttcattctg    60
ctgctgagga aggatatgag                                                80

<210> SEQ ID NO 132
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 132
gggtgcatcg tttacgcgta aaaagtttga tggaagcaga ttagtttagt caaatttctg    60
ctgctgagga aggatatgag                                                80

<210> SEQ ID NO 133
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 133
gggtgcatcg tttacgcgta aaatgaaata aggaatcctt cagcagtatt tatccttctg    60
ctgctgagga aggatatgag                                                80

<210> SEQ ID NO 134
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 134
gggtgcatcg tttacgcgta aagaataaaa atgacaaaat tctcagcttt tgtcaacctg    60
ctgctgagga aggatatgag                                                80

<210> SEQ ID NO 135
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 135
gggtgcatcg tttacgcgta aaaatgaaa tgaaaaaatt ctcagctgtc tatcttcctg     60
ctgctgagga aggatatgag                                                80

<210> SEQ ID NO 136
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 136
```

```
gggtgcatcg tttacgcgta aataagtaaa aaactcagtt ttcagttaag tatccaactg    60
ctgctgagga aggatatgag                                                80

<210> SEQ ID NO 137
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 137
gggtgcatcg tttacgcgta aatttcagca gagtaataat aacacttctt cagtttgctg    60
ctgctgagga aggatatgag                                                80

<210> SEQ ID NO 138
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 138
gggtgcatcg tttacgcgta aaattaagaa gtattatcag ttagcttttt cttccaactg    60
ctgctgagga aggatatgag                                                80

<210> SEQ ID NO 139
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 139
gggtgcatcg tttacgcgta aaataaaaag ttttcctatc agcaaactca caaattcctg    60
ctgctgagga aggatatgag                                                80

<210> SEQ ID NO 140
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 140
gggtgcatcg tttacgcgta aaatgaaatg taaaagaatt gaacttggca gattttcctg    60
ctgctgagga aggatatgag                                                80

<210> SEQ ID NO 141
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 141
gggtgcatcg tttacgcgta aattaaagta gcagtaattt cagcagtttt tacctctctg    60
ctgctgagga aggatatgag                                                80

<210> SEQ ID NO 142
<211> LENGTH: 80
<212> TYPE: DNA
<213> ORGANISM: Artificial Sequence
```

<220> FEATURE:
<223> OTHER INFORMATION: Synthetic aptamer sequences

<400> SEQUENCE: 142
gggtgcatcg tttacgcgta aataaggat aaaataattt cagggcagtt tctcatcctg    60
ctgctgagga aggatatgag                                               80

<210> SEQ ID NO 143
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 143
gggtgcatcg tttacgcagg atcgttttaa gtaaataaa agatttcctt ggtaatcctg    60
ctgctgagga aggatatgag                                               80

<210> SEQ ID NO 144
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 144
gggtgcatcg tttacgcgta aaataaagat caattaaagg ctttgatcga ttttcctctg   60
ctgctgagga aggatatgag                                               80

<210> SEQ ID NO 145
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 145
gggtgcatcg tttacgcgta aaaattagag attaaaatag ttcctttcag ttttgtcctg   60
ctgctgagga aggatatgag                                               80

<210> SEQ ID NO 146
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 146
gggtgcatcg tttacgcgta aaattgacaa tgtgaaaagc agacagcaaa tattcctctg   60
ctgctgagga aggatatgag                                               80

<210> SEQ ID NO 147
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 147
gggtgcatcg tttacgcgta aataaccagt tatacagaaa gatctcagca atttatcctg   60
ctgctgagga aggatatgag                                               80

<210> SEQ ID NO 148
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 148
gggtgcatcg tttacgctta cagaaggatt gcaccacatg cgtactcgat gaaacacctg    60
ctgctgagga aggatatgag                                                80

<210> SEQ ID NO 149
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 149
gggtgcatcg tttacgcgta aaataataat taaactcagc aaattcaatc caactttctg    60
ctgctgagga aggatatgag                                                80

<210> SEQ ID NO 150
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 150
gggtgcatcg tttacgcgta aacaagaata aattcagcag tggttttgat cctttgactg    60
ctgctgagga aggatatgag                                                80

<210> SEQ ID NO 151
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 151
gggtgcatcg tttacgcgta aattaatcag attgaacaaa agttttccct cagttttctg    60
ctgctgagga aggatatgag                                                80

<210> SEQ ID NO 152
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 152
gggtgcatcg tttacgcgta aagaaaaaca tcagagcagt tataatagtc ctttttcctg    60
ctgctgagga aggatatgag                                                80

<210> SEQ ID NO 153
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 153
gggtgcatcg tttacgcgta aagaaaataa acttgatcaa acttagcagt ttttatcctg    60
ctgctgagga aggatatgag                                                80

<210> SEQ ID NO 154
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 154
gggtgcatcg tttacgcatt ttcgttatat ttctggtttt tatgcgtgag aatcctgctg    60
ctgctgagga aggatatgag                                                80

<210> SEQ ID NO 155
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 155
gggtgcatcg tttacgcgta aaaataagat ctcacagcga caaattttc ttccagtctg     60 ctgctgagga aggatatgag                                                80

<210> SEQ ID NO 156
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 156
gggtgcatcg tttacgcgta aatttaagac atgacagcag acattttatc ttcagacctg    60
ctgctgagga aggatatgag                                                80

<210> SEQ ID NO 157
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 157
gggtgcatcg tttacgcgta ataacagaaa tataactcag ctgaattaat ttttccgctg    60
ctgctgagga aggatatgag                                                80

<210> SEQ ID NO 158
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 158
gggtgcatcg tttacgcgta aaaataaatt ccaaaatatt cagcagaaat cctcgaactg    60
ctgctgagga aggatatgag                                                80

<210> SEQ ID NO 159
<211> LENGTH: 80
<212> TYPE: DNA

```
<213> ORGANISM: Artificial Sequence
<220> FEATURE:
<223> OTHER INFORMATION: Synthetic aptamer sequences

<400> SEQUENCE: 159
gggtgcatcg tttacgcgta aaaataatag gttccaatca agcagtacaa aattcctctg    60
ctgctgagga aggatatgag                                                80

<210> SEQ ID NO 160
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 160
gggtgcatcg tttacgcgta aaaaatctaa aaagatatca gcaggcaaat tttccttctg    60
ctgctgagga aggatatgag                                                80

<210> SEQ ID NO 161
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 161
gggtgcatcg tttacgcgta aaataaagag gataactaca atcatcagca atcatatctg    60
ctgctgagga aggatatgag                                                80

<210> SEQ ID NO 162
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 162
gggtgcatcg tttacgcgta aatttagtag aaaggaaaga cgaagtttcc tcagtttctg    60
ctgctgagga aggatatgag                                                80

<210> SEQ ID NO 163
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 163
gggtgcatcg tttacgcgta aaaataatag atctcagaat atgaaagcag ttctttcctg    60
ctgctgagga aggatatgag                                                80

<210> SEQ ID NO 164
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 164
gggtgcatcg tttacgcgta acaagatatt cacagcagat tttaaaaaat tcctcgtctg    60
ctgctgagga aggatatgag                                                80
```

<210> SEQ ID NO 165
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 165
gggtgcatcg tttacgcgta aaaagttgac aattaataaa atcttcttag cattttcctg    60
ctgctgagga aggatatgag                                                80

<210> SEQ ID NO 166
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 166
gggtgcatcg tttacgcgta aaacaaaatg aaacttatag ctcagcatat tttgatcctg    60
ctgctgagga aggatatgag                                                80

<210> SEQ ID NO 167
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 167
gggtgcatcg tttacgcgta aattatcaaa aaagcagatt taagtatacc tcagttactg    60
ctgctgagga aggatatgag                                                80

<210> SEQ ID NO 168
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 168
gggtgcatcg tttacgcgta aataaaatag ctcagcaagg aagttttttt cctcaaactg    60
ctgctgagga aggatatgag                                                80

<210> SEQ ID NO 169
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 169
gggtgcatcg tttacgcgta aatttgagaa aagaacagca gactcaaatc tttttaactg    60
ctgctgagga aggatatgag                                                80

<210> SEQ ID NO 170
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 170
gggtgcatcg tttacgcgta acagaaaatt aagctcagca atagtaatta tcctagtctg    60
ctgctgagga aggatatgag                                                80

<210> SEQ ID NO 171
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 171
gggtgcatcg tttacgcgta atgaaaataa atcagtctca cagcatttta aaacttcctg    60
ctgctgagga aggatatgag                                                80

<210> SEQ ID NO 172
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 172
gggtgcatcg tttacgcgta tttacaagca acaaagttac aatcagcaga atttatcctg    60
ctgctgagga aggatatgag                                                80

<210> SEQ ID NO 173
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 173
gggtgcatcg tttacgcgta aaaaattgtc tatagcactt ttagattccc aaactaactg    60
ctgctgagga aggatatgag                                                80

<210> SEQ ID NO 174
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 174
gggtgcatcg tttacgcgta aaaaaatcag caaaatcgaa aactcatgca gtttgtcctg    60
ctgctgagga aggatatgag                                                80

<210> SEQ ID NO 175
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 175
gggtgcatcg tttacgcgta aaaaattcct taaaaattta actaactgga taggtctctg    60
ctgctgagga aggatatgag                                                80

<210> SEQ ID NO 176
<211> LENGTH: 80

```
<212> TYPE: DNA
<213> ORGANISM: Artificial Sequence
<220> FEATURE:
<223> OTHER INFORMATION: Synthetic aptamer sequences

<400> SEQUENCE: 176
gggtgcatcg tttacgcgta aaacaaaatt tctgacagca attccttcgt taaaaatctg    60
ctgctgagga aggatatgag                                                80

<210> SEQ ID NO 177
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 177
gggtgcatcg tttacgcgta aattattaaa aaaatcagca agtttatttt cccacggctg    60
ctgctgagga aggatatgag                                                80

<210> SEQ ID NO 178
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 178
gggtgcatcg tttacgcgta attaatcaaa caatagcagc aaatctcagc aattttcctg    60
ctgctgagga aggatatgag                                                80

<210> SEQ ID NO 179
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 179
gggtgcatcg tttacgcgta atttgaaagt ctcataaatt tttttttttt tttcaatctg    60
ctgctgagga aggatatgag                                                80

<210> SEQ ID NO 180
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 180
gggtgcatcg tttacgcgta aaaattcagc atgatttcaa ttactccttt cattgatctg    60
ctgctgagga aggatatgag                                                80

<210> SEQ ID NO 181
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 181
gggtgcatcg tttacgcgta aaataaataa aaatcagtag caatctttct cacagtgctg    60
```
ctgctgagga aggatatgag                                                80

<210> SEQ ID NO 182
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 182
gggtgcatcg tttacgcgta aataaaaagc agatctcagc aaaactcgta aattcaactg    60
ctgctgagga aggatatgag                                                80

<210> SEQ ID NO 183
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 183
gggtgcatcg tttacgcgta aataatgaag gactcagaca gttaaaagat gcattaactg    60
ctgctgagga aggatatgag                                                80

<210> SEQ ID NO 184
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 184
gggtgcatcg tttacgcgta aaaagatca atatgaaaat cagcagttaa tatcttcctg    60
ctgctgagga aggatatgag                                                80

<210> SEQ ID NO 185
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 185
gggtgcatcg tttacgcgta aaaataacaa acttctcagc tgtttaatat ctcctgactg    60
ctgctgagga aggatatgag                                                80

<210> SEQ ID NO 186
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 186
gggtgcatcg tttacgcgta aaattaaaca aatagctcag cacgaaaatt tgcgtaactg    60
ctgctgagga aggatatgag                                                80

<210> SEQ ID NO 187
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 187
gggtgcatcg tttacgcgta attaaaaaac cttcacacag aaaacattcc tcaatttctg    60
ctgctgagga aggatatgag                                                80

<210> SEQ ID NO 188
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 188
gggtgcatcg tttacgcatt ttcgttttat tttagtttaa ttgcgtttag tatctggctg    60
ctgctgagga aggatatgag                                                80

<210> SEQ ID NO 189
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 189
gggtgcatcg tttacgcgta aaaagtataa aggttagaaa ttcagcagtt tgatatcctg    60
ctgctgagga aggatatgag                                                80

<210> SEQ ID NO 190
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 190
gggtgcatcg tttacgcgta aaaaggagaa ttagtactca ccagtcgttt aaaatttctg    60
ctgctgagga aggatatgag                                                80

<210> SEQ ID NO 191
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 191
gggtgcatcg tttacgcgta aaaataaata actacgagat ctcagcagat cattatcctg    60
ctgctgagga aggatatgag                                                80

<210> SEQ ID NO 192
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 192
gggtgcatcg tttacgcgta aaatggtttt tcagcagtta acataatgcc tcagtttctg    60
ctgctgagga aggatatgag                                                80

<210> SEQ ID NO 193

```
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 193
gggtgcatcg tttacgcgta aataacaaaa atctcagctt ttgcagaatt tatccacctg    60
ctgctgagga aggatatgag                                                80

<210> SEQ ID NO 194
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 194
gggtgcatcg tttacgcgta aataaactca cagcagaaaa aattccttca acttgtactg    60
ctgctgagga aggatatgag                                                80

<210> SEQ ID NO 195
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 195
gggtgcatcg tttacgcagt agttaataac aaatagtcag cagttttgtc cttcattctg    60
ctgctgagga aggatatgag                                                80

<210> SEQ ID NO 196
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 196
gggtgcatcg tttacgcgta aaaatagcag tagatagcgg cagttttgta tttgttactg    60
ctgctgagga aggatatgag                                                80

<210> SEQ ID NO 197
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 197
gggtgcatcg tttacgcgta aaaatttaaa taactcagca atcatagatc cgactgactg    60
ctgctgagga aggatatgag                                                80

<210> SEQ ID NO 198
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 198
gggtgcatcg tttacgcgta aagaacagct gacaagaaat tcaaaccttc agattttctg    60
```
ctgctgagga aggatatgag            80

<210> SEQ ID NO 199
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 199
gggtgcatcg tttacgcgta aagataataa gcagtattca gcagatttgt aaggtttctg       60
ctgctgagga aggatatgag            80

<210> SEQ ID NO 200
<211> LENGTH: 80
<212> TYPE: DNA
<213> ORGANISM: Artificial Sequence
<220> FEATURE:
<223> OTHER INFORMATION: Synthetic aptamer sequences

<400> SEQUENCE: 200
gggtgcatcg tttacgcgta aataagaggc agacagtatt acaaatatcc taaaatactg       60
ctgctgagga aggatatgag            80

<210> SEQ ID NO 201
<211> LENGTH: 11
<212> TYPE: RNA
<213> ORGANISM: Artificial Sequence
<220> FEATURE:
<223> OTHER INFORMATION: Synthetic aptamer sequences

<400> SEQUENCE: 201
aaacaaaaag a            11

<210> SEQ ID NO 202
<211> LENGTH: 10
<212> TYPE: RNA
<213> ORGANISM: Artificial Sequence
<220> FEATURE:
<223> OTHER INFORMATION: Synthetic aptamer sequences
<220> FEATURE:
<221> NAME/KEY: misc_feature
<222> LOCATION: (10)..(10)
<223> OTHER INFORMATION: n is a, c, g, or u

<400> SEQUENCE: 202 uaaaaaucan            10

<210> SEQ ID NO 203
<211> LENGTH: 11
<212> TYPE: DNA
<213> ORGANISM: Artificial Sequence
<220> FEATURE:
<223> OTHER INFORMATION: Synthetic aptamer sequences

<400> SEQUENCE: 203
aaacaaaaag a            11

<210> SEQ ID NO 204
<211> LENGTH: 10
<212> TYPE: DNA
<213> ORGANISM: Artificial Sequence
<220> FEATURE:
<223> OTHER INFORMATION: Synthetic aptamer sequences
<220> FEATURE:

```
<221> NAME/KEY: misc_feature
<222> LOCATION: (10)..(10)
<223> OTHER INFORMATION: n is a, c, g, or t

<400> SEQUENCE: 204 taaaaatcan                                                           10

<210> SEQ ID NO 205
<211> LENGTH: 13
<212> TYPE: RNA
<213> ORGANISM: Artificial Sequence
<220> FEATURE:
<223> OTHER INFORMATION: Synthetic aptamer sequences

<400> SEQUENCE: 205
auaaaaauuu aaa                                                       13

<210> SEQ ID NO 206
<211> LENGTH: 13
<212> TYPE: DNA
<213> ORGANISM: Artificial Sequence
<220> FEATURE:
<223> OTHER INFORMATION: Synthetic aptamer sequences

<400> SEQUENCE: 206
ataaaaattt aaa                                                       13

<210> SEQ ID NO 207
<211> LENGTH: 12
<212> TYPE: RNA
<213> ORGANISM: Artificial Sequence
<220> FEATURE:
<223> OTHER INFORMATION: Synthetic aptamer sequences

<400> SEQUENCE: 207
guaaaaauua aa                                                        12

<210> SEQ ID NO 208
<211> LENGTH: 12
<212> TYPE: DNA
<213> ORGANISM: Artificial Sequence
<220> FEATURE:
<223> OTHER INFORMATION: Synthetic aptamer sequences

<400> SEQUENCE: 208
gtaaaaatta aa                                                        12

<210> SEQ ID NO 209
<211> LENGTH: 10
<212> TYPE: RNA
<213> ORGANISM: Artificial Sequence
<220> FEATURE:
<223> OTHER INFORMATION: Synthetic aptamer sequences
<220> FEATURE:
<221> NAME/KEY: misc_feature
<222> LOCATION: (10)..(10)
<223> OTHER INFORMATION: n is a, c, g, or u

<400> SEQUENCE: 209 guaaaaaaan                                                           10

<210> SEQ ID NO 210
<211> LENGTH: 10
<212> TYPE: RNA
<213> ORGANISM: Artificial Sequence
<220> FEATURE:
<223> OTHER INFORMATION: Synthetic aptamer sequences
```

```
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u

<400> SEQUENCE: 210 unagcanuuu                                                                10

<210> SEQ ID NO 211
<211> LENGTH: 10
<212> TYPE: DNA
<213> ORGANISM: Artificial Sequence
<220> FEATURE:
<223> OTHER INFORMATION: Synthetic aptamer sequences
<220> FEATURE:
<221> NAME/KEY: misc_feature
<222> LOCATION: (10)..(10)
<223> OTHER INFORMATION: n is a, c, g, or t

<400> SEQUENCE: 211 gtaaaaaaan                                                                10

<210> SEQ ID NO 212
<211> LENGTH: 10
<212> TYPE: DNA
<213> ORGANISM: Artificial Sequence
<220> FEATURE:
<223> OTHER INFORMATION: Synthetic aptamer sequences
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 212 tnagcantttt                                                               10

<210> SEQ ID NO 213
<211> LENGTH: 532
<212> TYPE: PRT
<213> ORGANISM: Homo sapiens

<400> SEQUENCE: 213

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
```

-continued

```
            115                 120                 125
Lys Asn Leu Thr Leu Arg Cys Gln Val Glu Gly Gly Ala Pro Arg Ala
        130                 135                 140
Asn Leu Thr Val Val Leu Leu Arg Gly Glu Lys Glu Leu Lys Arg Glu
145                 150                 155                 160
Pro Ala Val Gly Glu Pro Ala Glu Val Thr Thr Val Leu Val Arg
                165                 170                 175
Arg Asp His His Gly Ala Asn Phe Ser Cys Arg Thr Glu Leu Asp Leu
                180                 185                 190
Arg Pro Gln Gly Leu Glu Leu Phe Glu Asn Thr Ser Ala Pro Tyr Gln
                195                 200                 205
Leu Gln Thr Phe Val Leu Pro Ala Thr Pro Gln Leu Val Ser Pro
    210                 215                 220
Arg Val Leu Glu Val Asp Thr Gln Gly Thr Val Val Cys Ser Leu Asp
225                 230                 235                 240
Gly Leu Phe Pro Val Ser Glu Ala Gln Val His Leu Ala Leu Gly Asp
                245                 250                 255
Gln Arg Leu Asn Pro Thr Val Thr Tyr Gly Asn Asp Ser Phe Ser Ala
                260                 265                 270
Lys Ala Ser Val Ser Val Thr Ala Glu Asp Glu Gly Thr Gln Arg Leu
                275                 280                 285
Thr Cys Ala Val Ile Leu Gly Asn Gln Ser Gln Glu Thr Leu Gln Thr
                290                 295                 300
Val Thr Ile Tyr Ser Phe Pro Ala Pro Asn Val Ile Leu Thr Lys Pro
305                 310                 315                 320
Glu Val Ser Glu Gly Thr Glu Val Thr Val Lys Cys Glu Ala His Pro
                325                 330                 335
Arg Ala Lys Val Thr Leu Asn Gly Val Pro Ala Gln Pro Leu Gly Pro
                340                 345                 350
Arg Ala Gln Leu Leu Leu Lys Ala Thr Pro Glu Asp Asn Gly Arg Ser
                355                 360                 365
Phe Ser Cys Ser Ala Thr Leu Glu Val Ala Gly Gln Leu Ile His Lys
    370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
                405                 410                 415
Pro Met Cys Gln Ala Trp Gly Asn Pro Leu Pro Glu Leu Lys Cys Leu
                420                 425                 430
Lys Asp Gly Thr Phe Pro Leu Pro Ile Gly Glu Ser Val Thr Val Thr
                435                 440                 445
Arg Asp Leu Glu Gly Thr Tyr Leu Cys Arg Ala Arg Ser Thr Gln Gly
    450                 455                 460
Glu Val Thr Arg Lys Val Thr Val Asn Val Leu Ser Pro Arg Tyr Glu
465                 470                 475                 480
Ile Val Ile Ile Thr Val Val Ala Ala Val Ile Met Gly Thr Ala
                485                 490                 495
Gly Leu Ser Thr Tyr Leu Tyr Asn Arg Gln Arg Lys Ile Lys Lys Tyr
                500                 505                 510
Arg Leu Gln Gln Ala Gln Lys Gly Thr Pro Met Lys Pro Asn Thr Gln
                515                 520                 525
Ala Thr Pro Pro
    530
```

<210> SEQ ID NO 214
<211> LENGTH: 453
<212> TYPE: PRT
<213> ORGANISM: Homo sapiens

<400> SEQUENCE: 214

```
Gln Thr Ser Val Ser Pro Ser Lys Val Ile Leu Pro Arg Gly Gly Ser
1               5                   10                  15

Val Leu Val Thr Cys Ser Thr Ser Cys Asp Gln Pro Lys Leu Leu Gly
            20                  25                  30

Ile Glu Thr Pro Leu Pro Lys Lys Glu Leu Leu Leu Pro Gly Asn Asn
        35                  40                  45

Arg Lys Val Tyr Glu Leu Ser Asn Val Gln Glu Asp Ser Gln Pro Met
    50                  55                  60

Cys Tyr Ser Asn Cys Pro Asp Gly Gln Ser Thr Ala Lys Thr Phe Leu
65                  70                  75                  80

Thr Val Tyr Trp Thr Pro Glu Arg Val Glu Leu Ala Pro Leu Pro Ser
                85                  90                  95

Trp Gln Pro Val Gly Lys Asn Leu Thr Leu Arg Cys Gln Val Glu Gly
            100                 105                 110

Gly Ala Pro Arg Ala Asn Leu Thr Val Val Leu Arg Gly Glu Lys
        115                 120                 125

Glu Leu Lys Arg Glu Pro Ala Val Gly Glu Pro Ala Glu Val Thr Thr
    130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
    290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Leu Lys Ala Thr Pro Glu
                325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
        355                 360                 365

Pro Arg Leu Asp Glu Arg Asp Cys Pro Gly Asn Trp Thr Trp Pro Glu
```

```
             370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
                405                 410                 415

Ser Val Thr Val Thr Arg Asp Leu Glu Gly Thr Tyr Leu Cys Arg Ala
                420                 425                 430

Arg Ser Thr Gln Gly Glu Val Thr Arg Lys Val Thr Val Asn Val Leu
                435                 440                 445

Ser Pro Arg Tyr Glu
            450

<210> SEQ ID NO 215
<211> LENGTH: 63
<212> TYPE: PRT
<213> ORGANISM: Homo sapiens

<400> SEQUENCE: 215

Gly Gly Ser Val Leu Val Thr Cys Ser Thr Ser Cys Asp Gln Pro Lys
1               5                   10                  15

Leu Leu Gly Ile Glu Thr Pro Leu Pro Lys Lys Glu Leu Leu Leu Pro
                20                  25                  30

Gly Asn Asn Arg Lys Val Tyr Glu Leu Ser Asn Val Gln Glu Asp Ser
                35                  40                  45

Gln Pro Met Cys Tyr Ser Asn Cys Pro Asp Gly Gln Ser Thr Ala
            50                  55                  60

<210> SEQ ID NO 216
<211> LENGTH: 66
<212> TYPE: PRT
<213> ORGANISM: Homo sapiens

<400> SEQUENCE: 216

Gly Lys Asn Leu Thr Leu Arg Cys Gln Val Glu Gly Gly Ala Pro Arg
1               5                   10                  15

Ala Asn Leu Thr Val Val Leu Leu Arg Gly Glu Lys Glu Leu Lys Arg
                20                  25                  30

Glu Pro Ala Val Gly Glu Pro Ala Glu Val Thr Thr Thr Val Leu Val
                35                  40                  45

Arg Arg Asp His His Gly Ala Asn Phe Ser Cys Arg Thr Glu Leu Asp
            50                  55                  60

Leu Arg
65

<210> SEQ ID NO 217
<211> LENGTH: 68
<212> TYPE: PRT
<213> ORGANISM: Homo sapiens

<400> SEQUENCE: 217

Asp Thr Gln Gly Thr Val Val Cys Ser Leu Asp Gly Leu Phe Pro Val
1               5                   10                  15

Ser Glu Ala Gln Val His Leu Ala Leu Gly Asp Gln Arg Leu Asn Pro
                20                  25                  30

Thr Val Thr Tyr Gly Asn Asp Ser Phe Ser Ala Lys Ala Ser Val Ser
                35                  40                  45

Val Thr Ala Glu Asp Glu Gly Thr Gln Arg Leu Thr Cys Ala Val Ile
            50                  55                  60
```

Leu Gly Asn Gln
65

<210> SEQ ID NO 218
<211> LENGTH: 54
<212> TYPE: PRT
<213> ORGANISM: Homo sapiens

<400> SEQUENCE: 218

Gly Thr Glu Val Thr Val Lys Cys Glu Ala His Pro Arg Ala Lys Val
1               5                   10                  15

Thr Leu Asn Gly Val Pro Ala Gln Pro Leu Gly Pro Arg Ala Gln Leu
            20                  25                  30

Leu Leu Lys Ala Thr Pro Glu Asp Asn Gly Arg Ser Phe Ser Cys Ser
        35                  40                  45

Ala Thr Leu Glu Val Ala
    50

<210> SEQ ID NO 219
<211> LENGTH: 53
<212> TYPE: PRT
<213> ORGANISM: Homo sapiens

<400> SEQUENCE: 219

Asn Ser Gln Gln Thr Pro Met Cys Gln Ala Trp Gly Asn Pro Leu Pro
1               5                   10                  15

Glu Leu Lys Cys Leu Lys Asp Gly Thr Phe Pro Leu Pro Ile Gly Glu
            20                  25                  30

Ser Val Thr Val Thr Arg Asp Leu Glu Gly Thr Tyr Leu Cys Arg Ala
        35                  40                  45

Arg Ser Thr Gln Gly
    50

<210> SEQ ID NO 220
<211> LENGTH: 13
<212> TYPE: PRT
<213> ORGANISM: Homo sapiens

<400> SEQUENCE: 220

Gln Thr Ser Val Ser Pro Ser Lys Val Ile Leu Pro Arg
1               5                   10

<210> SEQ ID NO 221
<211> LENGTH: 10
<212> TYPE: PRT
<213> ORGANISM: Homo sapiens

<400> SEQUENCE: 221

Ser Cys Asp Gln Pro Lys Leu Leu Gly Ile
1               5                   10

<210> SEQ ID NO 222
<211> LENGTH: 16
<212> TYPE: PRT
<213> ORGANISM: Homo sapiens

<400> SEQUENCE: 222

Pro Lys Lys Glu Leu Leu Leu Pro Gly Asn Asn Arg Lys Val Tyr Glu
1               5                   10                  15

<210> SEQ ID NO 223

```
<211> LENGTH: 15
<212> TYPE: PRT
<213> ORGANISM: Homo sapiens

<400> SEQUENCE: 223

Tyr Ser Asn Cys Pro Asp Gly Gln Ser Thr Ala Lys Thr Phe Leu
1               5                   10                  15

<210> SEQ ID NO 224
<211> LENGTH: 17
<212> TYPE: DNA
<213> ORGANISM: Artificial Sequence
<220> FEATURE:
<223> OTHER INFORMATION: Primer

<400> SEQUENCE: 224
gggtgcatcg tttacgc                                              17

<210> SEQ ID NO 225
<211> LENGTH: 23
<212> TYPE: DNA
<213> ORGANISM: Artificial Sequence
<220> FEATURE:
<223> OTHER INFORMATION: Primer

<400> SEQUENCE: 225
ctgctgctga ggaaggatat gag                                       23

<210> SEQ ID NO 226
<211> LENGTH: 34
<212> TYPE: DNA
<213> ORGANISM: Artificial Sequence
<220> FEATURE:
<223> OTHER INFORMATION: Primer

<400> SEQUENCE: 226
taatacgact cactataggg tgcatcgttt acgc                           34

<210> SEQ ID NO 227
<211> LENGTH: 23
<212> TYPE: DNA
<213> ORGANISM: Artificial Sequence
<220> FEATURE:
<223> OTHER INFORMATION: Primer

<400> SEQUENCE: 227
ctcatatcct tcctcagcag cag                                       23

<210> SEQ ID NO 228
<211> LENGTH: 461
<212> TYPE: PRT
<213> ORGANISM: Homo sapiens

<400> SEQUENCE: 228

Gln Thr Ser Val Ser Pro Ser Lys Val Ile Leu Pro Arg Gly Gly Ser
1               5                   10                  15

Val Leu Val Thr Cys Ser Thr Ser Cys Asp Gln Pro Lys Leu Leu Gly
                20                  25                  30

Ile Glu Thr Pro Leu Pro Lys Lys Glu Leu Leu Leu Pro Gly Asn Asn
            35                  40                  45

Arg Lys Val Tyr Glu Leu Ser Asn Val Gln Glu Asp Ser Gln Pro Met
    50                  55                  60

Cys Tyr Ser Asn Cys Pro Asp Gly Gln Ser Thr Ala Lys Thr Phe Leu
65                  70                  75                  80
```

```
Thr Val Tyr Trp Thr Pro Glu Arg Val Glu Leu Ala Pro Leu Pro Ser
                85                  90                  95

Trp Gln Pro Val Gly Lys Asn Leu Thr Leu Arg Cys Gln Val Glu Gly
            100                 105                 110

Gly Ala Pro Arg Ala Asn Leu Thr Val Val Leu Arg Gly Glu Lys
        115                 120                 125

Glu Leu Lys Arg Glu Pro Ala Val Gly Glu Pro Ala Glu Val Thr Thr
    130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
    290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Leu Lys Ala Thr Pro Glu
                325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
        355                 360                 365

Pro Arg Leu Asp Glu Arg Asp Cys Pro Gly Asn Trp Thr Trp Pro Glu
    370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
                405                 410                 415

Ser Val Thr Val Thr Arg Asp Leu Glu Gly Thr Tyr Leu Cys Arg Ala
            420                 425                 430

Arg Ser Thr Gln Gly Glu Val Thr Arg Lys Val Thr Val Asn Val Leu
        435                 440                 445

Ser Pro Arg Tyr Glu Val Asp His His His His His
    450                 455                 460

<210> SEQ ID NO 229
<211> LENGTH: 112
<212> TYPE: RNA
<213> ORGANISM: Artificial Sequence
<220> FEATURE:
```

<223> OTHER INFORMATION: Aptamer

<400> SEQUENCE: 229
gggugcaucg uuuacgcgca acauaaaaau uuaaagugcu caguugucaa ucuaugacug    60
cugcugagga aggauaugag aaacaaacaa acguauggcg gucuccaaca gg            112

<210> SEQ ID NO 230
<211> LENGTH: 20
<212> TYPE: DNA
<213> ORGANISM: Artificial Sequence
<220> FEATURE:
<223> OTHER INFORMATION: Antisense Oligo

<400> SEQUENCE: 230
cctgttggag accgccatac                                                20

<210> SEQ ID NO 231
<211> LENGTH: 547
<212> TYPE: PRT
<213> ORGANISM: Homo sapiens

<400> SEQUENCE: 231

Met Ala Thr Met Val Pro Ser Val Leu Trp Pro Arg Ala Cys Trp Thr
1               5                   10                  15

Leu Leu Val Cys Cys Leu Leu Thr Pro Gly Val Gln Gly Gln Glu Phe
            20                  25                  30

Leu Leu Arg Val Glu Pro Gln Asn Pro Val Leu Ser Ala Gly Gly Ser
        35                  40                  45

Leu Phe Val Asn Cys Ser Thr Asp Cys Pro Ser Ser Glu Lys Ile Ala
    50                  55                  60

Leu Glu Thr Ser Leu Ser Lys Glu Leu Val Ala Ser Gly Met Gly Trp
65                  70                  75                  80

Ala Ala Phe Asn Leu Ser Asn Val Thr Gly Asn Ser Arg Ile Leu Cys
                85                  90                  95

Ser Val Tyr Cys Asn Gly Ser Gln Ile Thr Gly Ser Ser Asn Ile Thr
            100                 105                 110

Val Tyr Arg Leu Pro Glu Arg Val Glu Leu Ala Pro Leu Pro Pro Trp
        115                 120                 125

Gln Pro Val Gly Gln Asn Phe Thr Leu Arg Cys Gln Val Glu Asp Gly
    130                 135                 140

Ser Pro Arg Thr Ser Leu Thr Val Val Leu Leu Arg Trp Glu Glu Glu
145                 150                 155                 160

Leu Ser Arg Gln Pro Ala Val Glu Glu Pro Ala Glu Val Thr Ala Thr
                165                 170                 175

Val Leu Ala Ser Arg Asp Asp His Gly Ala Pro Phe Ser Cys Arg Thr
            180                 185                 190

Glu Leu Asp Met Gln Pro Gln Gly Leu Gly Leu Phe Val Asn Thr Ser
        195                 200                 205

Ala Pro Arg Gln Leu Arg Thr Phe Val Leu Pro Val Thr Pro Pro Arg
    210                 215                 220

Leu Val Ala Pro Arg Phe Leu Glu Val Glu Thr Ser Trp Pro Val Asp
225                 230                 235                 240

Cys Thr Leu Asp Gly Leu Phe Pro Ala Ser Glu Ala Gln Val Tyr Leu
                245                 250                 255

Ala Leu Gly Asp Gln Met Leu Asn Ala Thr Val Met Asn His Gly Asp
            260                 265                 270

Thr Leu Thr Ala Thr Ala Thr Ala Arg Ala Asp Gln Glu Gly
        275                 280                 285

Ala Arg Glu Ile Val Cys Asn Val Thr Leu Gly Gly Glu Arg Arg Glu
290                 295                 300

Ala Arg Glu Asn Leu Thr Val Phe Ser Phe Leu Gly Pro Ile Val Asn
305                 310                 315                 320

Leu Ser Glu Pro Thr Ala His Glu Gly Ser Thr Val Thr Val Ser Cys
                325                 330                 335

Met Ala Gly Ala Arg Val Gln Val Thr Leu Asp Gly Val Pro Ala Ala
            340                 345                 350

Ala Pro Gly Gln Pro Ala Gln Leu Gln Leu Asn Ala Thr Glu Ser Asp
        355                 360                 365

Asp Gly Arg Ser Phe Phe Cys Ser Ala Thr Leu Glu Val Asp Gly Glu
370                 375                 380

Phe Leu His Arg Asn Ser Ser Val Gln Leu Arg Val Leu Tyr Gly Pro
385                 390                 395                 400

Lys Ile Asp Arg Ala Thr Cys Pro Gln His Leu Lys Trp Lys Asp Lys
                405                 410                 415

Thr Arg His Val Leu Gln Cys Gln Ala Arg Gly Asn Pro Tyr Pro Glu
            420                 425                 430

Leu Arg Cys Leu Lys Glu Gly Ser Ser Arg Glu Val Pro Val Gly Ile
        435                 440                 445

Pro Phe Phe Val Asn Val Thr His Asn Gly Thr Tyr Gln Cys Gln Ala
450                 455                 460

Ser Ser Ser Arg Gly Lys Tyr Thr Leu Val Val Val Met Asp Ile Glu
465                 470                 475                 480

Ala Gly Ser Ser His Phe Val Pro Val Phe Val Ala Val Leu Leu Thr
                485                 490                 495

Leu Gly Val Val Thr Ile Val Leu Ala Leu Met Tyr Val Phe Arg Glu
            500                 505                 510

His Gln Arg Ser Gly Ser Tyr His Val Arg Glu Glu Ser Thr Tyr Leu
        515                 520                 525

Pro Leu Thr Ser Met Gln Pro Thr Glu Ala Met Gly Glu Glu Pro Ser
530                 535                 540

Arg Ala Glu
545

<210> SEQ ID NO 232
<211> LENGTH: 456
<212> TYPE: PRT
<213> ORGANISM: Homo sapiens

<400> SEQUENCE: 232

Gln Glu Phe Leu Leu Arg Val Glu Pro Gln Asn Pro Val Leu Ser Ala
1               5                   10                  15

Gly Gly Ser Leu Phe Val Asn Cys Ser Thr Asp Cys Pro Ser Ser Glu
            20                  25                  30

Lys Ile Ala Leu Glu Thr Ser Leu Ser Lys Glu Leu Val Ala Ser Gly
        35                  40                  45

Met Gly Trp Ala Ala Phe Asn Leu Ser Asn Val Thr Gly Asn Ser Arg
50                  55                  60

Ile Leu Cys Ser Val Tyr Cys Asn Gly Ser Gln Ile Thr Gly Ser Ser
65                  70                  75                  80

Asn Ile Thr Val Tyr Arg Leu Pro Glu Arg Val Glu Leu Ala Pro Leu
                85                  90                  95

```
Pro Pro Trp Gln Pro Val Gly Gln Asn Phe Thr Leu Arg Cys Gln Val
            100                 105                 110

Glu Asp Gly Ser Pro Arg Thr Ser Leu Thr Val Val Leu Leu Arg Trp
        115                 120                 125

Glu Glu Glu Leu Ser Arg Gln Pro Ala Val Glu Glu Pro Ala Glu Val
130                 135                 140

Thr Ala Thr Val Leu Ala Ser Arg Asp Asp His Gly Ala Pro Phe Ser
145                 150                 155                 160

Cys Arg Thr Glu Leu Asp Met Gln Pro Gln Gly Leu Gly Leu Phe Val
                165                 170                 175

Asn Thr Ser Ala Pro Arg Gln Leu Arg Thr Phe Val Leu Pro Val Thr
            180                 185                 190

Pro Pro Arg Leu Val Ala Pro Arg Phe Leu Glu Val Glu Thr Ser Trp
        195                 200                 205

Pro Val Asp Cys Thr Leu Asp Gly Leu Phe Pro Ala Ser Glu Ala Gln
210                 215                 220

Val Tyr Leu Ala Leu Gly Asp Gln Met Leu Asn Ala Thr Val Met Asn
225                 230                 235                 240

His Gly Asp Thr Leu Thr Ala Thr Ala Thr Ala Thr Ala Arg Ala Asp
                245                 250                 255

Gln Glu Gly Ala Arg Glu Ile Val Cys Asn Val Thr Leu Gly Gly Glu
            260                 265                 270

Arg Arg Glu Ala Arg Glu Asn Leu Thr Val Phe Ser Phe Leu Gly Pro
        275                 280                 285

Ile Val Asn Leu Ser Glu Pro Thr Ala His Glu Gly Ser Thr Val Thr
290                 295                 300

Val Ser Cys Met Ala Gly Ala Arg Val Gln Val Thr Leu Asp Gly Val
305                 310                 315                 320

Pro Ala Ala Ala Pro Gly Gln Pro Ala Gln Leu Gln Leu Asn Ala Thr
                325                 330                 335

Glu Ser Asp Asp Gly Arg Ser Phe Phe Cys Ser Ala Thr Leu Glu Val
            340                 345                 350

Asp Gly Glu Phe Leu His Arg Asn Ser Ser Val Gln Leu Arg Val Leu
        355                 360                 365

Tyr Gly Pro Lys Ile Asp Arg Ala Thr Cys Pro Gln His Leu Lys Trp
370                 375                 380

Lys Asp Lys Thr Arg His Val Leu Gln Cys Gln Ala Arg Gly Asn Pro
385                 390                 395                 400

Tyr Pro Glu Leu Arg Cys Leu Lys Glu Gly Ser Ser Arg Glu Val Pro
                405                 410                 415

Val Gly Ile Pro Phe Phe Val Asn Val Thr His Asn Gly Thr Tyr Gln
            420                 425                 430

Cys Gln Ala Ser Ser Ser Arg Gly Lys Tyr Thr Leu Val Val Val Met
        435                 440                 445

Asp Ile Glu Ala Gly Ser Ser His
    450                 455

<210> SEQ ID NO 233
<211> LENGTH: 924
<212> TYPE: PRT
<213> ORGANISM: Homo sapiens

<400> SEQUENCE: 233

Met Pro Gly Pro Ser Pro Gly Leu Arg Arg Ala Leu Leu Gly Leu Trp
```

```
1               5                   10                  15
Ala Ala Leu Gly Leu Gly Leu Phe Gly Leu Ser Ala Val Ser Gln Glu
             20                  25                  30
Pro Phe Trp Ala Asp Leu Gln Pro Arg Val Ala Phe Val Glu Arg Gly
             35                  40                  45
Gly Ser Leu Trp Leu Asn Cys Ser Thr Asn Cys Pro Arg Pro Glu Arg
50                  55                  60
Gly Gly Leu Glu Thr Ser Leu Arg Arg Asn Gly Thr Gln Arg Gly Leu
65                  70                  75                  80
Arg Trp Leu Ala Arg Gln Leu Val Asp Ile Arg Glu Pro Glu Thr Gln
             85                  90                  95
Pro Val Cys Phe Phe Arg Cys Ala Arg Arg Thr Leu Gln Ala Arg Gly
             100                 105                 110
Leu Ile Arg Thr Phe Gln Arg Pro Asp Arg Val Glu Leu Met Pro Leu
             115                 120                 125
Pro Pro Trp Gln Pro Val Gly Glu Asn Phe Thr Leu Ser Cys Arg Val
        130                 135                 140
Pro Gly Ala Gly Pro Arg Ala Ser Leu Thr Leu Thr Leu Leu Arg Gly
145                 150                 155                 160
Ala Gln Glu Leu Ile Arg Arg Ser Phe Ala Gly Glu Pro Pro Arg Ala
                 165                 170                 175
Arg Gly Ala Val Leu Thr Ala Thr Val Leu Ala Arg Arg Glu Asp His
             180                 185                 190
Gly Ala Asn Phe Ser Cys Arg Ala Glu Leu Asp Leu Arg Pro His Gly
             195                 200                 205
Leu Gly Leu Phe Glu Asn Ser Ser Ala Pro Arg Glu Leu Arg Thr Phe
210                 215                 220
Ser Leu Ser Pro Asp Ala Pro Arg Leu Ala Ala Pro Arg Leu Leu Glu
225                 230                 235                 240
Val Gly Ser Glu Arg Pro Val Ser Cys Thr Leu Asp Gly Leu Phe Pro
             245                 250                 255
Ala Ser Glu Ala Arg Val Tyr Leu Ala Leu Gly Asp Gln Asn Leu Ser
             260                 265                 270
Pro Asp Val Thr Leu Glu Gly Asp Ala Phe Val Ala Thr Ala Thr Ala
             275                 280                 285
Thr Ala Ser Ala Glu Gln Glu Gly Ala Arg Gln Leu Val Cys Asn Val
         290                 295                 300
Thr Leu Gly Gly Glu Asn Arg Glu Thr Arg Glu Asn Val Thr Ile Tyr
305                 310                 315                 320
Ser Phe Pro Ala Pro Leu Leu Thr Leu Ser Glu Pro Ser Val Ser Glu
                 325                 330                 335
Gly Gln Met Val Thr Val Thr Cys Ala Ala Gly Ala Gln Ala Leu Val
             340                 345                 350
Thr Leu Glu Gly Val Pro Ala Val Pro Gly Gln Pro Ala Gln Leu
             355                 360                 365
Gln Leu Asn Ala Thr Glu Asn Asp Asp Arg Arg Ser Phe Phe Cys Asp
         370                 375                 380
Ala Thr Leu Asp Val Asp Gly Glu Thr Leu Ile Lys Asn Arg Ser Ala
385                 390                 395                 400
Glu Leu Arg Val Leu Tyr Ala Pro Arg Leu Asp Asp Ser Asp Cys Pro
             405                 410                 415
Arg Ser Trp Thr Trp Pro Glu Gly Pro Glu Gln Thr Leu Arg Cys Glu
             420                 425                 430
```

```
Ala Arg Gly Asn Pro Glu Pro Ser Val His Cys Ala Arg Ser Asp Gly
            435                 440                 445

Gly Ala Val Leu Ala Leu Gly Leu Leu Gly Pro Val Thr Arg Ala Leu
    450                 455                 460

Ser Gly Thr Tyr Arg Cys Lys Ala Ala Asn Asp Gln Gly Glu Ala Val
465                 470                 475                 480

Lys Asp Val Thr Leu Thr Val Glu Tyr Ala Pro Ala Leu Asp Ser Val
                485                 490                 495

Gly Cys Pro Glu Arg Ile Thr Trp Leu Glu Gly Thr Glu Ala Ser Leu
            500                 505                 510

Ser Cys Val Ala His Gly Val Pro Pro Asp Val Ile Cys Val Arg
            515                 520                 525

Ser Gly Glu Leu Gly Ala Val Ile Glu Gly Leu Leu Arg Val Ala Arg
            530                 535                 540

Glu His Ala Gly Thr Tyr Arg Cys Glu Ala Thr Asn Pro Arg Gly Ser
545                 550                 555                 560

Ala Ala Lys Asn Val Ala Val Thr Val Glu Tyr Gly Pro Arg Phe Glu
                565                 570                 575

Glu Pro Ser Cys Pro Ser Asn Trp Thr Trp Val Glu Gly Ser Gly Arg
            580                 585                 590

Leu Phe Ser Cys Glu Val Asp Gly Lys Pro Gln Pro Ser Val Lys Cys
            595                 600                 605

Val Gly Ser Gly Gly Ala Thr Glu Gly Val Leu Leu Pro Leu Ala Pro
            610                 615                 620

Pro Asp Pro Ser Pro Arg Ala Pro Arg Ile Pro Arg Val Leu Ala Pro
625                 630                 635                 640

Gly Ile Tyr Val Cys Asn Ala Thr Asn Arg His Gly Ser Val Ala Lys
                645                 650                 655

Thr Val Val Ser Ala Glu Ser Pro Pro Glu Met Asp Glu Ser Thr
            660                 665                 670

Cys Pro Ser His Gln Thr Trp Leu Glu Gly Ala Glu Ala Ser Ala Leu
            675                 680                 685

Ala Cys Ala Ala Arg Gly Arg Pro Ser Pro Gly Val Arg Cys Ser Arg
            690                 695                 700

Glu Gly Ile Pro Trp Pro Glu Gln Gln Arg Val Ser Arg Glu Asp Ala
705                 710                 715                 720

Gly Thr Tyr His Cys Val Ala Thr Asn Ala His Gly Thr Asp Ser Arg
                725                 730                 735

Thr Val Thr Val Gly Val Glu Tyr Arg Pro Val Val Ala Glu Leu Ala
            740                 745                 750

Ala Ser Pro Pro Gly Gly Val Arg Pro Gly Gly Asn Phe Thr Leu Thr
            755                 760                 765

Cys Arg Ala Glu Ala Trp Pro Pro Ala Gln Ile Ser Trp Arg Ala Pro
770                 775                 780

Pro Gly Ala Leu Asn Ile Gly Leu Ser Ser Asn Ser Thr Leu Ser
785                 790                 795                 800

Val Ala Gly Ala Met Gly Ser His Gly Gly Glu Tyr Glu Cys Ala Ala
                805                 810                 815

Thr Asn Ala His Gly Arg His Ala Arg Arg Ile Thr Val Arg Val Ala
            820                 825                 830

Gly Pro Trp Leu Trp Val Ala Val Gly Ala Ala Gly Gly Ala Ala
            835                 840                 845
```

```
Leu Leu Ala Ala Gly Ala Gly Leu Ala Phe Tyr Val Gln Ser Thr Ala
            850                 855                 860

Cys Lys Lys Gly Glu Tyr Asn Val Gln Glu Ala Glu Ser Ser Gly Glu
865                 870                 875                 880

Ala Val Cys Leu Asn Gly Ala Gly Gly Ala Gly Ala Gly Ala Ala Gly
                885                 890                 895

Ala Glu Gly Gly Pro Glu Ala Ala Gly Gly Ala Ala Glu Ser Pro Ala
                900                 905                 910

Glu Gly Glu Val Phe Ala Ile Gln Leu Thr Ser Ala
                915                 920

<210> SEQ ID NO 234
<211> LENGTH: 804
<212> TYPE: PRT
<213> ORGANISM: Homo sapiens

<400> SEQUENCE: 234

Glu Pro Phe Trp Ala Asp Leu Gln Pro Arg Val Ala Phe Val Glu Arg
1               5                   10                  15

Gly Gly Ser Leu Trp Leu Asn Cys Ser Thr Asn Cys Pro Arg Pro Glu
                20                  25                  30

Arg Gly Gly Leu Glu Thr Ser Leu Arg Arg Asn Gly Thr Gln Arg Gly
            35                  40                  45

Leu Arg Trp Leu Ala Arg Gln Leu Val Asp Ile Arg Glu Pro Glu Thr
50                  55                  60

Gln Pro Val Cys Phe Phe Arg Cys Ala Arg Thr Leu Gln Ala Arg
65                  70                  75                  80

Gly Leu Ile Arg Thr Phe Gln Arg Pro Asp Arg Val Glu Leu Met Pro
                85                  90                  95

Leu Pro Pro Trp Gln Pro Val Gly Glu Asn Phe Thr Leu Ser Cys Arg
                100                 105                 110

Val Pro Gly Ala Gly Pro Arg Ala Ser Leu Thr Leu Thr Leu Leu Arg
            115                 120                 125

Gly Ala Gln Glu Leu Ile Arg Arg Ser Phe Ala Gly Glu Pro Pro Arg
130                 135                 140

Ala Arg Gly Ala Val Leu Thr Ala Thr Val Leu Ala Arg Arg Glu Asp
145                 150                 155                 160

His Gly Ala Asn Phe Ser Cys Arg Ala Glu Leu Asp Leu Arg Pro His
                165                 170                 175

Gly Leu Gly Leu Phe Glu Asn Ser Ser Ala Pro Arg Glu Leu Arg Thr
            180                 185                 190

Phe Ser Leu Ser Pro Asp Ala Pro Arg Leu Ala Ala Pro Arg Leu Leu
            195                 200                 205

Glu Val Gly Ser Glu Arg Pro Val Ser Cys Thr Leu Asp Gly Leu Phe
210                 215                 220

Pro Ala Ser Glu Ala Arg Val Tyr Leu Ala Leu Gly Asp Gln Asn Leu
225                 230                 235                 240

Ser Pro Asp Val Thr Leu Glu Gly Asp Ala Phe Val Ala Thr Ala Thr
                245                 250                 255

Ala Thr Ala Ser Ala Glu Gln Glu Gly Ala Arg Gln Leu Val Cys Asn
            260                 265                 270

Val Thr Leu Gly Gly Glu Asn Arg Glu Thr Arg Glu Asn Val Thr Ile
            275                 280                 285

Tyr Ser Phe Pro Ala Pro Leu Leu Thr Leu Ser Glu Pro Ser Val Ser
290                 295                 300
```

```
Glu Gly Gln Met Val Thr Val Thr Cys Ala Ala Gly Ala Gln Ala Leu
305                 310                 315                 320

Val Thr Leu Glu Gly Val Pro Ala Ala Val Pro Gly Gln Pro Ala Gln
                325                 330                 335

Leu Gln Leu Asn Ala Thr Glu Asn Asp Asp Arg Arg Ser Phe Phe Cys
            340                 345                 350

Asp Ala Thr Leu Asp Val Asp Gly Glu Thr Leu Ile Lys Asn Arg Ser
        355                 360                 365

Ala Glu Leu Arg Val Leu Tyr Ala Pro Arg Leu Asp Asp Ser Asp Cys
370                 375                 380

Pro Arg Ser Trp Thr Trp Pro Glu Gly Pro Gln Thr Leu Arg Cys
385                 390                 395                 400

Glu Ala Arg Gly Asn Pro Glu Pro Ser Val His Cys Ala Arg Ser Asp
                405                 410                 415

Gly Gly Ala Val Leu Ala Leu Gly Leu Leu Gly Pro Val Thr Arg Ala
            420                 425                 430

Leu Ser Gly Thr Tyr Arg Cys Lys Ala Ala Asn Asp Gln Gly Glu Ala
        435                 440                 445

Val Lys Asp Val Thr Leu Thr Val Glu Tyr Ala Pro Ala Leu Asp Ser
450                 455                 460

Val Gly Cys Pro Glu Arg Ile Thr Trp Leu Glu Gly Thr Glu Ala Ser
465                 470                 475                 480

Leu Ser Cys Val Ala His Gly Val Pro Pro Pro Asp Val Ile Cys Val
                485                 490                 495

Arg Ser Gly Glu Leu Gly Ala Val Ile Glu Gly Leu Leu Arg Val Ala
            500                 505                 510

Arg Glu His Ala Gly Thr Tyr Arg Cys Glu Ala Thr Asn Pro Arg Gly
        515                 520                 525

Ser Ala Ala Lys Asn Val Ala Val Thr Val Glu Tyr Gly Pro Arg Phe
530                 535                 540

Glu Glu Pro Ser Cys Pro Ser Asn Trp Thr Trp Val Glu Gly Ser Gly
545                 550                 555                 560

Arg Leu Phe Ser Cys Glu Val Asp Gly Lys Pro Gln Pro Ser Val Lys
                565                 570                 575

Cys Val Gly Ser Gly Gly Ala Thr Glu Gly Val Leu Leu Pro Leu Ala
            580                 585                 590

Pro Pro Asp Pro Ser Pro Arg Ala Pro Arg Ile Pro Arg Val Leu Ala
        595                 600                 605

Pro Gly Ile Tyr Val Cys Asn Ala Thr Asn Arg His Gly Ser Val Ala
610                 615                 620

Lys Thr Val Val Ser Ala Glu Ser Pro Glu Met Asp Glu Ser
625                 630                 635                 640

Thr Cys Pro Ser His Gln Thr Trp Leu Glu Gly Ala Glu Ala Ser Ala
                645                 650                 655

Leu Ala Cys Ala Ala Arg Gly Arg Pro Ser Pro Gly Val Arg Cys Ser
            660                 665                 670

Arg Glu Gly Ile Pro Trp Pro Glu Gln Gln Arg Val Ser Arg Glu Asp
        675                 680                 685

Ala Gly Thr Tyr His Cys Val Ala Thr Asn Ala His Gly Thr Asp Ser
690                 695                 700

Arg Thr Val Thr Val Gly Val Glu Tyr Arg Pro Val Val Ala Glu Leu
705                 710                 715                 720
```

```
Ala Ala Ser Pro Pro Gly Gly Val Arg Pro Gly Gly Asn Phe Thr Leu
            725             730             735

Thr Cys Arg Ala Glu Ala Trp Pro Pro Ala Gln Ile Ser Trp Arg Ala
            740             745             750

Pro Pro Gly Ala Leu Asn Ile Gly Leu Ser Ser Asn Asn Ser Thr Leu
            755             760             765

Ser Val Ala Gly Ala Met Gly Ser His Gly Gly Glu Tyr Glu Cys Ala
    770             775             780

Ala Thr Asn Ala His Gly Arg His Ala Arg Arg Ile Thr Val Arg Val
785             790             795             800

Ala Gly Pro Trp

<210> SEQ ID NO 235
<211> LENGTH: 12
<212> TYPE: RNA
<213> ORGANISM: Artificial Sequence
<220> FEATURE:
<223> OTHER INFORMATION: Synthetic Spacer Sequence

<400> SEQUENCE: 235
aaacaaacaa ac                                                           12

<210> SEQ ID NO 236
<211> LENGTH: 20
<212> TYPE: RNA
<213> ORGANISM: Artificial Sequence
<220> FEATURE:
<223> OTHER INFORMATION: Synthetic Sense Binding Sequence

<400> SEQUENCE: 236
guauggcggu cuccaacagg                                                   20
```